(12) United States Patent
Nagase et al.

(10) Patent No.: US 10,377,763 B2
(45) Date of Patent: Aug. 13, 2019

(54) MORPHINAN DERIVATIVE AND MEDICAL USAGE THEREOF

(71) Applicant: UNIVERSITY OF TSUKUBA, Tsukuba-shi, Ibaraki (JP)

(72) Inventors: Hiroshi Nagase, Tsukuba (JP); Naoshi Yamamoto, Tsukuba (JP); Yoko Irukayama, Tsukuba (JP); Tsuyoshi Saitoh, Tsukuba (JP); Masashi Yanagisawa, Tsukuba (JP); Yasuyuki Nagumo, Tsukuba (JP)

(73) Assignee: UNIVERSITY OF TSUKUBA, Tsukuba-Shi, Ibaraki (JP)

( * ) Notice: Subject to any disclaimer, the term of this patent is extended or adjusted under 35 U.S.C. 154(b) by 0 days.

(21) Appl. No.: 15/769,223

(22) PCT Filed: Oct. 28, 2016

(86) PCT No.: PCT/JP2016/081995
§ 371 (c)(1),
(2) Date: Apr. 18, 2018

(87) PCT Pub. No.: WO2017/073710
PCT Pub. Date: May 4, 2017

(65) Prior Publication Data
US 2018/0305369 A1    Oct. 25, 2018

(30) Foreign Application Priority Data

Oct. 29, 2015  (JP) .................................. 2015-212553
Aug. 8, 2016  (JP) .................................. 2016-155477

(51) Int. Cl.
| | | |
|---|---|---|
| C07D 489/08 | (2006.01) |
| A61K 31/485 | (2006.01) |
| C07D 489/06 | (2006.01) |
| A61P 25/36 | (2006.01) |
| C07D 489/02 | (2006.01) |
| A61P 25/30 | (2006.01) |

(52) U.S. Cl.
CPC .......... *C07D 489/08* (2013.01); *A61K 31/485* (2013.01); *A61P 25/30* (2018.01); *A61P 25/36* (2018.01); *C07D 489/02* (2013.01); *C07D 489/06* (2013.01)

(58) Field of Classification Search
CPC .. C07D 489/08; C07D 489/06; C07D 489/02; A61K 31/484; A61P 25/36; A61P 25/30
See application file for complete search history.

(56) References Cited

FOREIGN PATENT DOCUMENTS

| | | |
|---|---|---|
| EP | 0 577 847 A1 | 1/1994 |
| EP | 0 663 401 B1 | 7/1995 |
| EP | 0 974 363 A1 | 1/2000 |
| EP | 2 626 350 A1 | 8/2013 |
| WO | WO 93/15081 A1 | 8/1993 |
| WO | WO 99/11289 A1 | 3/1999 |
| WO | WO 2005/118548 A1 | 12/2005 |
| WO | WO 2008/069997 A1 | 6/2008 |
| WO | WO 2012/039371 A1 | 3/2012 |
| WO | WO 2013/181172 A2 | 12/2013 |
| WO | WO 2014/152657 A1 | 9/2014 |
| WO | WO 2016/152953 A1 | 9/2016 |

OTHER PUBLICATIONS

Kim et al. Bioorganic & Medicinal Chemistry Letters 11 (2001) 1651-1654.*
NiH-National Institute on Drug Abuse 2018.*
Boss, C. and C. Roch, "Recent trends in orexin research—2010 to 2015," Bioorganic & Medicinal Chemistry Letters (2015), vol. 25, pp. 2875-2887.
English abstract of JP 2000-053572 (Feb. 22, 2000).
English translation of International Preliminary Report on Patentability and Written Opinion dated May 11, 2018, in PCT International Application No. PCT/JP2016/081995 (Forms PCT/IB/326, PCT/IB/373, PCT/ISA/237).

(Continued)

*Primary Examiner* — Shirley V Gembeh
(74) *Attorney, Agent, or Firm* — Birch, Stewart, Kolasch & Birch, LLP

(57) ABSTRACT

The purpose of the present invention is to provide a compound useful as a prophylactic or therapeutic agent for various diseases and symptoms related to orexin receptors, and a medical usage of the same.

The present invention provides a morphinan derivative represented by the general formula (I) below or a pharmaceutically acceptable acid addition salt thereof, the morphinan derivative having excellent selectivity for and antagonism against orexin receptors and excellent therapeutic and prophylactic effects on drug dependence, and an orexin receptor antagonist and a therapeutic or prophylactic agent for drug dependence each containing it as an active ingredient.

(I)

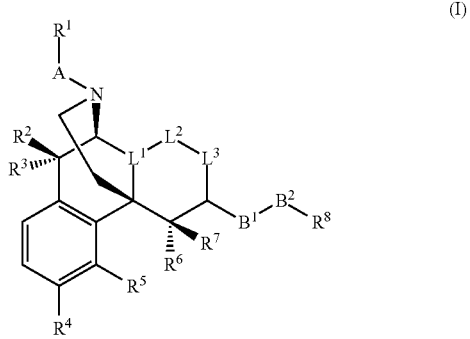

11 Claims, 1 Drawing Sheet

(56) References Cited

OTHER PUBLICATIONS

English translation of International Search Report dated Jan. 17, 2018, in PCT International Application No. PCT/JP2016/081995.
Hara, J. and T. Sakurai, "Orexin: a substance that links feeding behavior to the awakening system," Seitai-no Kagaku (Feb. 2011), vol. 62, No. 1, pp. 31-36 (with English abstract).
Ito et al., "A case of Early Childhood-onset Narcolepsy," J. Japan Pediatric Soc. (2012), vol. 116, No. 11, pp. 1728-1732 (with English abstract).
Johnson et al., "Orexin 1 receptors are a novel target to modulate panic responses and the panic brain network," Physiol. Behav. (Dec. 5, 2012), vol. 105, pp. 733-742.
Nollet et al., "Neurogenesis-Independent Antidepresssant-Like Effects on Behavior and Stress Axis Response of a Dual Orexin Receptor Antagonist in a Rodent Model of Depression," Neuropsychopharmacology (2012), vol. 37, pp. 2210-2221.
Pich, E. M. and Melotto, S., "Orexin 1 receptor antagonists in compulsive behavior and anxiety: possible therapeutic use." Front. Neurosci. (Feb. 2014), vol. 8, pp. 1-6.
Saito et al., "Affinity of Nalfurafine for its new receptor, 1P-11," Conference Proceedings of the 32th Medicinal Chemistry Symposium, 2014, Division of Medicinal Chemistry, The Pharmaceutical Society of Japan (eds.), p. 74 (with English abstract).
Tsuneki et al., "Hypothalamic orexin system regulates energy and glucose metabolism," J. Pharmacol. Sci. (2013), vol. 142, pp. 316-317.

\* cited by examiner

MORPHINAN DERIVATIVE AND MEDICAL USAGE THEREOF

TECHNICAL FIELD

The present invention relates to a morphinan derivative or a pharmaceutically acceptable acid addition salt thereof, which has excellent selectivity for and antagonism against orexin receptors, and a medical usage of the same.

BACKGROUND ART

Orexin is a brain neuropeptide produced in lateral hypothalamus. Two types of orexins, orexin A (hereinafter referred to as "OX-A"; 33 amino acid residues) and orexin B (hereinafter referred to as "OX-B"; 28 amino acid residues), are known to be produced by enzymatic cleavage of the common precursor preproorexin. Moreover, two types of G protein-coupled receptors, orexin 1 (hereinafter referred to as "OX1") receptor and orexin 2 (hereinafter referred to as "OX2") receptor, are known as receptors for orexin, and OX1 and OX2 receptors are understood to be coupled to Gq and Gq as well as Gi/o, respectively. OX-A activates OX1 and OX2 receptors with similar potencies, while OX-B relatively selectively activates OX2 receptor (Non-Patent Document 1). It is understood that putative physiological effects of orexin are exerted through either one or both of OX1 and OX2 receptors.

Orexin is known to play important roles in regulation of feeding behavior and maintenance of sleep and wakefulness, which are essential for life, and is involved in control of energy metabolism and glucose metabolism. For example, it has been observed that the expression of orexin is increased in mice or rats which are fasted, while intracerebral administration of orexin increases food intake in mice or rats. Moreover, orexin is reportedly a factor which causes changes in level of wakefulness and in emotion, depending on a metabolic state in human, and thus induces feeding, and is understood to be involved in many aspects of pathophysiology, such as obesity, eating disorder, and sleep disorder (Non-Patent Documents 2 and 3). Narcolepsy is a sleep disorder characterized by excessive daytime sleepiness, sudden loss of muscle strength in response to strong emotions, hallucinations while falling asleep, and sleep paralysis. It is a disease which also shows attention deficit hyperactivity disorder (ADHD)-like symptoms, and is reported to be caused by insufficiency of the orexin neuronal system (Non-Patent Document 4).

Also, an orexin receptor antagonist is reported to exhibit antidepressant-like effects in mouse models of depression (Non-Patent Document 5). Moreover, a recent study using OX1 receptor knock-out mice and an OX1 receptor antagonist has indicated the potential of a compound that has an inhibitory effect on OX1 receptor as a candidate therapeutic agent for addiction and misuse of drugs, including ethanol, nicotine, cocaine, cannabinoid, and morphine, and for hyperphagia and anxiety disorder (Non-Patent Document 6). Furthermore, the potential of a compound that has an inhibitory effect on OX1 receptor as a candidate therapeutic agent for panic disorder, such as panic attack and the resulting anticipatory anxiety, has also been reported (Non-Patent Document 7).

Furthermore, it is reported that orexin receptors can be involved in various pathologic conditions, such as depression, anxiety disorder, dependence, obsessive-compulsive disorder, emotional neurosis, depressive neurosis, anxiety neurosis, dysthymic disorder, behavioral disorder, mood disorder, sexual dysfunction, mental dysfunction, hypogonadism, schizophrenia, manic depression, delirium, dementia, severe mental retardation and movement disorders (such as, for example, Huntington's disease and Tourette syndrome), feeding disorder (such as, for example, hypophagia, hyperphagia, plague, and obesity), addictive eating behaviors (such as, for example, overeating/vomiting behavior), cardiovascular disease, diabetes mellitus, appetite/taste disorder, emesis, vomiting, nausea, asthma, cancer, Parkinson's disease, Cushing syndrome/disease, basophilic adenoma, prolactinoma, hyperprolactinemia, pituitary gland tumor/adenoma, hypothalamic disease, inflammatory bowel disease, gastric dyskinesia, gastric ulcer, Froehlich's syndrome, adrenohypophysis disease, pituitary disease, adrenohypophysis hypoactivity, adrenohypophysis hyperactivity, hypothalamic hypogonadism, Kallmann syndrome (such as, for example, dysosmia and hyposmia), functional or psychogenic amenorrhea, pituitary hypoactivity, hypothalamic hypothyroidism, hypothalamic adrenal insufficiency, idiopathic hyperprolactinemia, growth hormone insufficiency as a hypothalamic disease, idiopathic developmental retardations, dwarfism, gigantism, acromegaly, biological and circadian rhythm defect, neurological disorder, sleep disorder associated with neuropathic pain and a disease such as restless legs syndrome, cardiopulmonary disease, acute and congestive heart failure, hypotension, hypertension, urinary retention, osteoporosis, angina pectoris, myocardial infarction, ischemic or hemorrhagic stroke, subarachnoid hemorrhage, ulcer, allergies, benign prostatic hypertrophy, chronic renal failure, kidney disease, reduced glucose tolerance, migraine, hyperalgesia, pain, hyperpathia, enhanced or excessive hypersensitivity to pain such as burning pain and allodynia, acute pain, burning pain, atypical facial pain, neuropathic pain, back pain, type I and type II complex regional pain syndrome, arthralgia, pain caused by sport injuries, pain associated with infection (such as, for example, infection of HIV), chemotherapy-induced pain, central post-stroke pain, post-surgery pain, neuralgia, visceral pain in irritable bowel syndrome or the like and the state associated with angina pectoris, bladder incontinence (such as, for example, urgent incontinence), narcotic drug tolerance or withdrawal from narcotic drug addiction, sleep disorder, sleep apnea, narcolepsy, insomnia, parasomnia, jet lag syndrome, neurodegenerative disorders including nosologically classified events (such as, for example, a complex disease consisting of disinhibition, dementia, Parkinson's disease and muscular atrophy, and pallido-ponto-nigral degeneration), epilepsy, seizure disorder, and other diseases related to dysfunction of the orexin system (Patent Document 1).

Thus, there is a great expectation for a compound that exhibits antagonism against orexin receptors to be an agent of preventing or treating sleep disorder, obesity including obesity observed in diabetic patients, eating disorder, anxiety disorder, depression, drug dependence, obsessive-compulsive disorder and attention deficit hyperactivity disorder (ADHD), and other various diseases or symptoms related to orexin receptors.

Various compounds are known to exhibit antagonism against orexin receptors, and, for example, (2R)-2-{(1S)-6,7-dimethoxy-1-[2-(4-trifluoromethyl-phenyl)ethyl]-3,4-dihydro-1H-isoquinolin-2-yl}-N-methyl-2-phenylacetamide (Almorexant), a derivative of 1,2,3,4-tetrahydroisoquinoline, has been clinically developed as a therapeutic agent for insomnia (Patent Document 2).

Also, [(7R)-4-(5-chloro-1,3-benzoxazol-2-yl)-7-methyl-1,4-diazepan-1-yl][5-methyl-2-(2H-1,2,3-triazol-2-yl)phenyl]methanone (Suvorexant, Patent Document 3), a diazepan compound, and (1R,2R)-2-{[2,4-dimethylpyrimidin-5-yl)oxy]methyl}-2-(3-fluorophenyl)-N-(5-fluoropyridin-2-yl)cyclopropane carboxamide, a cyclopropane compound, and the like are known to be therapeutic agents for insomnia which exhibit antagonism against orexin receptors (Patent Document 4). Furthermore, various compounds having the antagonistic activity against OX receptors are disclosed in Non-Patent Document 1.

Meanwhile, Non-Patent Document 8 discloses that compounds each having a particular morphinan structure, the compounds exhibiting potent agonism at K-opioid receptor (Patent Document 5), potent antagonism against ORL1 receptor (Patent Document 6) and strong therapeutic effects on drug dependence (Patent Document 7), exhibit a weak antagonistic activity against OX1 receptor.

PRIOR ART DOCUMENTS

Patent Documents

Patent Document 1: WO13/181174
Patent Document 2: WO05/118548
Patent Document 3: WO08/069997
Patent Document 4: WO12/039371
Patent Document 5: WO93/015081
Patent Document 6: Japanese Unexamined Patent Application Publication No. 2000-53572
Patent Document 7: WO99/011289

Non-Patent Documents

Non-Patent Document 1: Boss, C. and Roch, C., Recent trends in orexin research—2010 to 2015. Bioorg. Med. Chem. Lett., Vol. 25, 2015, pp. 2875-2887.
Non-Patent Document 2: Hara, J., et al., Orexin: a substance that links feeding behavior to the awakening system, Seitai-no Kagaku, Vol. 62, No. 1, February, 2011, pp. 31-36.
Non-Patent Document 3: Tsuneki H., et al., Hypothalamic orexin system regulates energy and glucose metabolism, J. Pharmacol. Sci., Vol. 142, 2013, pp. 316-317.
Non-Patent Document 4: Ito, H., et al., A case of Early Childhood-onset Narcolepsy, J. Japan Pediatric Soc., Vol. 116, No. 11, 2012, pp. 1728-1732.
Non-Patent Document 5: Nollet, M., et al., Neurogenesis-Independent Antidepresssant-Like Effects on Behavior and Stress Axis Response of a Dual Orexin Receptor Antagonist in a Rodent Model of Depression. Neuropsychopharmacology, Vol. 37, pp. 2210-2221, 2012.
Non-Patent Document 6: Pich, E. M. and Melotto, S., Orexin 1 receptor antagonists in compulsive behavior and anxiety: possible therapeutic use. Front. Neurosci., Vol. 8, pp. 1-6, 2014.
Non-Patent Document 7: Johnson, P. L., et al., Orexin 1 receptors are a novel target to modulate panic responses and the panic brain network, Physiol. Behav., Vol. 105, pp. 733-742, 2012.
Non-Patent Document 8: Saito, T., et al., Affinity of Nalfurafine for its new receptor, 1P-11, Conference Proceedings of the 32th Medicinal Chemistry Symposium, 2014, Division of Medicinal Chemistry, The Pharmaceutical Society of Japan (eds.), p. 74.

SUMMARY OF THE INVENTION

Problem to be Solved by the Invention

However, in previously published Patent Documents 1 to 7 and Non-Patents Documents 1 to 8, there is no disclosure or no suggestion of morphinan derivatives having a particular structure and exhibiting excellent selectivity for and antagonism against orexin receptors.

Thus, an object of the present invention is to provide a novel compound having the morphinan skeleton which is useful for the treatment or prevention of various diseases or symptoms related to orexin receptors.

Means for Solving the Problem

The inventors intensively studied and consequently found that a compound having a particular structure, among those having the morphinan skeleton, or a pharmaceutically acceptable acid addition salt thereof exhibited excellent selectivity for and antagonism against orexin receptors, and thereby completed the present invention.

That is, the present invention relates to the following (1) to (11).

(1) A morphinan derivative represented by the general formula (I) below or a pharmaceutically acceptable acid addition salt thereof

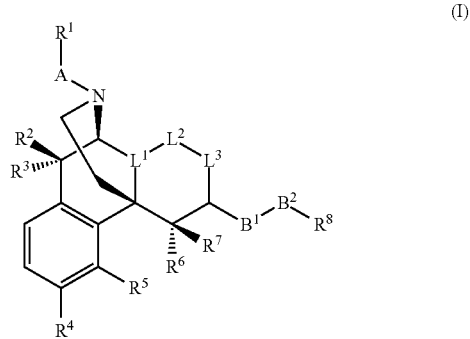

(I)

[wherein $L^1$-$L^2$-$L^3$ represents $C(R^9)$—$CH_2$—$CH_2$, $C(R^9)$—$CH=CH$, or $C=CH$—$CH_2$, wherein $R^9$ represents a hydrogen atom, hydroxy, nitro, $C_1$-$C_5$ alkanoyloxy, $C_1$-$C_5$ alkoxy, $C_1$-$C_5$ alkyl, amino, monoalkylamino (the alkyl moiety has one to five carbon atoms), dialkylamino (the alkyl moiety has one to five carbon atoms), $C_1$-$C_5$ alkanamide, benzamide, or $C_7$-$C_{14}$ aryl-alkanamide;

A represents —$C(=O)$— or —$SO_2$—;

$R^1$ represents $C_1$-$C_7$ linear or branched alkyl, $C_3$-$C_6$ cycloalkyl, $C_4$-$C_7$ cycloalkylalkyl, $C_4$-$C_6$ cycloalkenyl, $C_5$-$C_7$ cycloalkenylalkyl, $C_7$-$C_{13}$ aralkyl, $C_4$-$C_7$ alkenyl, allyl, or an organic group containing any of basic skeletons (II) below, wherein, in the basic skeletons (II), Q represents N, O, or S; T represents $CH_2$, NH, S, or O; l represents an integer of 0 to 5; m and n each independently represent an integer of 0 to 5, provided that the sum of m and n is not more than 5; said organic group represented by $R^1$ is optionally substituted by at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, carboxy, carbamoyl, N,N-dialkylcarbamoyl (the alkyl moiety has one to five carbon atoms), amidino, guanidino, isothiocyanate, trifluoromethyl, phenyl, trifluoromethoxy, and methylenedioxy;

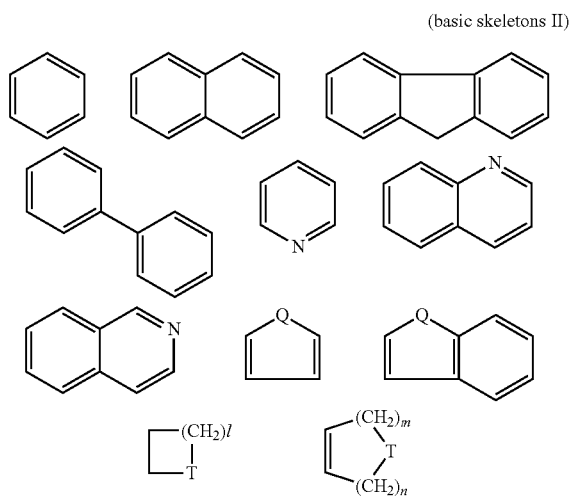

(basic skeletons II)

Q: N, O, S
T: CH$_2$, NH, S, O
l = 0-5
m, n ≥ 0
m + n ≤ 5 both R$^2$ and R$^3$ represent a hydrogen atom, or one of R$^2$ and R$^3$ represents a hydrogen atom and the other represents hydroxy, or R$^2$ and R$^3$ together represent oxo;

R$^4$ represents a hydrogen atom, hydroxy, C$_1$-C$_5$ alkoxy, C$_3$-C$_7$ alkenyloxy, C$_7$-C$_{13}$ aralkyloxy, or C$_1$-C$_5$ alkanoyloxy;

R$^5$ and R$^6$ together represent —O—, —S—, or —CH$_2$—, or R$^6$ represents a hydrogen atom and R$^5$ represents a hydrogen atom, hydroxy, C$_1$-C$_5$ alkoxy, or C$_1$-C$_5$ alkanoyloxy;

R$^7$ represents a hydrogen atom, C$_1$-C$_5$ alkyl, C$_2$-C$_5$ alkenyl, or C$_7$-C$_{13}$ aralkyl;

B$^1$ represents —N(R$^{10}$)C(=O)— or —NR$^{10}$—, wherein R$^{10}$ represents a hydrogen atom, C$_1$-C$_5$ linear or branched alkyl;

B$^2$ represents a valence bond, C$_1$-C$_{14}$ linear or branched alkylene (provided that said alkylene is optionally substituted with at least one substituent selected from the group consisting of C$_1$-C$_5$ alkoxy, C$_1$-C$_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, carboxy, carbamoyl, amidino, guanidino, trifluoromethyl, phenyl and phenoxy; and one to three methylene groups are optionally replaced with carbonyl groups), C$_2$-C$_{14}$ linear or branched acyclic unsaturated divalent hydrocarbon group containing one to three double and/or triple bonds (provided that said hydrocarbon group is optionally substituted with at least one substituent selected from the group consisting of C$_1$-C$_5$ alkoxy, C$_1$-C$_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, carboxy, carbamoyl, amidino, guanidino, trifluoromethyl, trifluoromethoxy, phenyl, and phenoxy; and one to three methylene groups are optionally replaced with carbonyl groups), or C$_1$-C$_{14}$ linear or branched saturated or unsaturated divalent hydrocarbon group containing one to five thioether bonds, ether bonds, and/or amino bonds (—N(H)—) (provided that the hetero atom comprised in said thioether bond, ether bond, or amino bond is not directly linked to B$^1$; and one to three methylene groups are optionally replaced with carbonyl or sulfonyl groups);

R$^8$ represents a hydrogen atom or an organic group containing any of basic skeletons (III) below, wherein, in the basic skeletons (III), Q represents N, O, or S; T represents CH$_2$, NH, S, or O; l represents an integer of 0 to 5; m and n each independently represent an integer of 0 to 5, provided that the sum of m and n is not more than 5; said organic group represented by R$^8$ is optionally substituted by at least one substituent selected from the group consisting of C$_1$-C$_5$ alkyl, C$_1$-C$_5$ alkoxy, C$_1$-C$_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, isothiocyanate, trifluoromethyl, phenyl, phenoxy, trifluoromethoxy, and methylenedioxy; and

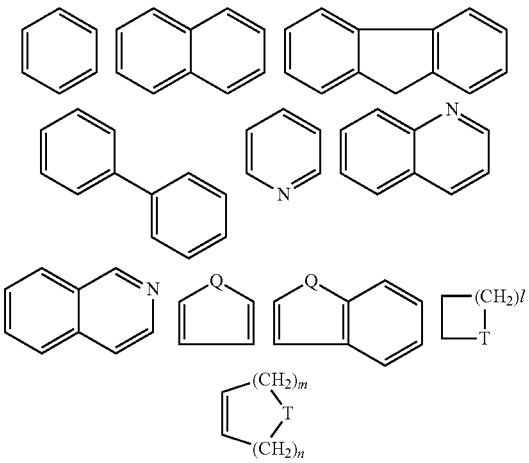

(basic skeletons III)

Q: N, O, S
T: CH$_2$, NH, S, O
l = 0-5
m, n ≥ 0
m + n ≤ 5 said general formula (I) inclusively represents the (+)-form, the (−)-form, and the (±)-form of the molecule].

In a preferred embodiment, R$^1$ represents any of basic skeletons (II) below, wherein * represents the point of attachment:

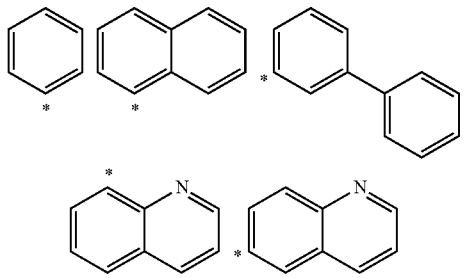

In another preferred embodiment, R$^8$ represents any of basic skeletons (III) below, wherein * represents the point of attachment:

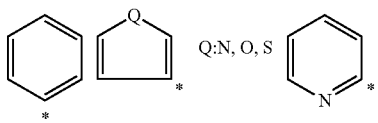

Q: N, O, S (2) The morphinan derivative or the pharmaceutically acceptable acid addition salt thereof according to (1), wherein $L^1$-$L^2$-$L^3$ represents $C(R^9)$—$CH_2$—$CH_2$ (where $R^9$ has the same definition as above) or $C$=$CH$—$CH_2$, and wherein $R^5$ and $R^6$ together represent —O—.

(3) The morphinan derivative or the pharmaceutically acceptable acid addition salt thereof according to (1) or (2), wherein $R^8$ represents an organic group containing any of basic skeletons below.

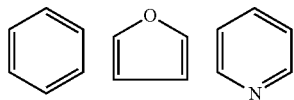

(4) The morphinan derivative or the pharmaceutically acceptable acid addition salt thereof according to any of (1) to (3), wherein $R^1$ represents an organic group containing any of basic skeletons below.

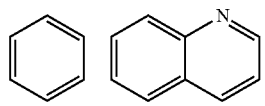

(5) The morphinan derivative or the pharmaceutically acceptable acid addition salt thereof according to any of (1) to (4), wherein $R^4$ represents $C_1$-$C_5$ alkoxy or $C_7$-$C_{13}$ aralkyloxy.

(6) A pharmaceutical drug comprising, as an active ingredient, the morphinan derivative or the pharmaceutically acceptable acid addition salt thereof according to any of (1) to (5).

(7) A pharmaceutical composition comprising, as an active ingredient, the morphinan derivative or the pharmaceutically acceptable acid addition salt thereof according to any of (1) to (5).

(8) An orexin receptor antagonist comprising, as an active ingredient, the morphinan derivative or the pharmaceutically acceptable acid addition salt thereof according to any of (1) to (5).

(9) An therapeutic or prophylactic agent for drug dependence comprising, as an active ingredient, the morphinan derivative or the pharmaceutically acceptable acid addition salt thereof according to any of (1) to (5).

(10) A therapeutic or prophylactic method for drug dependence, the method comprising administering an effective amount of the morphinan derivative or the pharmaceutically acceptable acid addition salt thereof according to any of (1) to (5) to a mammal in need of treating or preventing drug dependence.

(11) A morphinan derivative represented by the general formula (I) below or a pharmaceutically acceptable acid addition salt thereof for use in treatment or prevention of drug dependence

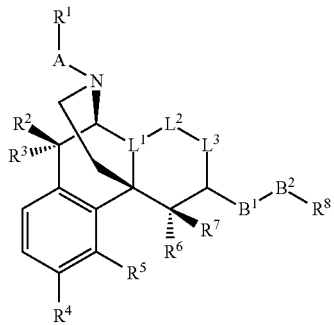

(I)

[wherein $L^1$-$L^2$-$L^3$ represents $C(R^9)$—$CH_2$—$CH_2$, $C(R^9)$—$CH$=$CH$, or $C$=$CH$—$CH_2$, wherein $R^9$ represents a hydrogen atom, hydroxy, nitro, $C_1$-$C_5$ alkanoyloxy, $C_1$-$C_5$ alkoxy, $C_1$-$C_5$ alkyl, amino, monoalkylamino (the alkyl moiety has one to five carbon atoms), dialkylamino (the alkyl moiety has one to five carbon atoms), $C_1$-$C_5$ alkanamide, benzamide, or $C_7$-$C_{14}$ aryl-alkanamide;

A represents —C(=O)— or —$SO_2$—;

$R^1$ represents $C_1$-$C_7$ linear or branched alkyl, $C_3$-$C_6$ cycloalkyl, $C_4$-$C_7$ cycloalkylalkyl, $C_4$-$C_6$ cycloalkenyl, $C_5$-$C_7$ cycloalkenylalkyl, $C_7$-$C_{13}$ aralkyl, $C_4$-$C_7$ alkenyl, allyl, or an organic group containing any of basic skeletons (II) below, wherein, in the basic skeletons (II), Q represents N, O, or S; T represents $CH_2$, NH, S, or O; l represents an integer of 0 to 5; m and n each independently represent an integer of 0 to 5, provided that the sum of m and n is not more than 5; said organic group represented by $R^1$ is optionally substituted by at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, carboxy, carbamoyl, N,N-dialkylcarbamoyl (the alkyl moiety has one to five carbon atoms), amidino, guanidino, isothiocyanate, trifluoromethyl, phenyl, trifluoromethoxy, and methylenedioxy;

(basic skeletons II)

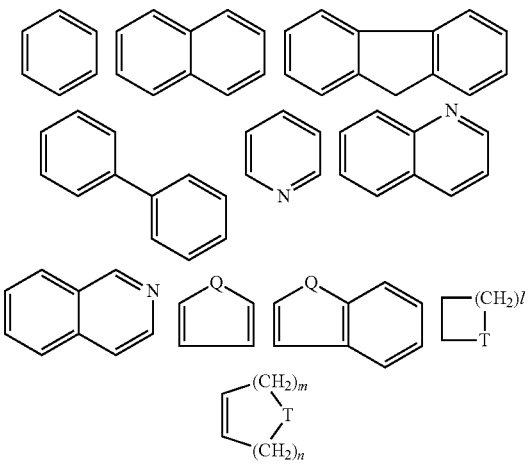

Q: N, O, S
T: $CH_2$, NH, S, O
l = 0-5
m, n ≥ 0
m + n ≤ 5 both R² and R³ represent a hydrogen atom, or one of R² and R³ represents a hydrogen atom and the other represents hydroxy, or R² and R³ together represent oxo;

R⁴ represents a hydrogen atom, hydroxy, $C_1$-$C_5$ alkoxy, $C_3$-$C_7$ alkenyloxy, $C_7$-$C_{13}$ aralkyloxy, or $C_1$-$C_5$ alkanoyloxy;

R⁵ and R⁶ together represent —O—, —S—, or —CH₂—, or R⁶ represents a hydrogen atom and R⁵ represents a hydrogen atom, hydroxy, $C_1$-$C_5$ alkoxy, or $C_1$-$C_5$ alkanoyloxy;

R⁷ represents a hydrogen atom, $C_1$-$C_5$ alkyl, $C_2$-$C_5$ alkenyl, or $C_7$-$C_{13}$ aralkyl;

B¹ represents —N(R¹⁰)C(=O)— or —NR¹⁰—, wherein R¹⁰ represents a hydrogen atom, $C_1$-$C_5$ linear or branched alkyl;

B² represents a valence bond, $C_1$-$C_{14}$ linear or branched alkylene (provided that said alkylene is optionally substituted with at least one substituent selected from the group consisting of $C_1$-$C_5$ alkoxy, $C_1$-$C_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, carboxy, carbamoyl, amidino, guanidino, trifluoromethyl, phenyl and phenoxy; and one to three methylene groups are optionally replaced with carbonyl groups), $C_2$-$C_{14}$ linear or branched acyclic unsaturated divalent hydrocarbon group containing one to three double and/or triple bonds (provided that said hydrocarbon group is optionally substituted with at least one substituent selected from the group consisting of $C_1$-$C_5$ alkoxy, $C_1$-$C_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, carboxy, carbamoyl, amidino, guanidino, trifluoromethyl, trifluoromethoxy, phenyl, and phenoxy; and one to three methylene groups are optionally replaced with carbonyl groups), or $C_1$-$C_{14}$ linear or branched saturated or unsaturated divalent hydrocarbon group containing one to five thioether bonds, ether bonds, and/or amino bonds (—N(H)—) (provided that the hetero atom comprised in said thioether bond, ether bond, or amino bond is not directly linked to B¹; and one to three methylene groups are optionally replaced with carbonyl or sulfonyl groups);

R⁸ represents a hydrogen atom or an organic group containing any of basic skeletons (III) below, wherein, in the basic skeletons (III), Q represents N, O, or S; T represents CH₂, NH, S, or O; l represents an integer of 0 to 5; m and n each independently represent an integer of 0 to 5, provided that the sum of m and n is not more than 5; said organic group represented by R⁸ is optionally substituted by at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, isothiocyanate, trifluoromethyl, phenyl, phenoxy, trifluoromethoxy, and methylenedioxy; and (basic skeletons III)

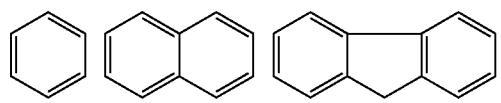

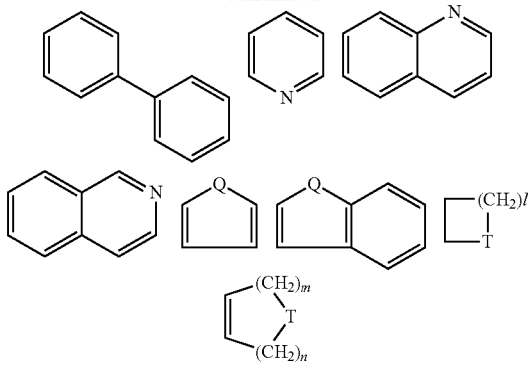

Q: N, O, S
T: CH₂, NH, S, O
l = 0-5
m, n ≥ 0
m + n ≤ 5 said general formula (I) inclusively represents the (+)-form, the (−)-form, and the (±)-form of the molecule].

In a preferred embodiment, R¹ represents any of basic skeletons (II) below, wherein * represents the point of attachment:

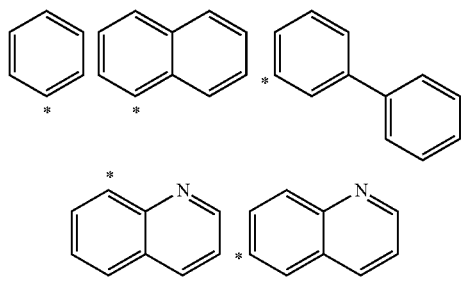

In another preferred embodiment, R⁸ represents any of basic skeletons (III) below, wherein * represents the point of attachment:

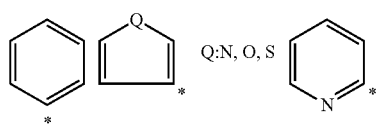

Effect of the Invention

A morphinan derivative according to the present invention or a pharmaceutically acceptable acid addition salt thereof has excellent selectivity for and antagonistic activities against orexin receptors and, therefore, is useful as a prophylactic or therapeutic agent for various diseases and symptoms related to orexin receptors.

DETAILED DESCRIPTION OF THE INVENTION

Figure 1:
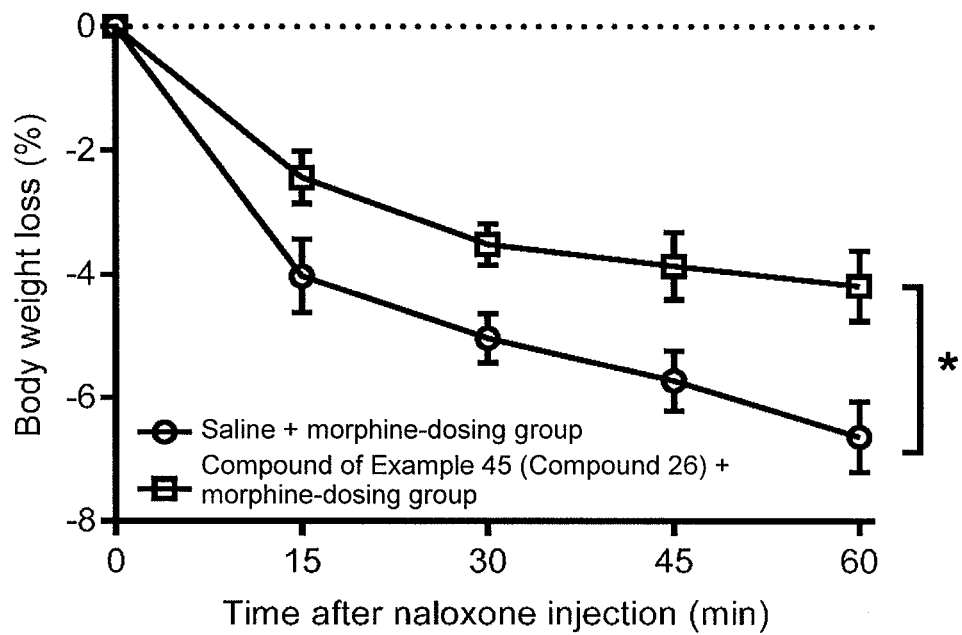
FIG. 1 depicts the effect of the compound of Example 45 (Compound 26) on the incidence of morphine physical dependence in mice (body weight loss). The asterisk indicates the statistical significance at $p<0.05$.

A morphinan derivative of the present invention or a pharmaceutically acceptable acid addition salt thereof is represented by the general formula (I) below.

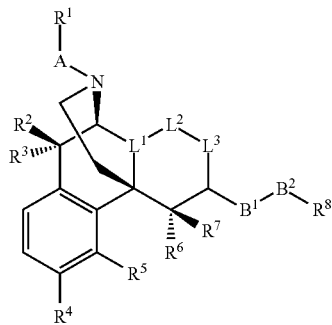

(I)

In the general formula (I), $L^1$-$L^2$-$L^3$ represents C($R^9$)—CH$_2$—CH$_2$, C($R^9$)—CH═CH, or C═CH—CH$_2$, wherein $R^9$ represents a hydrogen atom, hydroxy, nitro, $C_1$-$C_5$ alkanoyloxy, $C_1$-$C_5$ alkoxy, $C_1$-$C_5$ alkyl, amino, monoalkylamino (the alkyl moiety has one to five carbon atoms), dialkylamino (the alkyl moiety has one to five carbon atoms), $C_1$-$C_5$ alkanamide, benzamide, or $C_7$-$C_{14}$ aryl-alkanamide. Among those, $L^1$-$L^2$-$L^3$ preferably represents C($R^9$)—CH$_2$—CH$_2$ (where $R^9$ has the same definition as above) or C═CH—CH$_2$.

A represents —C(═O)— or —SO$_2$—.

$R^1$ represents $C_1$-$C_7$, preferably $C_1$-$C_5$, linear or branched alkyl, $C_3$-$C_6$, preferably $C_3$-$C_5$, cycloalkyl, $C_4$-$C_7$ cycloalkylalkyl, $C_4$-$C_6$ cycloalkenyl, $C_5$-$C_7$ cycloalkenylalkyl, $C_7$-$C_{13}$ aralkyl, $C_4$-$C_7$ alkenyl, allyl, or an organic group containing any of basic skeletons (II) below.

(basic skeletons II)

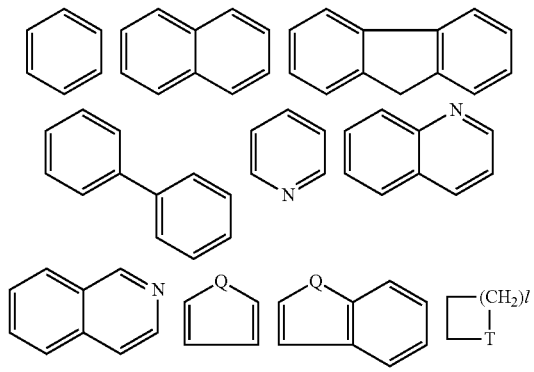

Q: N, O, S
T: CH$_2$, NH, S, O
l = 0-5
m, n ≥ 0
m + n ≤ 5

In the above basic skeletons (II), Q represents N, O, or S; T represents CH$_2$, NH, S, or O; l represents an integer of 0 to 5; m and n each independently represent an integer of 0 to 5, provided that the sum of m and n is not more than 5.

The organic group represented by $R^1$ and containing any of the above basic skeletons (II) includes monovalent groups, such as phenyl, naphthyl, or quinolinyl, derived by removing a hydrogen atom from any ring of the above basic skeletons (II); or monovalent groups, such as styryl (C$_6$H$_5$CH═CH—) or anilino (C$_6$H$_5$N(H)—), derived by removing a hydrogen atom from its side chain of any of the above basic skeletons (II).

Among those, $R^1$ is preferably an organic group containing any of basic skeletons below.

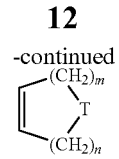

The above organic group represented by $R^1$ and containing any of the above basic skeletons (II) is optionally substituted with at least one substituent selected from the group consisting of $C_1$-$C_5$, preferably $C_1$-$C_3$, alkyl, $C_1$-$C_5$, preferably $C_1$-$C_3$, alkoxy, $C_1$-$C_5$ alkanoyloxy, hydroxy, fluorine, chlorine, bromine, iodine, amino, monoalkylamino (the alkyl moiety has one to five, preferably one to three, carbon atoms), dialkylamino (the alkyl moiety has one to five, preferably one to three, carbon atoms), nitro, cyano, carboxy, carbamoyl, N,N-dialkylcarbamoyl (the alkyl moiety has one to five, preferably one to three, carbon atoms), amidino, guanidino, isothiocyanate, trifluoromethyl, phenyl, trifluoromethoxy, and methylenedioxy. Among those, organic groups in which the above basic skeletons (II) themselves are substituted with at least one substituent selected from the above group are preferable.

Both $R^2$ and $R^3$ represent a hydrogen atom, or one of $R^2$ and $R^3$ represents a hydrogen atom and the other represents hydroxy, or $R^2$ and $R^3$ together represent oxo; among those, it is preferred that both $R^2$ and $R^3$ represent a hydrogen atom.

$R^4$ represents a hydrogen atom, hydroxy, $C_1$-$C_5$, preferably $C_1$-$C_3$, alkoxy, $C_3$-$C_7$ alkenyloxy, $C_7$-$C_{13}$ aralkyloxy, or $C_1$-$C_5$ alkanoyloxy; it preferably represents, among those, $C_1$-$C_5$ alkoxy or $C_7$-$C_{13}$ aralkyloxy.

$R^5$ and $R^6$ together represent —O—, —S—, or —CH$_2$—, or $R^6$ represents a hydrogen atom and $R^5$ represents a hydrogen atom, hydroxy, $C_1$-$C_5$ alkoxy, or $C_1$-$C_5$ alkanoyloxy; among those, it is preferred that $R^5$ and $R^6$ together represent —O—.

$R^7$ represents a hydrogen atom, $C_1$-$C_5$ alkyl, $C_2$-$C_5$ alkenyl, or $C_7$-$C_{13}$ aralkyl; it preferably represents, among those, a hydrogen atom.

$B^1$ represents —N($R^{10}$)C(═O)— or —NR$^{10}$—, wherein $R^{10}$ represents a hydrogen atom, $C_1$-$C_5$, preferably $C_1$-$C_3$, linear or branched alkyl.

$B^2$ represents a valence bond, $C_1$-$C_{14}$, preferably $C_1$-$C_5$, linear or branched alkylene (provided that said alkylene is optionally substituted with at least one substituent selected from the group consisting of $C_1$-$C_5$ alkoxy, $C_1$-$C_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, carboxy, carbamoyl, amidino, guanidino, trifluoromethyl, phenyl and phenoxy; and one to three methylene groups are optionally replaced with carbonyl groups), $C_2$-$C_{14}$, preferably $C_2$-$C_5$, linear or branched acyclic unsaturated divalent hydrocarbon group containing one to three double and/or triple bonds (provided that said hydrocarbon group is optionally substituted with at least one substituent selected from the group consisting of $C_1$-$C_5$ alkoxy, $C_1$-$C_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, carboxy, carbamoyl, amidino, guanidino, trifluoromethyl, trifluoromethoxy, phenyl, and phenoxy; and one to three methylene groups are optionally replaced with carbonyl groups), or $C_1$-$C_{14}$ linear or branched saturated or unsaturated divalent hydrocarbon group containing one to five thioether bonds, ether bonds, and/or amino bonds (—N(H)—) (provided that the hetero atom comprised in said thioether bond, ether bond, or amino bond is not directly linked to $B^1$; and one to three methylene groups are optionally replaced with carbonyl or sulfonyl groups).

If $B^1$ represents —$NR^{10}$— (provided that $R^{10}$ has the same definition as above), $B^2$ preferably represents a group selected from —C(=O)N(H)—, —C(=O)N(H)CH$_2$— and —S(=O)$_2$N(H)—.

$R^8$ represents a hydrogen atom or an organic group containing any of basic skeletons (III) below.

(basic skeletons III)

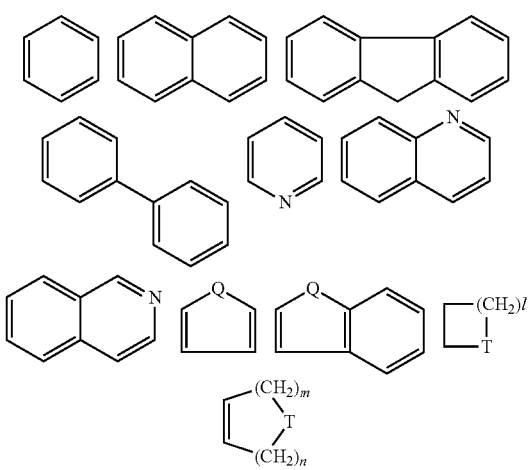

Q: N, O, S
T: CH$_2$, NH, S, O
l = 0-5
m, n ≥ 0
m + n ≤ 5

In the above basic skeletons (III), Q represents N, O, or S; T represents CH$_2$, NH, S, or O; l represents an integer of 0 to 5; m and n each independently represent an integer of 0 to 5, provided that the sum of m and n is not more than 5.

The organic group represented by $R^8$ and containing any of the above basic skeletons (III) includes monovalent groups, such as phenyl or furyl, derived by removing a hydrogen atom from any ring of the above basic skeletons (III).

Among those, $R^8$ is preferably an organic group containing any of basic skeletons below.

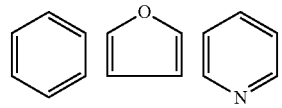

The organic group represented by $R^8$ and containing any of the above basic skeletons (III) is optionally substituted with at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, isothiocyanate, trifluoromethyl, phenyl, phenoxy, trifluoromethoxy, and methylenedioxy.

The above general formula (I) inclusively represents the (+)-form, the (−)-form, and the (±)-form of the molecule.

A morphinan derivative represented by the general formula (I) according to the present invention can be produced by a method as described below. For example, (E)-3-(furan-3-yl)-N-[(4R,4aS,7R,7aR,12bS)-4a-hydroxy-9-methoxy-3-(phenylsulfonyl)-2,3,4,4a,5,6,7,7a-octahydro-1H-4,12-methanobenzofuro[3,2-e]isoquinolin-7-yl]-N-methylacrylamide (Compound 6), a compound represented by the general formula (I) in which A is "—SO$_2$—" and $R^8$ is "2-furyl" out of the above basic skeletons (III), can be produced by the steps (1) and (2) of the reaction scheme 1 below.

Reaction scheme 1

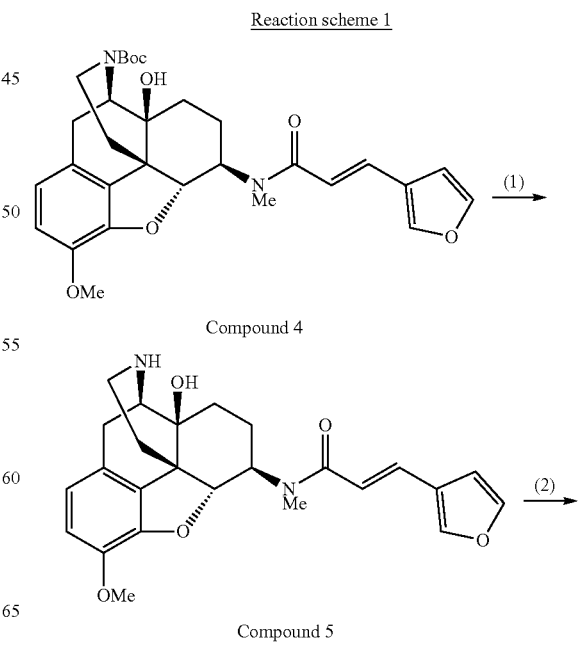

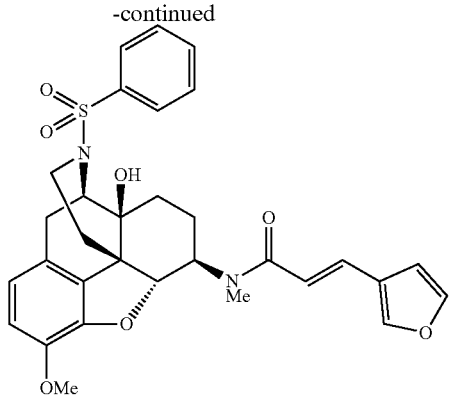

Compound 6

In the step (1) of the above scheme 1, Compound 4, which has been synthesized, for example, according to the method described in Chem. Pharm. Bull., Vol. 52, No. 6, pp. 670-674, 2004, is dissolved in hydrogen chloride-methanol under argon atmosphere, and the resulting mixture is stirred at room temperature for a predetermined time period. Then, the reaction mixture is concentrated under reduced pressure, a saturated aqueous solution of sodium hydrogencarbonate and potassium carbonate are added to the residue, and subsequently the resulting mixture is extracted with 2-propanol/chloroform. The organic layer is washed with saturated brine, dried over sodium sulfate, and then concentrated under reduced pressure. The obtained crude product is purified by silica gel chromatography to give Compound 5.

Next, in the step (2) of the above scheme 1, Compound 5 is dissolved in a solvent, such as anhydrous dichloromethane, under argon atmosphere, and triethylamine is added thereto, and benzenesulfonyl chloride is added to the obtained solution on ice, and the resulting mixture is stirred at room temperature for a predetermined time period. Then, the reaction mixture is diluted with a solvent, such as dichloromethane, and the resulting solution is washed with a saturated aqueous solution of sodium hydrogencarbonate and saturated brine, dried over sodium sulfate, and then concentrated under reduced pressure. The obtained crude product is purified by preparative thin layer chromatography, by which Compound 6 can be produced.

By using a procedure similar to that in the step (2) of the above scheme, morphinan derivatives having various structures represented by the general formula (I) in which A represents "—SO$_2$—" can be produced using Compound 5 synthesized in the step (1) of the above scheme 1 and any sulfonyl chloride having a desired structure.

Also, morphinan derivatives having various structures represented by the general formula (I), that is, compounds represented by the general formula (I) in which A represents "—C(═O)—" can be produced using, instead of benzenesulfonyl chloride, any acid chloride having a desired structure in the step (2) of the above scheme 1.

For example, N-[(4R,4aS,7R,7aR,12bS)-4a-hydroxy-9-methoxy-3-(phenylsulfonyl)-2,3,4,4a,5,6,7,7a-octahydro-1H-4,12-methanobenzofuro[3,2-e]isoquinolin-7-yl]-N-methylcinnamide (Compound 14), a compound represented by the general formula (I) in which A is "—SO$_2$—" and R$^8$ is "phenyl" out of the above basic skeletons (III), can be produced by the steps (1) to (4) of the reaction scheme 2 below.

Reaction scheme 2

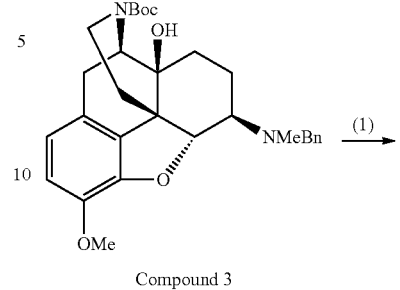

Compound 3

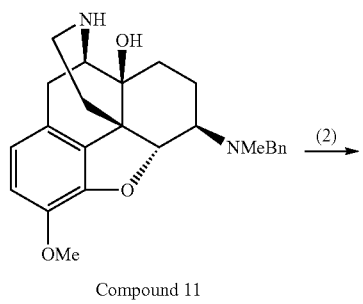

Compound 11

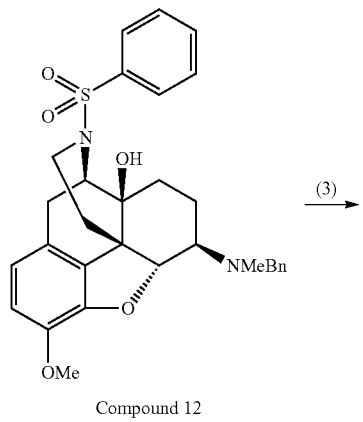

Compound 12

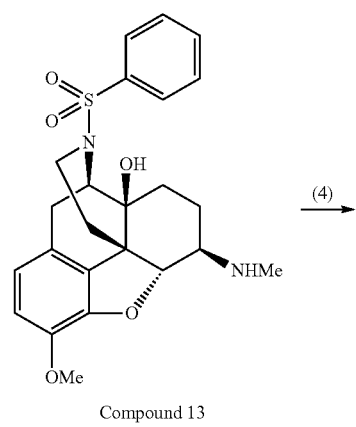

Compound 13

-continued

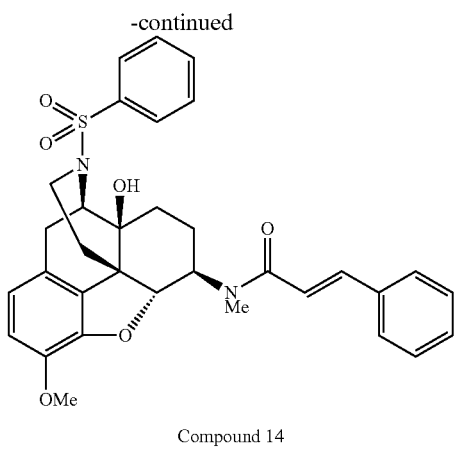

Compound 14

In the step (1) of the above scheme 2, Compound 3, which has been synthesized, for example, according to the method described in Chem. Pharm. Bull., Vol. 52, No. 6, pp. 670-674, 2004, is dissolved in hydrogen chloride-methanol under argon atmosphere, and the resulting mixture is stirred at room temperature for a predetermined time period. The reaction mixture is further stirred at a temperature around 50° C. for a predetermined time period, and then concentrated under reduced pressure. A saturated aqueous solution of sodium hydrogencarbonate is added to the residue, and the resulting mixture is extracted with 2-propanol/chloroform. The organic layer is washed with saturated brine, then dried over sodium sulfate, and concentrated under reduced pressure to purify the obtained crude product by silica gel chromatography, by which Compound 11 can be obtained.

In the step (2) of the above scheme 2, Compound 12 can be obtained by using the same method as that in the step (2) of the above reaction scheme 1, except that Compound 11 is used instead of Compound 5.

In the step (3) of the above scheme 2, Compound 12 obtained in the step (2) is dissolved in a solvent, such as THF, 5% palladium on activated carbon is added thereto, and the resulting mixture is stirred at room temperature for a predetermined time period under hydrogen atmosphere. Then, the reaction mixture is filtered through Celite, and the filtrate is concentrated under reduced pressure. The obtained crude product is again dissolved in a solvent, such as THF, 5% palladium on activated carbon is added thereto, and the resulting mixture is stirred at room temperature for a predetermined time period under hydrogen atmosphere. The reaction mixture is filtered through Celite, and the filtrate is concentrated under reduced pressure to purify the obtained crude product by silica gel chromatography, by which Compound 13 can be obtained.

In the step (4) of the above scheme 2, Compound 13 obtained in the step (3) is dissolved in a solvent, such as anhydrous dichloromethane, under argon atmosphere, and triethylamine is added thereto. To the obtained solution, cinnamoyl chloride is added on ice, and the resulting mixture is then stirred at room temperature for a predetermined time period. Then, the reaction mixture is diluted with a solvent, such as dichloromethane, and the resulting solution is washed with a saturated aqueous solution of sodium hydrogencarbonate and saturated brine, then dried over sodium sulfate, and concentrated under reduced pressure. The obtained crude product is purified by preparative thin layer chromatography, by which Compound 14 can be produced.

Also, in the step (4) of the above scheme 2, by using a procedure similar to that in the step (4), morphinan derivatives having various structures represented by the general formula (I) can be produced using Compound 13 and any acid chloride or isocyanate having a desired structure.

The pharmaceutically acceptable acid addition salt according to the present invention includes, but is not limited to, inorganic acid salts, such as hydrochloride, sulfate, nitrate, hydrobromide, hydroiodide, or phosphate; organic carboxylic acid salts, such as acetate, lactate, citrate, oxalate, glutarate, malate, tartrate, fumarate, mandelate, maleate, benzoate, or phthalate; or organic sulfonic acid salts, such as methanesulfonate, ethanesulfonate, benzenesulfonate, p-toluenesulfonate, or camphorsulfonate. Among those, acid addition salts such as, but not limited to, hydrochloride, hydrobromide, phosphate, tartrate, or methanesulfonate are preferably used.

The orexin receptor antagonist of the present invention is not particularly limited as long as it comprises, as an active ingredient, a morphinan derivative represented by the above general formula (I) or a pharmaceutically acceptable acid addition salt thereof, and has antagonism against orexin receptors. The orexin receptors are G protein-coupled receptors including two subtypes: OX1 receptor and OX2 receptor. Morphinan derivatives represented by the general formula (I) or pharmaceutically acceptable acid addition salts thereof, which are individually contained as an active ingredient in an orexin receptor antagonist of the present invention, may have antagonism against either OX1 receptor or OX2 receptor, or both of them; among those, a morphinan derivative which selectively binds to OX1 receptor and exerts antagonism against the receptor is preferable.

The antagonism against orexin receptors can be confirmed by, for example, measuring the change in intracellular calcium ion concentration in a competitive reaction between a test compound and OX-A and calculating the $IC_{50}$ value (50% maximal inhibitory concentration) from the concentration-response curve on the antagonist activity according to the method described in Test Example 1 below.

The $IC_{50}$ of the orexin receptor antagonist of the present invention against either OX1 receptor or OX2 receptor is usually not more than 100 μM, preferably not more than 10 μM, and further preferably not more than 1.0 μM. Among those, the $IC_{50}$ of the orexin receptor antagonist of the present invention against OX1 receptor is preferably not more than 1000 nM, further preferably not more than 700 nM, and particularly preferably not more than 300 nM.

A disease which can be treated or prevented by an orexin receptor antagonist of the present invention is such a disease that the onset of symptoms is promoted by the binding of the orexin ligand to orexin receptors, preferably OX1 receptor. Administration of the orexin receptor antagonist of the present invention to a patient results in competition between the above ligand and the drug of the present invention in the patient's body, in which the drug of the present invention exerts antagonistic effects on the orexin receptors-ligand binding and thereby improves the patient's condition. OX1 and OX2 receptors play important roles in the regulatory mechanism for feeding behavior and the maintenance mechanism for sleep and wakefulness, which are essential for life, and in control of energy metabolism and glucose metabolism. Accordingly, the diseases or symptoms which can be treated or prevented by the present invention can include, but are not particularly limited to, sleep disorder, obesity including obesity observed in diabetic patients, feeding disorder, anxiety disorder, depression, drug dependence, obsessive-compulsive disorder and attention deficit hyperactivity disorder (ADHD), and the like; the orexin receptor antagonist of the present invention is preferably used as a therapeutic and prophylactic agent for drug dependence.

Drug dependence targeted by the therapeutic or prophylactic agent of the present invention can include narcotic addiction, psychostimulant addiction, nicotine addiction, alcohol addiction, and central nervous system depressant addiction, and the like. Among those drugs causing the above-described addictions, the narcotics include morphine, heroin, cocaine, *cannabis*, and like; the psychostimulants include amphetamine, methamphetamine, and the like; the central nervous system depressants include barbiturates, benzodiazepines, and the like. The orexin receptor antagonist of the present invention is preferably for drug dependence caused by, among those, nicotine, alcohol, morphine, and cocaine.

The therapeutic and prophylactic effects of the orexin receptor antagonist of the present invention on drug dependence can be evaluated using an appropriate animal model. Examples of the evaluation include a method in which a withdrawal syndrome manifested after the administration of naloxone, an opioid receptor antagonist, is observed using a drug dependence model in which morphine, a narcotic for mice, is repeatedly administered to mice, according to the methods described in Test Examples 2 and 3 below.

Furthermore, other various diseases or symptoms related to orexin receptors can also be treated or prevented.

It is known that an orexin receptor antagonist is conventionally used as a therapeutic agent for sleep disorder such as insomnia, while a morphinan derivative represented by the general formula (I) or a pharmaceutically acceptable acid addition salt thereof in the present invention is also useful as an active ingredient in a therapeutic agent for sleep disorder.

The sleep disorder in the present invention refers to a disorder characterized by a chief complaint of sleeplessness, including, but not limited to, primary insomnia, secondary insomnia such as insomnia due to circadian rhythm sleep disorder, insomnia caused by depression, insomnia associated with other mental disorders, insomnia caused by stress, insomnia caused by physical disorders, and insomnia induced by a substance (such as, for example, alcohol, amphetamines, antianxiety agents, caffeine, cocaine, opioid, sedatives, and hypnotics). Symptoms of insomnia include sleep onset insomnia, sleep maintenance insomnia, sleep offset insomnia, and nonrestorative sleep.

As the orexin receptor antagonist of the present invention, a morphinan derivative represented by the general formula (I) or a pharmaceutically acceptable acid addition salt thereof can be administered in combination with one or more other agents conventionally used for the treatment or prevention of a disease or for alleviation or suppression of symptoms. The method of combining other agents may include sequential administration of each combined drug, or administration of a drug combination.

The morphinan derivative represented by the general formula (I) or a pharmaceutically acceptable acid addition salt is purified for pharmaceutical use to pass a required safety test, after which it can be administered directly as a pharmaceutical drug, or administered as a pharmaceutical composition comprising it in combination with a known pharmaceutically acceptable acid, carrier, excipient, or the like, orally or parenterally, to a mammal (for example, mouse, rat, hamster, rabbit, dog, monkey, cow, sheep, or human), preferably to a human. A dosage form for oral administration can be selected from, without limitation, dosage forms such as tablets, capsules, oral disintegrants, powders, granules, syrups, or jellies, while parenteral administration can be selected from, without limitation, intravenous bolus injection, continuous intravenous infusion, intramuscular injection, subcutaneous injection, intradermal injection, tapes, patch, and the like.

The content of a morphinan derivative represented by the general formula (I) or a pharmaceutically acceptable acid addition salt thereof in the pharmaceutical composition is not particularly limited, but, in the case of an oral drug, for example, it is prepared to usually have a content of 0.1 µg to 100 mg per dose. Moreover, the dose can be selected based on the condition, age, and body weight of a patient, and dosing regimen, and the like; however, the daily amount of a morphinan derivative represented by the general formula (I) or a pharmaceutically acceptable acid addition salt thereof for adult people is usually from 0.1 µg to 20 mg, preferably from 1 µg to 10 mg, and can be administered in one dose or in several divided doses.

EXAMPLES

The present invention will be specifically described below by way of Comparative Examples, Examples and Test Examples to demonstrate specific examples of the morphinan derivative represented by the general formula (I) and the pharmaceutically acceptable acid addition salt thereof, but the present invention is not limited thereto.

The abbreviations used in Comparative Examples and Examples below are commonly used abbreviations well known to those skilled in the art. Some of those abbreviations are shown below.

COMU: (1-cyano-2-ethoxy-2-oxoethylideneaminooxy)dimethylamino-morpholino-carbenium hexafluorophosphate DMF: N,N-dimethylformamide THF: tetrahydrofuran In proton nuclear magnetic resonance spectra, chemical shifts were referenced to tetramethylsilane and expressed in δ (ppm), while coupling constants were expressed in hertz (Hz). Coupling patterns are described as singlet (s), doublet (d), triplet (t), multiplet (m), and broad (br).

Moreover, the term "room temperature" in Comparative Examples and Examples refers to a temperature from about 10° C. to about 35° C., while the symbol "%" refers to percent by weight unless otherwise specified.

Comparative Example 1

Synthesis of (E)-N-[(4R,4aS,7R,7aR,12bS)-3-(cyclopropylmethyl)-4a,9-dihydroxy-2,3,4,4a,5,6,7,7a-octahydro-1H-4,12-methanobenzofuro[3,2-e]isoquinolin-7-yl]-3-(furan-3-yl)-N-methylacrylamide hydrochloride (Nalfurafine hydrochloride, Compound 1

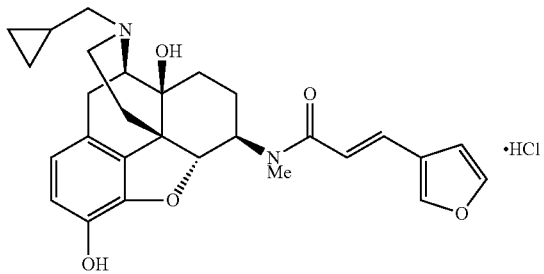

Compound 1

Compound 1 having the above indicated structure was synthesized according to the method described in Bioorg. Med. Chem. 2008, 16, 9188-9201.

Reference Example 1

Synthesis of (E)-N-[(4R,4aS,7R,7aR,12bS)-3-(cyclopropylmethyl)-4a-hydroxy-9-methoxy-2,3,4,4a,5,6,7,7a-octahydro-1H-4,12-methanobenzofuro[3,2-e]isoquinolin-7-yl]-3-(furan-3-yl)-N-methylacrylamide hydrochloride (Compound 2)

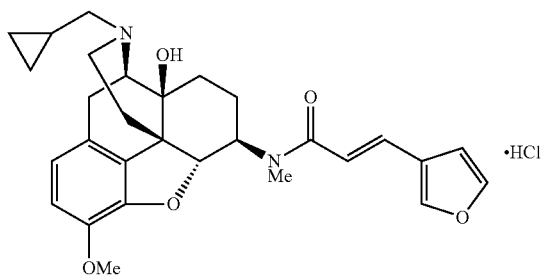

Compound 2

Under argon atmosphere, nalfurafine (200 mg, 0.42 mmol) was dissolved in anhydrous DMF (2.1 mL), and potassium carbonate (174 mg, 1.26 mmol) and iodomethane (31 μL, 0.498 mmol) were added thereto. The obtained solution was protected from light and stirred at room temperature for 18 hours, and the reaction mixture was then poured into water (6 mL), and extracted with diethylether. The organic layers were combined, washed sequentially with water and saturated brine, dried over magnesium sulfate, and then concentrated under reduced pressure. The obtained crude product was purified by silica gel chromatography (2-9% (v/v) methanol/chloroform) to give the free form of the title compound 2 (169 mg, 82%) as a colorless amorphous material. The compound was converted to a hydrochloride by using a hydrogen chloride-ethyl acetate solution and thereby the title compound 2 was obtained.

(Free-form)

$^1$H-NMR (400 MHz, CDCl$_3$) δ (ppm): 0.09-0.18 (m, 2H), 0.50-0.59 (m, 2H), 0.79-0.91 (m, 1H), 1.40-1.73 (m, 4H), 2.06-2.42 (m, 5H), 2.64 (dd, J=18.4, 5.6 Hz, 1H), 2.64-2.71 (m, 1H), 3.02 (s, 2.4H), 3.04 (s, 0.6H), 3.06-3.18 (m, 2H), 3.72-3.87 (m, 0.8H), 3.81 (s, 2.4H), 3.84 (s, 0.6H), 4.39-4.55 (s, 0.2H), 4.62 (d, J=8.4 Hz, 0.8H), 4.72 (d, J=8.4 Hz, 0.2H), 5.10 (brs, 1H), 6.44-6.64 (m, 2.2H), 6.67 (d, J=8.4 Hz, 0.8H), 6.72 (d, J=8.4 Hz, 0.2H), 6.80 (d, J=8.4 Hz, 0.8H), 7.36-7.62 (m, 3H). MS(ESI)[M+H]$^+$=491

(Hydrochloride)

mp(dec.): 235-240° C.

Elementary analysis: as C$_{29}$H$_{34}$N$_2$O$_5$.HCl.0.2H$_2$O

Calculated: C, 65.64; H, 6.72; N, 5.28.

Observed: C, 65.53; H, 6.97; N, 5.21.

Comparative Example 2

Synthesis of tert-butyl(4R,4aS,7R,7aR,12bS)-7-[benzyl(methyl)amino]-4a-hydroxy-9-methoxy-1,2,4,4a,5,6,7,7a-octahydro-3H-4,12-methanobenzofuro[3,2-e]isoquinolin-3-carboxylate (Compound 3)

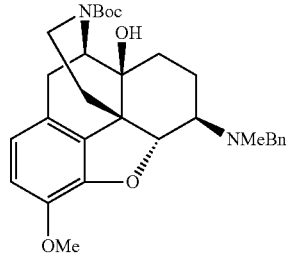

Compound 3

Compound 3 having the above indicated structure was synthesized according to the method described in Chem. Pharm. Bull., Vol. 52, No. 6, pp. 670-674, 2004.

Reference Example 2

Synthesis of tert-butyl(4R,4aS,7R,7aR,12bS)-7-[(E)-3-(furan-3-yl)-N-methylacrylamide]-4a-hydroxy-9-methoxy-1,2,4,4a,5,6,7,7a-octahydro-3H-4,12-methanobenzofuro[3,2-e]isoquinolin-3-carboxylate (Compound 4)

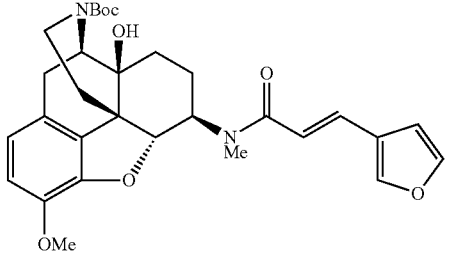

Compound 4

Compound 4 having the above indicated structure was synthesized according to the method described in Chem. Pharm. Bull., Vol. 52, No. 6, pp. 670-674, 2004.

Example 1

Synthesis of (E)-3-(furan-3-yl)-N-[(4R,4aS,7R,7aR,12bS)-4a-hydroxy-9-methoxy-3-(phenylsulfonyl)-2,3,4,4a,5,6,7,7a-octahydro-1H-4,12-methanobenzofuro[3,2-e]isoquinolin-7-yl]-N-methylacrylamide (Compound 6)

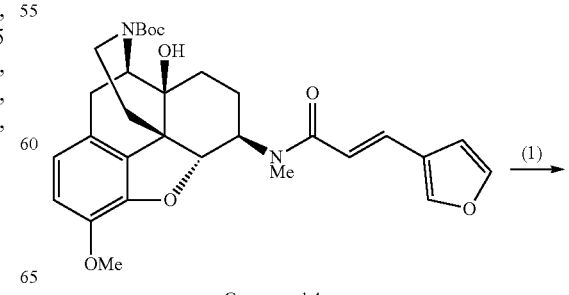

Compound 4

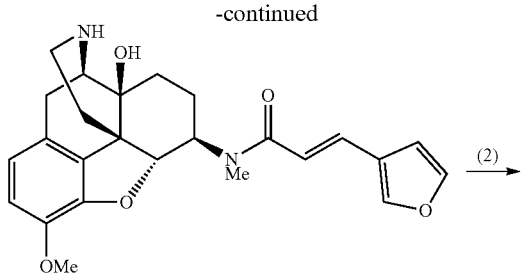

Compound 5

Compound 6

Step (1)

Synthesis of (E)-3-(furan-3-yl)-N-[(4R,4aS,7R,7aR,12bS)-4a-hydroxy-9-methoxy-2,3,4,4a,5,6,7,7a-octa-hydro-1H-4,12-methanobenzofuro[3,2-e]isoquinolin-7-yl]-N-methylacrylamide (Compound 5)

Under argon atmosphere, Compound 4 (960 mg, 0.179 mmol) was dissolved in 10% hydrogen chloride-methanol (10 mL), and the resulting mixture was stirred at room temperature for 25 hours. The reaction mixture was concentrated under reduced pressure, and a saturated aqueous solution of sodium hydrogencarbonate (50 mL) and potassium carbonate (1 g) were added to the residue, and subsequently the resulting mixture was extracted with 2-propanol/chloroform (1:3). The organic layer was washed with saturated brine, and then dried over sodium sulfate, and concentrated under reduced pressure. The obtained crude product was purified by silica gel chromatography (aqueous ammonia:methanol:chloroform=0:0:100→3:27:170) to give the title compound 5 (753 mg, 96%) as a pale yellow amorphous material.

$^1$H-NMR (400 MHz, CDCl$_3$) δ (ppm): 1.38-1.58 (m, 3H), 1.69-1.81 (m, 1H), 2.22-2.43 (m, 2H), 2.66-2.80 (m, 1.3H), 2.84 (dd, J=12.0, 4.4 Hz, 0.7H), 2.93-3.30 (m, 3.7H), 3.01 (s, 2.1H), 3.12 (s, 0.9H), 3.40-3.49 (m, 0.3H), 3.70-3.80 (m, 0.7H), 3.81 (s, 2.1H), 3.86 (s, 0.9H), 3.94-4.20 (m, 0.3H), 4.63 (d, J=8.0 Hz, 0.7H), 4.89 (d, J=8.0 Hz, 0.3H), 6.42-6.51 (m, 1.4H), 6.54-6.62 (m, 0.6H), 6.68 (d, J=8.4 Hz, 0.3H), 6.71 (d, J=8.4 Hz, 0.7H), 6.77 (d, J=8.4 Hz, 0.3H), 6.82 (d, J=8.4 Hz, 0.7H), 7.35-7.62 (m, 3H). No 1H(OH) was detected.
MS(ESI)[M+Na]$^+$=459

Step (2)

Synthesis of (E)-3-(furan-3-yl)-N-[(4R,4aS,7R,7aR,12bS)-4a-hydroxy-9-methoxy-3-(phenylsulfonyl)-2,3,4,4a,5,6,7,7a-octahydro-1H-4,12-methanobenzofuro[3,2-e]isoquinolin-7-yl]-N-methylacrylamide (Compound 6)

Under argon atmosphere, Compound 5 (30 mg, 0.0687 mmol) was dissolved in anhydrous dichloromethane (0.7 mL), and triethylamine (30 μL, 0.215 mmol) was added thereto. Benzenesulfonyl chloride (10.5 μL, 0.0823 mmol) was added to the obtained solution on ice, and then the resultant was stirred at room temperature for 2 hours. The reaction mixture was diluted with dichloromethane (5 mL), washed with a saturated aqueous solution of sodium hydrogencarbonate and saturated brine, then dried over sodium sulfate, and concentrated under reduced pressure. The obtained crude product was purified by preparative thin layer chromatography (methanol:chloroform=1:20) to give the title compound 6 (35.2 mg, 89%) as a colorless amorphous material.

$^1$H-NMR (400 MHz, CDCl$_3$) δ (ppm): 1.37-1.90 (m, 4H), 2.13-2.40 (m, 2H), 2.56 (d, J=18.4 Hz, 0.3H), 2.58 (d, J=18.4 Hz, 0.7H), 2.73 (ddd, J=12.4, 12.4, 3.6 Hz, 1H), 2.86 (dd, J=18.4, 5.2 Hz, 1H), 2.99 (s, 2.1H), 3.05 (s, 0.9H), 3.13 (s, 1H), 3.64-3.87 (m, 1.7H), 3.78 (s, 2.1H), 3.82 (s, 0.9H), 4.11-4.23 (m, 1H), 4.24-4.38 (m, 0.3H), 4.60 (d, J=8.0 Hz, 0.7H), 4.74 (d, J=8.0 Hz, 0.3H), 6.40 (d, J=14.8 Hz, 0.7H), 6.40-6.63 (m, 2.3H), 6.70 (d, J=8.4 Hz, 0.3H), 6.77 (d, J=8.4 Hz, 0.7H), 7.32-7.70 (m, 6H), 7.79-7.90 (m, 2H).
MS(ESI)[M+Na]$^+$=599

By using a procedure similar to that in the step (2) of Example 1, compounds of Examples 2-28 having structures indicated in the table below were synthesized using Compound 5 synthesized in the step (1) of Example 1 and any sulfonyl chloride having a desired structure. The $^1$H-NMR and MS data of each compound are shown in the table below.

TABLE 1

| Example | Structural formula | $^1$H-NMR and MS |
|---|---|---|
| 2 | | $^1$H-NMR (400 MHz, CDCl$_3$) δ (ppm): 1.38-1.82 (m, 4H), 2.13-2.37 (m, 2H), 2.64 (s, 3H), 2.84-3.17 (m, 7H), 3.60-3.89 (m, 1.7H), 3.80 (s, 2.1H), 3.84 (s, 0.9H), 3.94-4.04 (m, 1H), 4.19-4.37 (m, 0.3H), 4.60 (d, J = 8.0 Hz, 0.7H), 4.76 (d, J = 8.0 Hz, 0.3H), 6.37-6.49 (m, 1.4H), 6.53-6.63 (m, 0.9H), 6.66 (d, J = 8.4 Hz, 0.7H), 6.74 (d, J = 8.4 Hz, 0.3H), 6.82 (d, J = 8.4 Hz, 0.7H), 7.30-7.65 (m, 6H), 8.00 (d, J = 7.6 Hz, 1H). MS(ESI)[M + Na]$^+$ = 613 |

TABLE 1-continued

| Example | Structural formula | ¹H-NMR and MS |
|---|---|---|
| 3 | | ¹H-NMR (400 MHz, CDCl$_3$) δ (ppm): 1.38-1.81 (m, 4H), 2.13-2.38 (m, 2H), 2.45 (s, 3H), 2.59 (d, J = 18.4 Hz, 0.3H), 2.62 (d, J = 18.4 Hz, 0.7H), 2.73 (ddd, J = 12.8, 12.8, 3.6 Hz, 1H), 2.88 (dd, J = 18.4, 5.2 Hz, 1H), 3.01 (s, 3H), 3.14 (s, 1H), 3.63-3.88 (m, 1.7H), 3.79 (s, 2.1H), 3.83 (s, 0.9H), 4.11-4.20 (m, 1H), 4.25-4.43 (m, 0.3H), 4.60 (d, J = 7.6 Hz, 0.7H), 4.73 (d, J = 7.6 Hz, 0.3H), 6.35-6.65 (m, 3H), 6.70 (d, J = 8.4 Hz, 0.3H), 6.77 (d, J = 8.4 Hz, 0.7H), 7.34-7.69 (m, 7H). MS(ESI)[M + Na]⁺ = 613 |
| 4 | | ¹H-NMR (400 MHz, CDCl$_3$) δ (ppm): 1.37-1.77 (m, 4H), 2.13-2.37 (m, 2H), 2.46 (s, 3H), 2.01 (d, J = 18.4 Hz, 0.3H), 2.64 (d, J = 18.4 Hz, 0.7H), 2.72 (ddd, J = 12.8, 12.8, 3.6 Hz, 1H), 2.88 (dd, J = 18.4, 5.2 Hz, 1H), 2.97 (s, 2.1H), 3.04 (s, 0.9H), 3.14 (s, 1H), 3.62-3.85 (m, 1.7H), 3.78 (s, 2.1H), 3.82 (s, 0.9H), 4.11-4.20 (m, 1H), 4.24-4.39 (m, 0.3H), 4.60 (d, J = 8.0 Hz, 0.7H), 4.73 (d, J = 8.0 Hz, 0.3H), 6.41 (d, J = 15.2 Hz, 0.7H), 6.41-6.63 (m, 2.3H), 6.69 (d, J = 8.0 Hz, 0.3H), 6.77 (d, J = 8.0 Hz, 0.7H), 7.30-7.62 (m, 5H), 7.68-7.76 (m, 2H). MS(ESI)[M + Na]⁺ = 613 |
| 5 | | ¹H-NMR (400 MHz, CDCl$_3$) δ (ppm): 1.37-1.72 (m, 4H), 2.12-2.40 (m, 2H), 2.83-3.08 (m, 3H), 2.98 (s, 3H), 3.14 (s, 1H), 3.62-3.88 (m, 1.7H), 3.08 (s, 2.1H), 3.84 (s, 0.9H), 4.01-4.12 (m, 1H), 4.17-4.35 (m, 0.3H), 4.61 (d, J = 8.0 Hz, 0.7H), 4.77 (d, J = 8.0 Hz, 0.3H), 6.41 (d, J = 15.2 Hz, 0.7H), 6.42-6.50 (m, 0.7H), 6.53-6.63 (m, 0.9H), 6.66 (d, J = 8.0 Hz, 0.7H), 6.74 (d, J = 8.0 Hz, 0.3H), 6.82 (d, J = 8.0 Hz, 0.7H), 7.34-7.63 (m, 3H), 7.69-7.80 (m, 2H), 7.88-7.99 (m, 1H), 8.22-8.32 (m, 1H). MS(ESI)[M + Na]⁺ = 667 |
| 6 | | ¹H-NMR (400 MHz, CDCl$_3$) δ (ppm): 1.40-1.80 (m, 4H), 2.17-2.38 (m, 2H), 2.57-2.70 (m, 1H), 2.71-2.91 (m, 1.7H), 2.92-3.03 (m, 1.3H), 2.99 (s, 2.1H), 3.15 (s, 0.9H), 3.61-3.86 (m, 1.7H), 3.79 (s, 2.1H), 3.83 (s, 0.9H), 4.09-4.24 (m, 0.3H), 4.21 (d, J = 5.6 Hz, 1H), 4.61 (d, J = 8.0 Hz, 0.7H), 4.79 (d, J = 8.0 Hz, 0.3H), 6.40 (d, J = 15.2 Hz, 0.7H), 6.40-6.47 (m, 0.7H), 6.49-6.61 (m, 1.6H), 6.72 (d, J = 8.0 Hz, 0.3H), 6.79 (d, J = 8.0 Hz, 0.7H), 7.35-7.63 (m, 3H), 7.66-7.75 (m, 1H), 7.84-7.92 (m, 1H), 8.01-8.09 (m, 1H), 8.10-8.17 (m, 1H). MS(ESI)[M + Na]+ = 667 |

TABLE 1-continued

| Example | Structural formula | $^1$H-NMR and MS |
|---|---|---|
| 7 | | $^1$H-NMR (400 MHz, CDCl$_3$) δ (ppm): 1.39-1.85 (m, 4H), 2.15-2.40 (m, 2H), 2.58-2.72 (m, 1H), 2.80 (dddd, J = 13.2, 13.2, 13.2, 3.6 Hz, 1H), 2.88-3.10 (m, 2H), 2.99 (s, 2.1H), 3.15 (s, 0.9H), 3.61-3.81 (1.7H), 3.79 (s, 2.1H), 3.83 (s, 0.9H), 4.07-4.24 (0.3H), 4.22 (d, J = 4.8 Hz, 1H), 4.61 (d, J = 8.0 Hz, 0.7H), 4.78 (d, J = 8.0 Hz, 0.3H), 6.40 (d, J = 15.2 Hz, 0.7H), 6.40-6.47 (m, 0.7H), 6.49-6.63 (m, 1.6H), 6.72 (d, J = 8.4 Hz, 0.3H), 6.79 (d, J = 8.4 Hz, 0.7H), 7.32-7.64 (m, 3H), 7.76-7.87 (m, 2H), 7.94-8.05 (m, 2H). MS(ESI)[M + Na]+ = 667 |
| 8 | | $^1$H-NMR (400 MHz, CDCl$_3$) δ (ppm): 1.34-1.71 (m, 4H), 2.07-2.31 (m, 1H), 2.40 (ddd, J = 12.8, 12.8, 5.6 Hz, 1H), 2.91-3.05 (m, 1H), 2.96 (s, 2.1H), 3.06-3.26 (m, 3.9H), 3.70-3.80 (m, 1.7H), 3.81 (s, 2.1H), 3.85 (s, 0.9H), 3.95-4.01 (m, 1H), 4.19-4.36 (m, 0.3H), 4.60 (d, J = 7.6 Hz, 0.7H), 4.76 (d, J = 7.6 Hz, 0.3H), 6.41 (d, J = 15.2 Hz, 0.7H), 6.42-6.48 (m, 0.7H), 6.53-6.61 (m, 0.6H), 6.65 (d, J = 8.4 Hz, 0.3H), 6.71 (d, J = 8.4 Hz, 0.7H), 6.78 (d, J = 8.4 Hz, 0.3H), 6.85 (d, J = 8.4 Hz, 0.7H), 7.35-7.62 (m, 3H), 7.66-7.81 (m, 3H), 8.11-8.17 (m, 1H). MS(ESI)[M + Na]+ = 644 |
| 9 | | $^1$H-NMR (400 MHz, CDCl$_3$) δ (ppm): 1.39-1.78 (m, 4H), 2.18-2.40 (m, 2H), 2.72 (d, J = 18.4 Hz, 0.7H), 2.78 (d, J = 18.4 Hz, 0.3H), 2.79-3.24 (m, 3H), 2.98 (s, 2.1H), 3.16 (s, 0.9H), 3.61-3.87 (m, 1.7H), 3.78 (s, 2.1H), 3.84 (s, 0.9H), 3.91-4.07 (m, 0.3H), 4.22-4.30 (m, 1H), 4.61 (d, J = 7.6 Hz, 0.7H), 4.82 (d, J = 7.6 Hz, 0.3H), 6.38 (d, J = 15.6 Hz, 0.7H), 6.39-6.45 (m, 0.7H), 6.53-6.62 (m, 1.6H), 6.73 (d, J = 8.4 Hz, 0.3H), 6.80 (d, J = 8.4 Hz, 0.7H), 7.34-7.64 (m, 3H), 7.71-7.81 (m, 1H), 8.16-8.25 (m, 1H), 8.41-8.49 (m, 1H), 8.69-8.77 (m, 1H). MS(ESI)[M + Na]+ = 644 |
| 10 | | $^1$H-NMR (400 MHz, CDCl$_3$) δ (ppm): 1.38-1.78 (m, 4H), 2.17-2.40 (m, 2H), 2.69 (d, J = 18.4 Hz, 0.7H), 2.76 (d, 18.4 Hz, 0.3H), 2.76-3.28 (m, 3H), 2.97 (s, 2.1H), 3.16 (s, 0.9H), 3.61-3.89 (m, 1.7H), 3.78 (s, 2.1H), 3.84 (s, 0.9H), 3.90-4.09 (m, 0.3H), 4.20-4.28 (m, 1H), 4.61 (d, J = 7.6 Hz, 0.7H), 4.82 (d, J = 7.6 Hz, 0.3H), 6.38 (d, J = 15.6 Hz, 0.7), 6.33-6.47 (m, 0.7H), 6.52-6.64 (m, 1.6H), 6.73 (d, J = 8.4 Hz, 0.3H), 6.80 (d, J = 8.4 Hz, 0.7H), 7.32-7.65 (m, 3H), 8.02-8.12 (m, 2H), 8.32-8.42 (m, 2H). MS(ESI)[M + Na]+ = 644 |

TABLE 1-continued

| Example | Structural formula | $^1$H-NMR and MS |
|---|---|---|
| 11 | | $^1$H-NMR (400 MHz, CDCl$_3$) δ (ppm): 1.38-1.83 (m, 4H), 2.14-2.37 (m, 1H), 2.41 (ddd, J = 12.8, 12.8, 5.6 Hz, 1H), 2.72-2.87 (m, 1H), 2.88-3.03 (m, 1H), 2.98 (s, 2.1H), 3.04-3.20 (m, 2.9H), 3.62 (dd, J = 13.6, 4.8 Hz, 0.7H), 3.65-3.90 (m, 1H), 3.80 (s, 2.1H), 3.85 (s, 0.9H), 4.12-4.30 (m, 1.3H), 4.62 (d, J = 8.0 Hz, 0.7H), 4.79 (d, J = 8.0 Hz, 0.3H), 6.11 (d, J = 15.2 Hz, 0.7H), 6.42-6.48 (m, 0.7H), 6.53-6.61 (m, 0.6H), 6.63 (d, J = 8.0 Hz, 0.3H), 6.69 (d, J = 8.0 Hz, 0.7H), 6.75 (d, J = 8.0 Hz, 0.3H), 6.83 (d, J = 8.0 Hz, 0.7H), 7.32-7.63 (m, 3H), 7.67-7.83 (m, 2H), 7.86-7.96 (m, 1H), 8.12-8.20 (m, 1H). MS(ESI)[M + Na]+ = 624 |
| 12 | | $^1$H-NMR (400 MHz, CDCl$_3$) δ (ppm): 1.39-1.87 (m, 4H), 2.17-2.40 (m, 2H), 2.67 (d, J = 18.4 Hz, 0.7 Hz), 2.73 (d, J = 18.4 Hz, 0.3H), 2.74-2.91 (m, 1H), 2.93-3.21 (m, 2H), 2.98 (s, 2.1H), 3.16 (s, 0.9H), 3.58-3.90 (m, 1.7H), 3.79 (s, 2.1H), 3.84 (s, 0.9H), 3.95-4.13 (m, 0.3H), 4.22 (d, J = 5.2 Hz, 1H), 4.61 (d, J = 7.6 Hz, 0.7H), 4.81 (d, J = 7.6 Hz, 0.3H), 6.34-6.48 (m, 1.3H), 6.52-6.64 (m, 1.7H), 6.73 (d, J = 8.4 Hz, 0.3H), 6.81 (d, J = 8.4 Hz, 0.7H), 7.32-7.74 (m, 4H), 7.84-7.93 (m, 1H), 8.05-8.14 (m, 1H), 8.16-8.22 (m, 1H). MS(ESI)[M + Na]+ = 624 |
| 13 | | $^1$H-NMR (400 MHz, CDCl$_3$) δ (ppm): 1.40-1.85 (m, 4H), 2.17-2.40 (m, 2H), 2.64 (d, J = 18.0 Hz, 0.7H), 2.71 (d, J = 18.0 Hz, 0.3H), 2.75-3.05 (m, 3H), 2.98 (s, 2.1H), 3.16 (s, 0.9H), 3.59-3.89 (m, 1.7H), 3.79 (s, 2.1H), 3.84 (s, 0.9H), 3.93-4.10 (m, 0.3H), 4.20 (d, J = 5.6 Hz, 1H), 4.61 (d, J = 8.0 Hz, 0.7H), 4.80 (d, J = 8.0 Hz, 0.3H), 6.39 (d, J = 15.6 Hz, 0.7H), 6.39-6.46 (m, 0.7H), 6.53-6.62 (m, 1.6H), 6.73 (d, J = 8.0 Hz, 0.3H), 6.80 (d, J = 8.0 Hz, 0.7H), 7.35-7.65 (m, 3H), 7.80-7.88 (m, 2H), 7.93-8.03 (m, 2H). MS(ESI)[M + Na]+ = 624 |
| 14 | | $^1$H-NMR (400 MHz, CDCl$_3$) δ (ppm): 1.39-1.78 (m, 4H), 2.13-2.39 (m, 1H), 2.32 (ddd, J = 12.8, 12.8, 5.6 Hz, 1H), 2.80-2.96 (m, 3H), 2.97-2.38 (m, 1H), 2.99 (s, 2.1H), 3.13 (s, 0.9H), 3.67-3.86 (m, 1.7H), 3.81 (s, 2.1H), 3.84 (s, 0.9H), 4.12 (d, J = 5.2 Hz, 0.3H), 4.16 (d, J = 5.2 Hz, 0.7H), 4.22-4.36 (m, 0.3H), 4.61 (d, J = 8.0 Hz, 0.7H), 4.76 (d, J = 8.0 Hz, 0.3H), 6.42 (d, J = 15.6 Hz, 0.7H), 6.42-6.49 (m, 0.7H), 6.53-6.62 (m, 0.9H), 6.65 (d, J = 8.4 Hz, 0.7H), 6.74 (d, J = 8.4 Hz, 0.3H), 6.82 (d, J = 8.4 Hz, 0.7H), 7.19-7.69 (m, 6H), 7.89-7.98 (m, 1H). MS(ESI)[M + Na]+ = 617 |

TABLE 1-continued

| Example | Structural formula | ¹H-NMR and MS |
|---|---|---|
| 15 | | ¹H-NMR (400 MHz, CDCl$_3$) δ (ppm): 1.40-1.78 (m, 4H), 2.15-2.38 (m, 2H), 2.61 (d, J = 18.4 Hz, 1H), 2.71-2.84 (m, 1H), 2.84-2.98 (m, 2H), 2.99 (s, 2.1H), 3.14 (s, 0.9H), 3.64-3.86 (m, 1.7H), 3.79 (s, 2.1H), 3.83 (s, 0.9H), 4.17 (d, J = 5.2 Hz, 1H), 4.14-4.31 (m, 0.3H), 4.61 (d, J = 7.6 Hz, 0.7H), 4.76 (d, J = 7.6 Hz, 0.3H), 6.40 (d, J = 15.6 Hz, 0.7H), 6.41-6.46 (m, 0.7H), 6.50 (d, J = 8.4 Hz, 0.3H), 6.53-6.61 (m, 1.3H), 6.71 (d, J = 8.4 Hz, 0.3H), 6.79 (d, J = 8.4 Hz, 0.7H), 7.29-7.68 (m, 7H). <br> MS(ESI)[M + Na]+ = 617 |
| 16 | | ¹H-NMR (400 MHz, CDCl$_3$) δ (ppm): 1.40-1.78 (m, 4H), 2.15-2.37 (m, 2H), 2.61 (d, J = 18.4 Hz, 0.7H), 2.62 (d, J = 0.3H), 2.68-2.83 (m, 1H), 2.86-3.04 (m, 2H), 2.99 (s, 2.1H), 3.14 (s, 0.9H), 3.60-3.86 (m, 1.7H), 3.79 (s, 2.1H), 3.83 (s, 0.9H), 4.16 (d, J = 4.8 Hz, 1H), 4.13-4.32 (m, 0.3H), 4.60 (d, J = 8.0 Hz, 0.7H), 4.76 (d, J = 8.0 Hz, 0.3H), 6.40 (d, J = 15.2 Hz, 0.7H), 6.40-6.46 (m, 0.7H), 6.50 (d, J = 8.0 Hz, 0.3H), 6.53-6.61 (m, 1.3H), 6.71 (d, J = 8.0 Hz, 0.3H), 6.79 (d, J = 8.0 Hz, 0.7H), 7.18-7.29 (m, 2H), 7.33-7.63 (m, 3H), 7.82-7.91 (m, 2H). <br> MS(ESI)[M + Na]+ = 617 |
| 17 | | ¹H-NMR (400 MHz, CDCl$_3$) δ (ppm): 1.37-1.76 (m, 4H), 2.10-2.35 (m, 1H), 2.33 (ddd, J = 12.8, 12.8, 5.6 Hz, 1H), 2.89-3.24 (m, 7H), 3.69-3.80 (m, 0.7H), 3.73 (dd, J = 13.6, 4.8 Hz, 1H), 3.81 (s, 2.1H), 3.85 (0.9H), 3.90 (d, J = 4.8 Hz, 0.3H), 3.94 (d, J = 4.8 Hz, 0.7H), 4.25-4.41 (m, 0.3H), 4.61 (d, J = 8.0 Hz, 0.7H), 4.75 (d, J = 8.0 Hz, 0.3H), 6.42 (d, J = 15.2 Hz, 0.7H), 6.45-6.48 (m, 0.7H), 6.54-6.61 (m, 0.6H), 6.64 (d, J = 8.0 Hz, 0.3H), 6.71 (d, J = 8.0 Hz, 0.7H), 6.76 (d, J = 8.0 Hz, 0.3H), 6.84 (d, J = 8.0 Hz, 0.7H), 7.35-7.62 (m, 6H), 8.13-8.19 (m, 1H). <br> MS(ESI)[M + Na]+ = 633 |
| 18 | | ¹H-NMR (400 MHz, CDCl$_3$) δ (ppm): 1.40-1.83 (m, 4H), 2.15-2.38 (m, 2H), 2.63 (d, J = 18.4 Hz, 1H), 2.71-2.83 (m, 1H), 2.89-3.02 (m, 2H), 2.99 (s, 2.1H), 3.14 (s, 0.9H), 3.62-3.81 (m, 1.7H), 3.79 (s, 2.1H), 3.83 (s, 0.9H), 4.14-4.28 (m, 1.3H), 4.61 (d, J = 8.0 Hz, 0.7H), 4.77 (d, J = 8.0 Hz, 0.3H), 6.40 (d, J = 14.8 Hz, 0.7H), 6.41-6.47 (m, 0.7H), 6.52 (d, J = 8.4 Hz, 0.3H), 6.57 (d, J = 8.4 Hz, 0.7H), 6.57-6.62 (m, 0.6H), 6.72 (d, J = 8.4 Hz, 0.3H), 6.79 (d, J = 8.4 Hz, 0.7H), 7.34-7.63 (m, 5H), 7.68-7.76 (m, 1H), 7.82-7.87 (m, 1H) <br> MS(ESI)[M + Na]+ = 633 |

TABLE 1-continued

| Example | Structural formula | ¹H-NMR and MS |
|---|---|---|
| 19 | | ¹H-NMR (400 MHz, CDCl₃) δ (ppm): 1.40-1.77 (m, 4H), 2.15-2.37 (m, 2H), 2.63 (d, J = 18.4 Hz, 0.7H), 2.64 (d, J = 18.4 Hz, 0.3H), 2.69-2.82 (m, 1H), 2.88-3.04 (m, 2H), 2.99 (s, 2.1H) 3.14 (s, 0.9H), 3.60-3.87 (m, 1.7H), 3.79 (s, 2.1H), 3.83 (s, 0.9H), 4.12-4.28 (m, 1.3H), 4.60 (d, J = 8.0 Hz, 0.7H), 4.76 (d, J = 8.0 Hz, 0.3H), 6.40 (d, J = 15.6 Hz, 0.7H), 6.40-6.47 (m, 0.7H), 6.52 (d, J = 8.0 Hz, 0.3H), 6.54-6.61 (m, 1.3H), 6.72 (d, J = 8.0 Hz, 0.3H), 6.79 (d, J = 8.0 Hz, 0.7H), 7.34-7.63 (m, 5H), 7.75-7.83 (m, 2H). MS(ESI)[M + Na]+ = 633 |
| 20 | | ¹H-NMR (400 MHz, CDCl₃) δ (ppm): 1.37-1.68 (m, 4H), 2.08-2.40 (m, 1H), 2.35 (ddd, J = 12.8, 12.8, 4.8 Hz, 1H), 2.92-3.32 (m, 4.9H), 2.99 (s, 2.1H), 3.66-3.97 (m, 2.7H), 3.82 (s, 2.1H), 3.85 (s, 0.9H), 4.26-4.44 (m, 0.3H), 4.61 (d, J = 8.0 Hz, 0.7H), 4.75 (d, J = 8.0 Hz, 0.3H), 6.42 (d, J = 15.6 Hz, 0.7H), 6.42-6.50 (m, 0.7H), 6.53-6.61 (m, 0.6H), 6.65 (d, J = 8.4 Hz, 0.3H), 6.72 (d, J = 8.4 Hz, 0.7H), 6.76 (d, J = 8.4 Hz, 0.3H), 6.84 (d, J = 8.4 Hz, 0.7H), 7.33-7.63 (m, 5H), 7.75-7.86 (m, 1H), 8.21 (dd, J = 7.6, 1.6 Hz, 1H). MS(ESI)[M + Na]+ = 677 |
| 21 | | ¹H-NMR (400 MHz, CDCl₃) δ (ppm): 1.41-1.76 (m, 4H), 2.14-2.38 (m, 2H), 2.63 (d, J = 18.4 Hz, 0.7H), 2.64 (d, J = 18.4 Hz, 0.3H), 2.71-2.83 (m, 1H), 2.86-3.02 (m, 4.1H), 3.14 (s, 0.9H), 3.60-3.86 (m, 1.7H), 3.79 (s, 2.1H), 3.83 (s, 0.9H), 4.12-4.29 (m, 0.3H), 4.18 (d, J = 4.8 Hz, 1H), 4.61 (d, J = 7.6 Hz, 0.7H), 4.77 (d, J = 7.6 Hz, 0.3H), 6.40 (d, J = 14.8 Hz, 0.7H), 6.41-6.48 (m, 0.7H), 6.52 (d, J = 8.4 Hz, 0.7H), 6.54-6.62 (m, 1.3H), 6.72 (d, J = 8.4 Hz, 0.3H), 6.79 (d, J = 8.4 Hz, 0.7H), 7.34-7.63 (m, 4H), 7.71-7.81 (m, 2H), 7.97-8.02 (m, 1H). MS(ESI)[M + Na]+ = 677 |
| 22 | | ¹H-NMR (400 MHz, CDCl₃) δ (ppm): 1.40-1.80 (m, 4H), 2.15-2.37 (m, 2H), 2.64 (d, J = 18.4 Hz, 0.7H), 2.65 (d, J = 18.4 Hz, 0.3H), 2.69-2.84 (m, 1H), 2.88-3.05 (m, 2H), 2.99 (s, 2.1H), 3.14 (s, 0.9H), 3.60-3.86 (m, 1.7H), 3.79 (s, 2.1H), 3.83 (s, 0.9H), 4.11-4.27 (m, 0.3H), 4.17 (d, J = 5.2 Hz, 1H), 4.60 (d, J = 8.0 Hz, 0.7H), 4.76 (d, J = 8.0 Hz, 0.3H), 6.40 (d, J = 15.6 Hz, 0.7H), 6.41-6.46 (m, 0.7H), 6.50-6.62 (m, 1.6H), 6.72 (d, J = 8.4 Hz, 0.3H), 6.79 (d, J = 8.4 Hz, 0.7H), 7.34-7.64 (m, 3H), 7.65-7.76 (m, 4H). MS(ESI)[M + Na]+ = 677 |

TABLE 1-continued

| Example | Structural formula | ¹H-NMR and MS |
|---|---|---|
| 23 | | ¹H-NMR (400 MHz, CDCl₃) δ (ppm): 1.38-1.77 (m, 4H), 2.12-2.35 (m, 2H), 2.33 (s, 3H), 2.63 (s, 6H), 2.91 (ddd, 12.8, 12.8, 3.6 Hz, 1H), 2.87-3.06 (m, 1H), 2.98 (s, 2.1H), 3.07-3.34 (m, 2.9H), 3.47-3.58 (m, 1H), 3.71-3.90 (m, 1.7H), 3.81 (s, 2.1H), 3.85 (s, 0.9H), 4.22-4.37 (m, 0.3H), 4.59 (d, J = 7.6 Hz, 0.7H), 4.75 (d, J = 7.6 Hz, 0.3H), 6.43 (d, J = 15.2 Hz, 0.7H), 6.43-6.49 (m, 0.7H), 6.56-6.61 (m, 0.3H), 6.57 (d, J = 15.2 Hz, 0.3H), 6.64 (d, J = 8.0 Hz, 0.3H), 6.70 (d, J = 8.0 Hz, 0.7H), 6.76 (d, J = 8.0 Hz, 0.3H), 6.83 (d, J = 8.0 Hz, 0.7H), 6.96-7.02 (m, 2H), 7.34-7.62 (m, 3H). MS(ESI)[M + Na]+ = 641 |
| 24 | | ¹H-NMR (400 MHz, CDCl₃) δ (ppm): 1.34-1.71 (m, 4H), 2.07-2.28 (m, 2H), 2.87-3.11 (m, 4H), 2.91 (s, 0.9H), 2.94 (s, 2.1H), 3.59 (dd, J = 13.2, 4.8 Hz, 1H), 3.67-3.80 (m, 0.7H), 3.78 (s, 2.1H), 3.82 (s, 0.9H), 4.08-4.15 (m, 1H), 4.22-4.39 (m, 0.3H), 4.53 (d, J = 8.0 Hz, 0.7H), 4.69 (d, J = 8.0 Hz, 0.3H), 6.40 (d, J = 15.6 Hz, 0.7H), 6.40-6.45 (m, 0.7H), 6.51-6.60 (m, 0.9H), 6.61 (d, J = 8.4 Hz, 0.7H), 6.71 (d, J = 8.4 Hz, 0.3H), 6.79 (d, J = 8.4 Hz, 0.7H), 7.34-7.68 (m, 5H), 7.69-7.77 (m, 1H), 7.96-8.02 (m, 1H), 8.09-8.15 (m, 1H), 8.33 (d, J = 7.6 Hz, 1H), 8.52-8.59 (m, 1H). MS(ESI)[M + Na]+ = 649 |
| 25 | | ¹H-NMR (400 MHz, CDCl₃) δ (ppm): 1.40-1.51 (m, 2H), 1.51-1.64 (m, 1H), 1.70-1.87 (m, 1H), 2.03 (ddd, J = 12.8, 12.8, 5.2 Hz, 1H), 2.17-2.38 (m, 1H), 2.97 (s, 2.4H), 3.04 (ddd, J = 12.8, 12.8, 4.0 Hz, 1H), 3.10 (s, 0.6H), 3.18-3.34 (m, 2.2H), 3.39 (d, J = 18.4 Hz, 0.8H), 3.72-3.87 (m, 0.8H), 3.80 (s, 2.4H), 3.85 (s, 0.6H), 4.23-4.37 (m, 0.2H), 4.52 (d, J = 8.0 Hz, 0.8H), 4.59 (d, J = 4.8 Hz, 0.2H), 4.65 (d, J = 4.8 Hz, 0.8H), 4.70 (d, J = 0.2H), 5.35 (s, 0.2H), 5.56 (s, 0.8H), 6.44 (d, J = 15.6 Hz, 0.8H), 6.44-6.51 (m, 0.8H), 6.52-6.61 (m, 0.4H), 6.69 (d, J = 8.4 Hz, 0.2H), 6.73-6.81 (m, 1H), 6.85 (d, J = 8.4 Hz, 0.8H), 7.35-7.72 (m, 5H), 8.09-8.17 (m, 1H), 8.30-8.37 (m, 1H), 8.57-8.63 (m, 1H), 8.11 (dd, J = 4.4, 1.6 Hz, 1H). MS(ESI)[M + Na]+ = 650 |
| 26 | | ¹H-NMR (400 MHz, CDCl₃) δ (ppm): 1.40-1.74 (m, 4H), 2.16-2.33 (m, 2H), 2.93-3.24 (m, 12H), 3.50-3.60 (m, 1.3H), 3.68 (s, 0.7H), 3.72-3.88 (m, 0.7H), 3.81 (s, 2.1H), 3.85 (s, 0.9H), 4.02-4.14 (m, 1H), 4.05 (s, 0.9H), 4.06 (2.1H), 4.20-4.36 (m, 0.3H), 4.60 (d, J = 7.6 Hz, 0.7H), 4.78 (d, J = 7.6 Hz, 0.3H), 6.43 (d, 16.4 Hz, 0.7H), 6.43-6.48 (m, 0.7H), 6.54-6.61 (m, 0.6H), 6.65 (d, J = 8.0 Hz, 0.3H), 6.72 (d, J = 8.0 Hz, 0.7H), 6.77 (d, J = 8.0 Hz, 0.3H), 6.84 (d, J = 8.0 Hz, 0.7H), 7.14-7.21 (m, 1H), 7.36-7.66 (m, 7H), 7.79-7.85 (m, 1H), 8.20-8.24 (m, 1H). MS(ESI)[M + Na]+ = 796 |

TABLE 1-continued

| Example | Structural formula | $^1$H-NMR and MS |
|---|---|---|
| 27 | | $^1$H-NMR (400 MHz, CDCl$_3$) δ (ppm): 0.96 (t, J = 7.6 Hz, 3H), 1.37-1.92 (m, 8H), 2.18-2.45 (m, 2H), 2.84-3.28 (m, 6H), 3.00 (s, 2.1H), 3.17 (s, 0.9H), 3.52-3.69 (m, 1H), 3.70-3.91 (m, 0.7H), 3.82 (s, 2.1H), 3.86 (s, 0.9H), 3.99-4.17 (m, 1.3H), 4.64 (d, J = 7.6 Hz, 0.7H), 4.83 (d, J = 7.6 Hz, 0.3H), 6.42-6.91 (m, 0.7H), 6.43 (d, J = 15.2 Hz, 0.7H), 6.54-6.62 (m, 0.6H), 6.67 (d, J = 8.4 Hz, 0.3H), 6.74 (d, J = 8.4 Hz, 0.7H), 6.77 (d, J = 8.4 Hz, 0.3H), 6.86 (d, J = 8.4 Hz, 0.7H), 7.32-7.67 (m, 3H). MS(ESI)[M + Na]+ = 579 |
| 28 | | $^1$H-NMR (400 MHz, CDCl$_3$) δ (ppm): 0.98-1.13 (m, 2H), 1.16-1.30 (m, 2H), 1.39-1.78 (m, 4H), 2.15-2.54 (m, 3H), 2.87-2.98 (m, 1H), 3.01 (s, 2.1H), 3.09-3.27 (m, 3H), 3.16 (s, 0.9H), 3.58-3.69 (m, 1H), 3.72-3.91 (m, 0.7H), 3.82 (s, 2.1H), 3.86 (s, 0.9H), 4.10 (d, J = 5.2 Hz, 1H), 4.19-4.35 (m, J = 0.3H), 4.63 (d, J = 8.4 Hz, 0.7H), 4.78 (d, J = 8.4 Hz, 0.3H), 6.43 (d, J = 15.6 Hz, 0.7H), 6.43-6.50 (m, 0.7H), 6.55-6.70 (m, 0.9H), 6.74 (d, J = 8.4 Hz, 0.7H), 6.77 (d, J = 8.4 Hz, 0.3H), 6.86 (d, J = 8.4 Hz, 0.7H), 7.34-7.67 (m, 3H). MS(ESI)[M + Na]+ = 563 |

Example 29

Synthesis of 3-({(4R,4aS,7R,7aR,12bS)-7-[(E)-3-(furan-3-yl)-N-methylacrylamide]-4a-hydroxy-9-methoxy-1,2,4,4a,5,6,7,7a-octahydro-3H-4,12-methanobenzofuro[3,2-e]isoquinolin-3-yl}sulfonyl)-N,N-dimethylbenzamide (Compound 7)

Compound 7

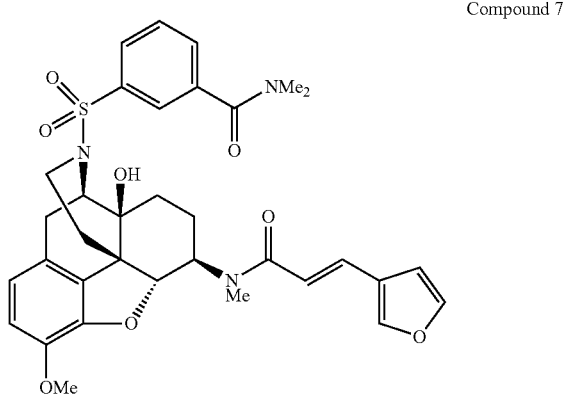 [SMILES: COc1ccc2c3c1O[C@H]1[C@H](N(C)C(=O)/C=C/c4ccoc4)CC[C@@]4(O)[C@@H](C2)N(S(=O)(=O)c2cccc(C(=O)N(C)C)c2)CC[C@]314]

Under argon atmosphere, Compound 5 (30 mg, 0.0687 mmol) was dissolved in anhydrous dichloromethane (0.7 mL), and triethylamine (30 μL, 0.215 mmol) was added thereto. To the obtained solution, 3-(chlorosulfonyl)benzoic acid (10.5 μL, 0.0823 mmol) was added on ice, and the resulting mixture was then stirred at room temperature for 2 hours. The reaction solution was supplemented with anhydrous DMF (0.7 mL), and COMU (38.4 mg, 0.0897 mmol) was added thereto on ice. After 5 minutes, dimethylamine hydrochloride (7.8 mg, 0.0957 mmol) was added to the reaction solution, and stirred at room temperature for 26 hours. The reaction mixture was poured into 1 M hydrochloric acid (5 mL), and extracted with ethyl acetate. The organic layer was washed with a saturated aqueous solution of sodium hydrogencarbonate and saturated brine, then dried over sodium sulfate, and concentrated under reduced pressure. The obtained crude product was purified by preparative thin layer chromatography (methanol:chloroform=1:20) to give the title compound 7 (35.3 mg, 79%) as a pale brown amorphous material.

$^1$H-NMR (400 MHz, CDCl$_3$) δ (ppm): 1.39-1.76 (m, 4H), 2.13-2.38 (m, 2H), 2.65 (d, J=18.4 Hz, 1H), 2.70-2.82 (m, 1H), 2.93 (dd, J=18.4, 5.2 Hz, 1H), 2.93-3.19 (m, 1H), 2.99 (s, 5.1H), 3.14 (s, 3.9H), 3.63-3.85 (m, 1.7H), 3.78 (s, 2.1H), 3.82 (s, 0.9H), 4.10-4.31 (m, 0.3H), 4.17 (d, J=5.2 Hz, 1H), 4.60 (d, J=8.0 Hz, 0.7H), 4.75 (d, J=8.0 Hz, 0.3H), 6.40 (d, J=15.2 Hz, 0.7H), 6.40-6.46 (m, 0.7H), 6.49 (d, J=8.4 Hz, 0.3H), 6.53-6.61 (m, 0.6H), 6.55 (d, J=8.4 Hz, 0.7H), 6.70 (d, J=8.4 Hz, 0.3H), 6.78 (d, J=8.4 Hz, 0.7H), 7.34-7.72 (m, 5H), 7.85-7.95 (m, 2H).

MS(ESI)[M+Na]$^+$=670

Example 30

Synthesis of (E)-N-[(4R,4aS,7R,7aR,12bS)-3-{[2-(dimethylamino) phenyl]sulfonyl}-4a-hydroxy-9-methoxy-2,3,4,4a,5,6,7,7a-octahydro-1H-4,12-methanobenzofuro[3,2-e]isoquinolin-7-yl]-3-(furan-3-yl)-N-methylacrylamide (Compound 8)

Compound 8

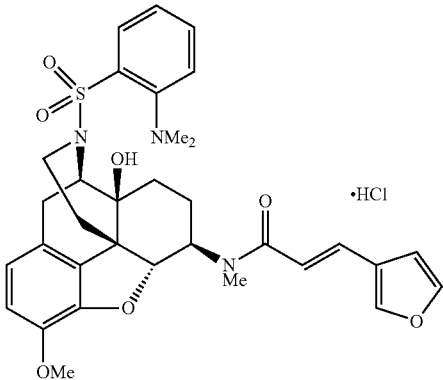

Under argon atmosphere, (E)-3-(furan-3-yl)-N-{(4R,4aS,7R,7aR,12bS)-4a-hydroxy-9-methoxy-3-[(2-nitrophenyl)sulfonyl]-2,3,4,4a,5,6,7,7a-octahydro-1H-4,12-methanobenzofuro[3,2-e]isoquinolin-7-yl}-N-methylacrylamide (105.6 mg, 0.170 mmol) was dissolved in dichloromethane (3 mL) and ethanol (3 mL), and concentrated hydrochloric acid (120 μL) was added thereto. The obtained solution was heated to 40° C. with stirring, and tin(II) chloride (800 mg, 4.22 mmol) was then added thereto and stirred for 2 hours. A saturated aqueous solution of sodium hydrogencarbonate (20 mL) was added to the reaction mixture to adjust pH to 9, and subsequently precipitates were filtered through Celite. The solids on the Celite were rinsed with chloroform (100 mL), the organic layer was separated, and the aqueous layer was then extracted with chloroform. The organic layers were combined, dried over sodium sulfate, and concentrated under reduced pressure. The obtained crude product was dissolved in acetic acid (8 mL), and paraformaldehyde (153 mg) and sodium cyanoborohydride (106.8 mg, 1.7 mmol) were added thereto. The obtained reaction liquid was stirred at 40° C. for 3 hours under argon atmosphere, and then concentrated under reduced pressure. A saturated aqueous solution of sodium hydrogencarbonate was added to the residue to adjust pH to 9, and the resulting mixture was extracted with chloroform. The organic layer was washed with saturated brine, dried over sodium sulfate, and then concentrated under reduced pressure. The resulting liquid was purified by preparative thin layer chromatography (aqueous ammonia:methanol:chloroform=1:9:400) to give the free form of the title compound (74.6 mg, 71%) as a yellow oily material. The compound was converted to a hydrochloride by using a hydrogen chloride-methanol solution and thereby the title compound 8 was obtained.

(Free-form)
$^1$H-NMR (400 MHz, CDCl$_3$) δ (ppm): 1.20-1.33 (m, 0.7H), 1.36-1.58 (m, 3.3H), 1.58-1.75 (m, 1H), 2.03-2.37 (m, 2H), 2.75-3.24 (m, 6H), 2.84 (s, 4.2H), 3.00 (s, 1.8H), 3.71-3.86 (m, 0.7H), 3.80 (s, 2.1H), 3.84 (s, 0.9H), 4.10-4.24 (m, 1H), 4.25-4.40 (m, 0.3H), 4.58 (d, J=8.0 Hz, 0.7H), 4.68-4.81 (m, 0.6H), 4.91-5.01 (m, 0.7H), 6.39-6.88 (m, 4H), 7.15-7.67 (m, 6H), 8.07-8.19 (m, 1H).
MS(ESI)[M+H]$^+$=620
(Hydrochloride)
mp(dec.): 129-130° C.
Elementary analysis: as C$_{33}$H$_{37}$N$_3$O$_7$S.HCl.2H$_2$O
Calculated: C, 57.26; H, 6.12; N, 6.07.
Observed: C, 57.04; H, 6.06; N, 5.98.

Example 31 and Example 32

By a procedure similar to that in Example 30, compounds having structures indicated in Table 2 below were synthesized using, as a starting material, (E)-3-(furan-3-yl)-N-{(4R,4aS,7R,7aR,12bS)-4a-hydroxy-9-methoxy-3-[(3-nitrophenyl)sulfonyl]-2,3,4,4a,5,6,7,7a-octahydro-1H-4,12-methanobenzofuro[3,2-e]isoquinolin-7-yl}-N-methylacrylamide (Example 31) or (E)-3-(furan-3-yl)-N-{(4R,4aS,7R,7aR,12bS)-4a-hydroxy-9-methoxy-3-[(4-nitrophenyl)sulfonyl]-2,3,4,4a,5,6,7,7a-octahydro-1H-4,12-methanobenzofuro[3,2-e]isoquinolin-7-yl}-N-methylacrylamide (Example 32).

TABLE 2

| Example | Structural formula | $^1$H-NMR, MS and Elementary analysis |
|---|---|---|
| 31 | | (Free-form) $^1$H-NMR (400 MHz, CDCl$_3$) δ (ppm): 1.37-1.80 (m, 5H), 2.12-2.37 (m, 2H), 2.61-2.93 (m, 3H), 2.94-3.15 (m, 4H), 2.99 (s, 1.8H), 3.02 (s, 4.2H), 3.63-3.85 (m, 0.7H), 3.79 (s, 2.1H), 3.83 (s, 0.9H), 4.08-4.21 (m, 1H), 4.26-4.45 (m, 0.3H), 4.60 (d, J = 7.6 Hz, 0.7H), 4.72 (d, J = 7.6 Hz, 0.3H), 6.35-6.61 (m, 3H), 6.70 (d, J = 8.4 Hz, 0.3H), 6.78 (d, J = 8.4 Hz, 0.7H), 6.83-6.95 (m, 1H), 7.02-7.15 (m, 2H), 7.32-7.65 (m, 4H). MS(ESI)[M + Na]+ = 642 mp(dec.): 130-131° C. (Hydrochloride) Elementary analysis: as C33H37N3O7S · HCl · H2O Calculated: C, 58.79; H, 5.98; N, 6.23. Observed: C, 58.92; H, 5.74; N, 6.13. |

TABLE 2-continued

| Example | Structural formula | $^1$H-NMR, MS and Elementary analysis |
|---|---|---|
| 32 | | (Free-form)<br>$^1$H-NMR (400 MHz, CDCl$_3$) δ (ppm): 1.38-1.82 (m, 5H), 2.14-2.36 (m, 2H), 2.64-2.92 (m, 3H), 2.97-3.21 (m, 3H), 2.99 (s, 1.8H), 3.08 (s, 4.2H), 3.57-3.67 (m, 1H), 3.68-3.85 (m, 0.7H), 3.79 (s, 2.1H), 3.82 (s, 0.9H), 4.06-4.17 (m, 1H), 4.25-4.46 (m, 0.3H), 4.59 (d, J = 8.0 Hz, 0.7H), 4.71 (d, J = 8.0 Hz, 0.3H), 6.38-6.74 (m, 5.3H), 6.77 (d, J = 8.4 Hz, 0.7H), 7.32-7.69 (m, 5H).<br>MS(ESI)M + Na]+ = 642<br>(Hydrochloride)<br>mp(dec.): 147-148° C.<br>Elementary analysis as C$_{33}$H$_{37}$N$_3$O · S · HCl<br>Calculated: C, 60.04; H, 5.84; N, 6.40.<br>Observed: C, 60.70; H, 5.91; N, 6.27. |

Example 33

Synthesis of (4R,4aS,7R,7aR,12bS)-7-[(E)-3-(furan-3-yl)-N-methylacrylamide]-4a-hydroxy-9-methoxy-N-phenyl-1,2,4,4a,5,6,7,7a-octahydro-3H-4,12-methanobenzofuro[3,2-e]isoquinolin-3-carboxamide (Compound 9)

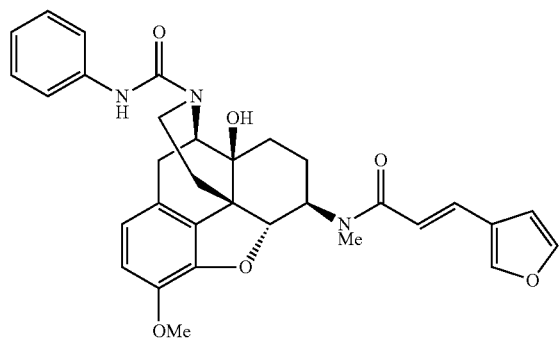

Compound 9

The synthesis of the title compound was performed by the same method as in Example 1 except that phenyl isocyanate was used instead of benzenesulfonyl chloride in the step (2), and thereby the title compound 9 (32.6 mg, 85%) was obtained as a colorless solid.

$^1$H-NMR (400 MHz, CDCl$_3$) δ (ppm): 1.40-1.79 (m, 4H), 2.18-2.35 (m, 1H), 2.40 (ddd, J=12.8, 12.8, 5.6 Hz, 1H), 2.90-3.26 (m, 3H), 3.00 (s, 2.1H), 3.16 (s, 0.9H), 3.23 (s, 0.7H), 3.36 (brs, 0.3H), 3.59-3.72 (m, 1H), 3.73-3.89 (m, 0.7H), 3.82 (s, 2.1H), 3.86 (s, 0.9H), 4.13-4.30 (m, 0.3H), 4.50 (d, J=5.2 Hz, 0.3H), 4.58 (d, J=5.2 Hz, 0.7H), 4.64 (d, J=7.6 Hz, 0.7H), 4.81 (d, J=7.6 Hz, 0.3H), 6.40-6.50 (m, 1.4H), 6.54-6.62 (m, 0.6H), 6.62-6.75 (m, 2H), 6.78 (d, J=8.4 Hz, 0.3H), 6.85 (d, J=8.4 Hz, 0.7H), 7.01-7.10 (m, 1H), 7.25-7.62 (m, 7H).

MS(ESI)[M+Na]$^+$=578

Compounds of Examples 34-36 having structures indicated in the table below were synthesized by the same method as in Example 1 except that any acid chloride having a desired structure was used instead of benzenesulfonyl chloride in the step (2). The $^1$H-NMR and MS data of each compound are shown in the table below.

TABLE 3

| Example | Structural formula | $^1$H-NMR and MS |
|---|---|---|
| 34 | | $^1$H-NMR (400 MHz, CDCl$_3$) δ (ppm): 0.72-0.92 (m, 2H), 0.93-1.18 (m, 2H), 1.38-2.01 (m, 5H), 2.10-2.66 (m, 2H), 2.76-3.34 (m, 7H), 3.61-3.95 (m, 3.9H), 3.96-4.13 (m, 0.7H), 4.17-4.54- (m, 0.7H), 4.59-4.72 (m, 0.7H), 4.74-4.88 (m, 0.3H), 4.88-5.04 (m, 0.7H), 6.41-6.53 (m, 1.4H), 6.55-6.91 (m, 2.6H), 7.36-7.67 (m, 3H).<br>MS(ESI)[M + Na]$^+$ = 527 |

TABLE 3-continued

| Example | Structural formula | ¹H-NMR and MS |
|---|---|---|
| 35 | | ¹H-NMR (400 MHz, CDCl₃) δ (ppm): 1.23-1.75 (m, 4H), 1.86-2.12 (brs, 1H), 2.17-2.75 (m, 2H), 2.38 (s, 3H), 2.84-3.37 (m, 6H), 3.42-3.68 (m, 1H), 3.68-3.91 (m, 3.7H), 3.93-4.19 (m, 0.3H), 4.24-4.83 (m, 1.4H), 4.97-5.12 (m, 0.6H), 6.37-6.90 (m, 4H), 7.15-7.26 (m, 2H), 7.29-7.66 (m, 5H). MS(ESI)[M + Na]⁺ = 577 |
| 36 | | ¹H-NMR (400 MHz, CDCl₃) δ (ppm): 1.39-1.88 (m, 4H), 2.04 (brs, 1H), 2.18-2.54 (m, 2H), 2.61-2.73 (m, 0.2H), 2.86-3.27 (m, 6H), 3.44-3.61 (m, 0.2H), 3.72-3.95 (m, 4.6H), 4.15-4.40 (m, 0.4H), 4.43-4.55 (m, 0.2H), 4.56-4.73 (m, 0.2H), 4.66 (d, J = 7.6 Hz, 0.4H), 4.80 (d, J = 7.6 Hz, 0.2H), 5.03-5.14 (m, 0.6H), 6.39-7.07 (m, 5H), 7.31-7.70 (m, 9H). MS(ESI)[M + Na]⁺ = 589 |

Example 37

Synthesis of (E)-3-(furan-3-yl)-N-[(4R,4aS,7R,7aR,12bS)-4a-hydroxy-9-methoxy-3-(quinoline-6-carbonyl)-2,3,4,4a,5,6,7,7a-octahydro-1H-4,12-methanobenzofuro[3,2-e]isoquinolin-7-yl]-N-methylacrylamide (Compound 10)

Compound 10

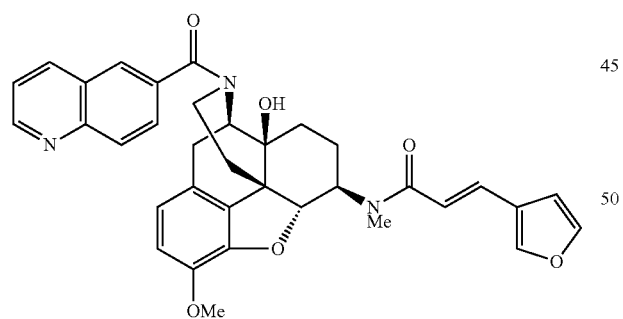

Under argon atmosphere, 6-quinolinecarboxylic acid (14.3 mg, 0.0825 mmol) was suspended in anhydrous DMF (0.4 mL), and N,N-diisopropylethylamine (36 μL, 0.207 mmol) and COMU (36 mg, 0.0841 mmol) were added to the obtained solution on ice, and the resulting mixture was then stirred. After 5 minutes, a solution of Compound 5 (30 mg, 0.0687 mmol) in anhydrous DMF (0.4 mL) was added thereto, and the resulting solution was stirred at room temperature for 19 hours. The reaction mixture was poured into a saturated aqueous solution of sodium hydrogencarbonate (5 mL), and extracted with ethyl acetate. The organic layer was washed with water and saturated brine, dried over sodium sulfate, and then concentrated under reduced pressure. The obtained crude product was purified by preparative thin layer chromatography (methanol:chloroform=1:20) to give the title compound 10 (35.5 mg, 87%) as a colorless amorphous material.

¹H-NMR (400 MHz, CDCl₃) δ (ppm): 1.24-1.79 (m, 4H), 2.01-2.51 (m, 3H), 2.68-2.85 (m, 0.2H), 2.86-3.19 (m, 5.2H), 3.25 (dd, J=18.4, 5.6 Hz, 0.6H), 3.47-3.68 (m, 1H), 3.68-3.92 (m, 3.6H), 3.99-4.10 (m, 0.2H), 4.18-4.70 (m, 1.2H), 4.74-4.88 (m, 0.3H), 5.14 (d, J=3.6 Hz, 0.7H), 6.34-6.90 (m, 4H), 7.33-7.64 (m, 4H), 7.76 (d, J=8.4 Hz, 0.7H), 7.83-8.09 (m, 1.3H), 8.09-8.23 (m, 2H), 8.92-9.01 (m, 1H).

MS(ESI)[M+Na]⁺=614

Example 38

Synthesis of N-[(4R,4aS,7R,7aR,12bS)-4a-hydroxy-9-methoxy-3-(phenylsulfonyl)-2,3,4,4a,5,6,7,7a-octahydro-1H-4,12-methanobenzofuro[3,2-e]isoquinolin-7-yl]-N-methylcinnamide (Compound 14)

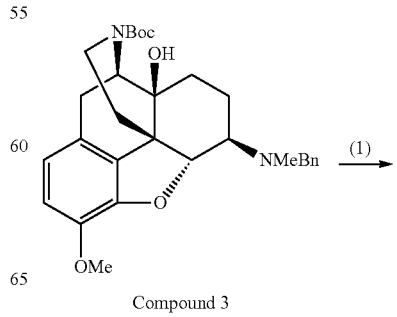

Compound 3

-continued

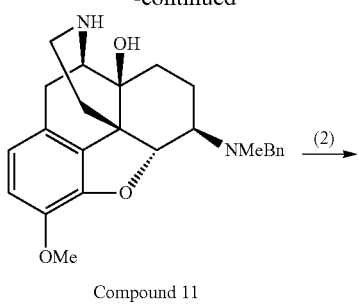

Compound 11

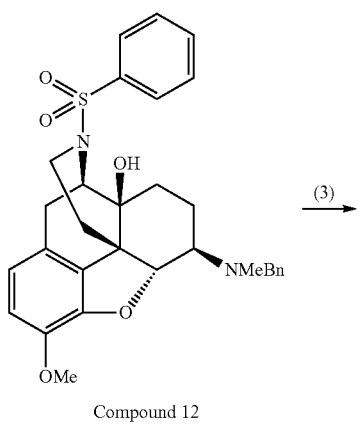

Compound 12

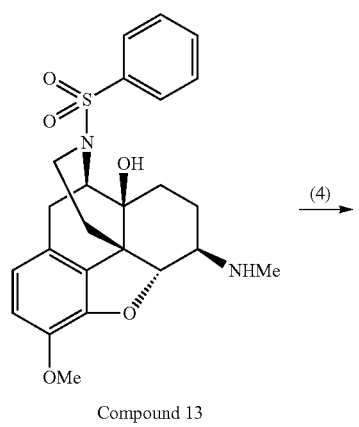

Compound 13

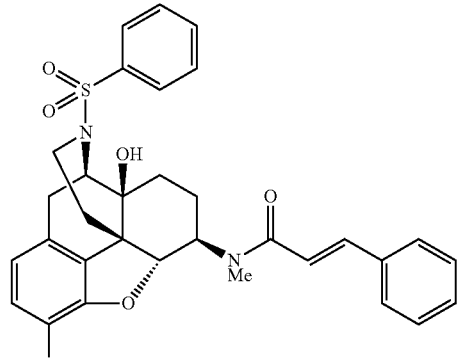

Compound 14

Step (1)

Synthesis of (4R,4aS,7R,7aR,12bS)-7-[benzyl (methyl) amino]-9-methoxy-1,2,3,4,5,6,7,7a-octahydro-4aH-4,12-methanobenzofuro[3,2-e]isoquinolin-4a-ol (Compound 11)

Under argon atmosphere, Compound 3 (1.92 g, 3.79 mmol) was dissolved in 10% hydrogen chloride-methanol (10 mL), and the resulting mixture was stirred at room temperature for 37 hours. The reaction mixture was further stirred at 50° C. for 7 hours, and then concentrated under reduced pressure. A saturated aqueous solution of sodium hydrogencarbonate (20 mL) was added to the residue, and subsequently the resulting mixture was extracted with 2-propanol/chloroform (1:3). The organic layer was washed with saturated brine, and then dried over sodium sulfate, and concentrated under reduced pressure. The obtained crude product was purified by silica gel chromatography (aqueous ammonia:methanol:chloroform=0:0:100→3:27:170) to give the title compound 11 (1.53 g, 99%) as a colorless amorphous material.

$^1$H-NMR (400 MHz, CDCl$_3$) δ (ppm): 1.36 (ddd, J=13.6, 11.6, 4.0 Hz, 1H), 1.44-1.59 (m, 2H), 1.68 (ddd, J=13.6, 4.0, 4.0 Hz, 1H), 1.90-2.04 (m, 1H), 2.27-2.38 (m, 1H), 2.32 (s, 3H), 2.60 (ddd, J=11.6, 6.8, 4.4 Hz, 1H), 2.74 (ddd, J=12.8, 12.8, 4.0 Hz, 1H), 2.90 (dd, J=12.8, 4.0 Hz, 1H), 3.08 (dd, J=18.4, 5.6 Hz, 1H), 3.14 (d, J=18.4 Hz, 1H), 3.37 (d, J=4.0 Hz, 1H), 3.70 (d, J=14.0 Hz, 1H), 3.77 (d, J=14.0 Hz, 1H), 3.88 (s, 3H), 4.76 (d, J=6.8 Hz, 1H), 6.61 (d, J=8.4 Hz, 1H), 6.72 (d, J=8.4 Hz, 1H), 7.16-7.24 (m, 1H), 7.25-7.32 (m, 2H), 7.33-7.40 (m, 2H). No 2H(NH, OH) was detected.
MS(ESI)[M+H]$^+$=407

Step (2)

Synthesis of (4R,4aS,7R,7aR,12bS)-7-[benzyl (methyl) amino]-9-methoxy-3-(phenylsulfonyl)-1,2,3,4,5,6,7,7a-octahydro-4aH-4,12-methanobenzofuro [3,2-e]isoquinolin-4a-ol (Compound 12)

The same method as in Example 3 was performed except that Compound 11 (1.5 g, 3.69 mmol) was used instead of Compound 5 in the step (2), and thereby the title compound 12 (1.8 g, 89%) was obtained.

$^1$H-NMR (400 MHz, CDCl$_3$) δ (ppm): 1.32 (ddd, J=12.8, 12.8, 3.2 Hz, 1H), 1.48-1.59 (m, 2H), 1.64 (ddd, J=12.8, 4.0, 4.0 Hz, 1H), 1.98 (dddd, 12.8, 12.8, 12.8, 3.2 Hz, 1H), 2.24 (ddd, J=12.8, 12.8, 5.6 Hz, 1H), 2.33 (s, 3H), 2.51-2.64 (m, 2H), 2.75 (ddd, J=12.8, 12.8, 3.2 Hz, 1H), 2.84 (dd, J=18.4, 5.6 Hz, 1H), 3.20 (brs, 1H), 3.60-3.72 (m, 2H), 3.76 (d, J=14.0 Hz, 1H), 3.85 (s, 3H), 4.14 (d, J=5.6 Hz, 1H), 4.72 (d, J=6.8 Hz, 1H), 6.41 (d, J=8.4 Hz, 1H), 6.65 (d, J=8.4 Hz, 1H), 7.17-7.23 (m, 1H), 7.23-7.31 (m, 2H), 7.31-7.39 (m, 2H), 7.51-7.58 (m, 2H), 7.58-7.65 (m, 1H), 7.80-7.90 (m, 2H).
MS(ESI)[M+H]$^+$=547

Step (3)

Synthesis of (4R,4aS,7R,7aR,12bS)-9-methoxy-7-(methylamino)-3-(phenylsulfonyl)-1,2,3,4,5,6,7,7a-octahydro-4aH-4,12-methanobenzofuro[3,2-e]isoquinolin-4a-ol (Compound 13)

Compound 12 (1.35 g, 2.47 mmol) was dissolved in THF (13.5 mL), 5% palladium on activated carbon (Degussa type) (330 mg) was added thereto, and the resulting mixture was stirred at room temperature for 47 hours under hydrogen atmosphere. The reaction mixture was filtered through Celite, and the filtrate was concentrated under reduced pressure. The obtained crude product was again dissolved in THF (13.5 mL), 5% palladium on activated carbon (Degussa type) (500 mg) was added thereto, and the resulting mixture was stirred at room temperature for 37.5 hours under hydrogen atmosphere. The reaction mixture was filtered through Celite, and the filtrate was concentrated under reduced pressure. The obtained crude product was purified by silica gel chromatography (aqueous ammonia:methanol:chloroform=1:9:95→3:27:170) to give the title compound 13 (913 mg, 81%) as a colorless solid.

$^1$H-NMR (400 MHz, CDCl$_3$) δ (ppm): 1.30-1.42 (m, 1H), 1.46-1.59 (m, 2H), 1.61-1.77 (m, 2H), 2.30 (ddd, J=12.8, 12.8, 5.6 Hz, 1H), 2.44 (s, 3H), 2.54 (ddd, J=9.2, 4.4, 4.4 Hz, 1H), 2.65 (d, J=18.4 Hz, 1H), 2.80 (ddd, J=12.8, 12.8, 4.0 Hz, 1H), 2.92 (dd, J=18.4, 5.6 Hz, 1H), 3.62 (dd, J=12.8, 5.6 Hz, 1H), 3.85 (s, 3H), 4.22 (d, J=5.6 Hz, 1H), 4.39 (d, J=5.6 Hz, 1H), 6.48 (d, J=8.0 Hz, 1H), 6.70 (d, J=8.0 Hz, 1H), 7.47-7.65 (m, 3H), 7.81-7.93 (m, 2H). No 2H(NH, OH) was detected.

MS(ESI)[M+H]$^+$=457

Step (4)

Synthesis of N-[(4R,4aS,7R,7aR,12bS)-4a-hydroxy-9-methoxy-3-(phenylsulfonyl)-2,3,4,4a,5,6,7,7a-octahydro-1H-4,12-methanobenzofuro[3,2-e]isoquinolin-7-yl]-N-methylcinnamide (Compound 14)

Under argon atmosphere, Compound 13 (20 mg, 0.0438 mmol) was dissolved in anhydrous dichloromethane (440 μL), and triethylamine (18.5 μL, 0.133 mmol) was added thereto. To the obtained solution, cinnamoyl chloride (9.2 mg, 0.0552 mmol) was added on ice, and the resulting mixture was then stirred at room temperature for 2 hours. The reaction mixture was diluted with dichloromethane (5 mL), washed with a saturated aqueous solution of sodium hydrogencarbonate and saturated brine, then dried over sodium sulfate, and concentrated under reduced pressure. The obtained crude product was purified by preparative thin layer chromatography (acetone:n-hexane=1:1) to give the title compound 14 (20 mg, 78%) as a colorless amorphous material.

$^1$H-NMR (400 MHz, CDCl$_3$) δ (ppm): 1.38-1.80 (m, 4H), 2.14-2.40 (m, 2H), 2.57 (d, J=18.4 Hz, 0.3H), 2.58 (d, J=18.4 Hz, 0.7H), 2.68-2.80 (m, 1H), 2.88 (dd, J=18.4, 5.6 Hz, 1H), 2.93-3.09 (m, 1H), 3.01 (s, 2.1H), 3.16 (s, 0.9H), 3.64-3.90 (m, 1.70H), 3.71 (s, 2.1H), 3.83 (s, 0.9H) 4.11-4.23 (m, 1H), 4.23-4.40 (m, 0.3H), 4.62 (d, J=8.0 Hz, 0.7H), 4.76 (d, J=8.0 Hz, 0.3H), 6.46 (d, J=8.0 Hz, 0.3H), 6.52 (d, J=8.0 Hz, 0.7H), 6.68 (d, J=15.2 Hz, 0.7H), 6.70 (d, J=8.4 Hz, 0.3H), 6.75 (d, J=8.4H, 0.7H), 6.86 (d, J=15.2 Hz, 0.3H), 7.24-7.43 (m, 4H), 7.48-7.71 (m, 5H), 7.79-7.90 (m, 2H).

MS(ESI)[M+Na]$^+$=609

Example 39 and Example 40

By a procedure similar to that in the step (4) of Example 38, compounds having structures indicated in Table 4 below were synthesized using Compound 13 and any acid chloride having a desired structure.

TABLE 4

| Example | Structural formula | $^1$H-NMR and MS |
|---|---|---|
| 39 | | $^1$H-NMR (400 MHz, CDCl$_3$) δ (ppm): 1.20-1.68 (m, 4H), 2.06-2.41 (m, 3H), 2.51-3.00 (m, 10H), 3.48 (ddd, J = 12.8, 8.0, 4.4 Hz, 0.7H), 3.63-3.73 (m, 1H), 3.64 (s, 2.1H), 3.82 (s, 0.9H), 4.13 (d, J = 5.6 Hz, 1H), 4.21-4.35 (m, 0.3H), 4.56 (d, J = 8.0 Hz, 0.7H), 4.66 (d, J = 8.0 Hz, 0.3H), 6.45 (d, J = 8.4 Hz, 0.3H), 6.49 (d, J = 8.4 Hz, 0.7H), 6.65 (d, J = 8.4 Hz, 0.7H), 6.69 (d, J = 8.4 Hz, 0.3H), 7.00-7.04 (m, 1H), 7.10-7.23 (m, 3H), 7.25-7.31 (m, 1H), 7.52-7.59 (m, 2H), 7.60-7.67 (m, 1H), 7.81-7.86 (m, 2H). MS(ESI)[M + Na]$^+$ = 611 |
| 40 | | $^1$H-NMR (400 MHz, CDCl$_3$) δ (ppm): 0.67-0.79 (m, 0.7H), 0.85-0.96 (m, 0.7H), 1.34-1.67 (m, 2.4H), 1.97 (dddd, J = 12.8, 12.8, 12.8, 2.8 Hz, 0.7H), 2.05-2.20 (m, 0.3H), 2.24 (ddd, J = 12.8, 12.8, 5.6 Hz, 1H), 2.55 (d, J = 18.4 Hz, 0.3H), 2.56 (d, J = 18.4 Hz, 0.7H), 2.72 (ddd, J = 12.8, 12.8, 3.6 Hz, 1H), 2.78-2.93 (m, 2H), 2.88 (s, 2.1H), 2.96 (s, 0.9H), 3.49-3.58 (m, 1.3H), 3.63-3.76 (m, 2.3H), 3.83 (s, 0.9H), 3.86-3.93 (m, 0.3H), 3.88 (s, 2.1H), 4.07 (d, J = 5.6 Hz, 0.7H), 4.13 (d, J = 5.6 Hz, 0.3H), 4.20-4.38 (m, 0.3H), 4.56 (d, J = 8.0 Hz, 0.7H), 4.66 (d, J = 8.0 Hz, 0.3H), 6.44 (d, J = 8.4 Hz, 0.3H), 6.59 (d, J = 8.4 Hz, 0.7H), 6.69 (d, J = 8.4 Hz, 0.3H), 6.72-6.78 (m, 1H), 6.82 (d, J = 8.4 Hz, 0.7H), 7.07-7.13 (m, 2H), 7.20-7.35 (m, 2H), 7.51-7.67 (m, 3H), 7.79-7.87 (m, 2H). MS(ESI)[M + Na]$^+$ = 597 |

Example 41 and Example 42

By a procedure similar to that in the step (4) of Example 38, compounds having structures indicated in Table 5 below were synthesized using Compound 13 and any isocyanate having a desired structure.

TABLE 5

| Example | Structural formula | $^1$H-NMR and MS |
|---|---|---|
| 41 | | $^1$H-NMR (400 MHz, CDCl$_3$) δ (ppm): 1.34-1.47 (m, 1H), 1.49-1.62 (m, 2H), 1.70 (ddd, J = 13.2, 3.2, 3.2 Hz, 1H), 2.25-2.39 (m, 2H), 2.58 (d, J = 18.4 Hz, 1H), 2.74 (ddd, J = 13.2, 13.2, 3.6 Hz, 1H), 2.86 (dd, J = 18.4, 5.6 Hz, 1H), 2.92-3.00 (m, 1H), 2.95 (s, 3H), 3.67-3.77 (m, 2H), 3.82 (s, 3H), 4.16 (d, J = 5.2 Hz, 1H), 4.66 (d, J = 7.6 Hz, 1H), 6.52 (d, J = 8.4 Hz, 1H), 6.72 (d, J = 8.4 Hz, 1H), 6.94-7.04 (m, 1H), 7.12 (brs, 1H), 7.21-7.28 (m, 2H), 7.29-7.34 (m, 2H), 7.52-7.61 (m, 2H), 7.61-7.69 (m, 1H), 7.79-7.89 (m, 2H). MS(ESI)[M + Na]$^+$ = 598 |
| 42 | | $^1$H-NMR (400 MHz, CDCl$_3$) δ (ppm): 1.41 (ddd, J = 12.8, 12.8, 3.2 Hz, 1H), 1.43-1.53 (m, 1H), 1.56 (dd, J = 12.8, 2.8 Hz, 1H), 1.67 (ddd, J = 12.8, 2.8, 2.8 Hz, 1H), 2.14-2.28 (m, 1H), 2.26 (ddd, J = 12.8, 12.8, 5.6 Hz, 1H), 2.58 (d, J = 18.4 Hz, 1H), 2.73 (ddd, J = 12.8, 12.8, 4.0 Hz, 1H), 2.82-2.92 (m, 1H), 2.88 (s, 3H), 3.60 (s, 3H), 3.65-3.77 (m, 2H), 4.15 (d, J = 5.6 Hz, 1H), 4.33 (dd, J = 15.2, 6.4 Hz, 1H), 4.40 (dd, J = 15.2, 5.6 Hz, 1H), 4.61 (d, J = 8.0 Hz, 1H), 5.27 (brs, 1H), 6.49 (d, J = 8.4 Hz, 1H), 6.64 (d, J = 8.4 Hz, 1H), 7.18-7.33 (m, 5H), 7.51-7.66 (m, 3H), 7.79-7.89 (m, 2H). No 1H(OH) was detected. MS(ESI)[M + Na]$^+$ = 612 |

Example 43

Synthesis of N-[(4R,4aS,7R,7aR,12bS)-4a-hydroxy-9-methoxy-3-(phenylsulfonyl)-2,3,4,4a,5,6,7,7a-octahydro-1H-4,12-methanobenzofuro[3,2-e]isoquinolin-7-yl]-N-methyl-N'-phenylsulfamide (Compound 15)

Compound 15

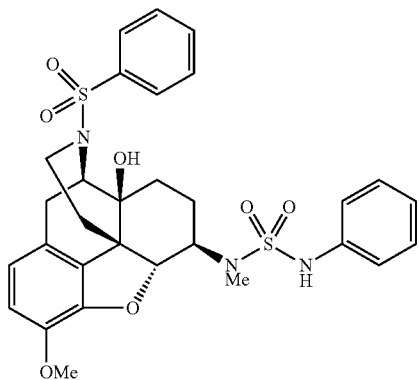

Under argon atmosphere, anhydrous benzene (5.8 mL) and phosphorus pentachloride (120 mg, 0.577 mmol) were added to N-phenylsulfamic acid (100 mg, 0.577 mmol), and the resulting mixture was heated for 24 hours under reflux. The obtained solution was allowed to cool, and then precipitated solids were removed by filtration, and the filtrate was concentrated under reduced pressure. Under argon atmosphere, to a solution of the obtained crude product (79 mg) in anhydrous dichloromethane (880 μL), a mixed solution of Compound 21 (20 mg, 0.0438 mmol) and triethylamine (115 μL, 0.824 mmol) in anhydrous dichloromethane (440 μL) was added on ice. The obtained solution was stirred at room temperature for 20 hours, and triethylamine (115 μL, 0.824 mmol) was then added thereto, and the resulting mixture was further stirred for 20 hours. The reaction mixture was diluted with dichloromethane (5 mL), washed with a saturated aqueous solution of sodium hydrogencarbonate and saturated brine, then dried over sodium sulfate, and concentrated under reduced pressure. The obtained crude product was purified by preparative thin layer chromatography (acetone:n-hexane=2:3, followed by methanol:chloroform=1:40) to give the title compound 15 (19.5 mg, 73%) as a colorless amorphous material.

$^1$H-NMR (400 MHz, CDCl$_3$) δ (ppm): 1.38-1.54 (m, 2H), 1.62 (dd, J=12.8, 2.8 Hz, 1H), 1.69 (ddd, J=12.8 Hz, 2.8, 2.8 Hz, 1H), 2.08 (dddd, J=12.8, 12.8, 12.8, 2.8 Hz, 1H), 2.29 (ddd, J=12.8, 12.8, 5.6 Hz, 1H), 2.53 (d, J=18.4 Hz, 1H), 2.70-2.92 (m, 2H), 2.79 (s, 3H), 2.90 (s, 1H), 3.71-3.85 (m, 2H), 3.83 (s, 3H), 4.14 (d, J=5.6 Hz, 1H), 4.64 (d, J=8.0 Hz, 1H), 6.52 (d, J=8.4 Hz, 1H), 6.74 (d, J=8.4 Hz, 1H), 7.09-7.19 (m, 1H), 7.28-7.35 (m, 2H), 7.40-7.47 (m, 2H), 7.52-7.61 (m, 2H), 7.61-7.68 (m, 1H), 7.80-7.88 (m, 2H). No 1H(OH) was detected.

MS(ESI)[M+Na]⁺=634

Example 44

Synthesis of (E)-3-(furan-3-yl)-N-[(4R,7R,7aR,12bS)-9-methoxy-3-(phenylsulfonyl)-2,3,4,6,7,7a-hexahydro-1H-4,12-methanobenzofuro[3,2-e]isoquinolin-7-yl]-N-methylacrylamide (Compound 18)

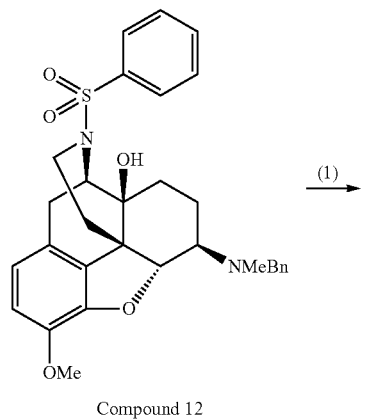

Compound 12

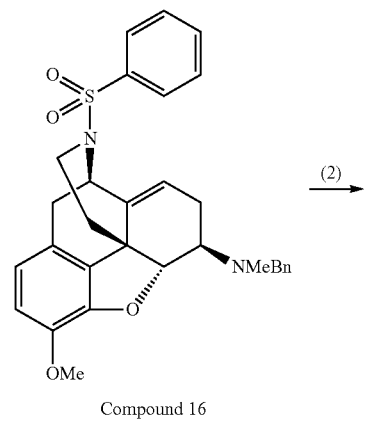

Compound 16

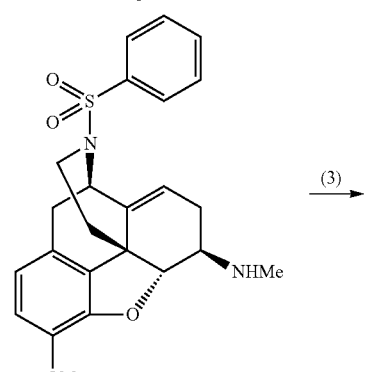

Compound 17

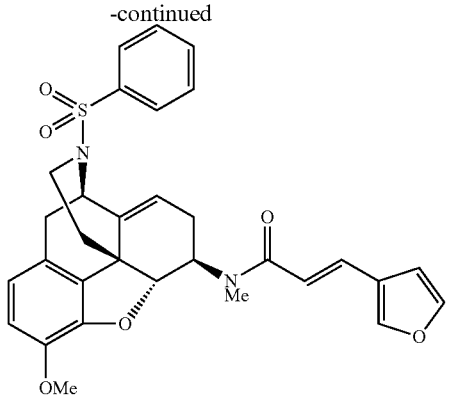

Compound 18

Step (1)

Synthesis of (4R,7R,7aR,12bS)-N-benzyl-9-methoxy-N-methyl-3-(phenylsulfonyl)-2,3,4,6,7,7a-hexahydro-1H-4,12-methanobenzofuro[3,2-e]isoquinolin-7-amine (Compound 16)

Under argon atmosphere, Compound 12 (163 mg, 0.298 mmol) was dissolved in anhydrous pyridine (6 mL), and thionyl chloride (220 μL, 3.02 mmol) was added thereto with stirring on ice. The obtained solution was stirred for 30 minutes on ice and then for 6 hours at room temperature. A saturated aqueous solution of sodium hydrogencarbonate (20 mL) was slowly added to the reaction mixture on ice, and potassium carbonate (2 g) was then added thereto, and the resulting mixture was extracted with ethyl acetate. The organic layer was washed with saturated brine, and then dried over sodium sulfate, and concentrated under reduced pressure. The obtained crude product was purified by silica gel chromatography (0-3% (v/v) methanol/chloroform) to give the title compound 16 (115 mg, 73%) as a colorless amorphous material.

¹H-NMR (400 MHz, CDCl₃) δ (ppm): 1.64 (ddd, J=12.8, 12.8, 5.2 Hz, 1H), 1.76-1.84 (m, 1H), 1.93-2.10 (m, 2H), 2.34 (s, 3H), 2.67 (ddd, J=10.4, 10.4, 5.2 Hz, 1H), 2.79 (d, J=18.0 Hz, 1H), 2.95 (dd, J=18.0, 6.8 Hz, 1H), 3.16 (ddd, J=12.8, 12.8, 2.8 Hz, 1H), 3.66-3.87 (m, 3H), 3.89 (s, 3H), 4.74 (d, J=9.6 Hz, 1H), 4.87 (d, J=6.8 Hz, 1H), 5.52-5.58 (m, 1H), 6.49 (d, J=8.4 Hz, 1H), 6.68 (d, J=8.4 Hz, 1H), 7.11-7.37 (m, 5H), 7.47-7.62 (m, 3H), 7.81-7.88 (m, 2H).

MS(ESI)[M+H]⁺=529

Step (2)

Synthesis of (4R,7R,7aR,12bS)-9-methoxy-N-methyl-3-(phenylsulfonyl)-2,3,4,6,7,7a-hexahydro-1H-4,12-methanobenzofuro[3,2-e]isoquinolin-7-amine (Compound 17)

Compound 16 (71 mg, 0.134 mmol) was dissolved in methanol (4 mL), and 5% palladium on activated carbon (Degussa type) (75 mg) was added thereto. The obtained solution was stirred at room temperature for 13 hours under hydrogen atmosphere. The reaction mixture was filtered through Celite, and the filtrate was concentrated under reduced pressure. The obtained crude product was purified by silica gel chromatography (aqueous ammonia:methanol:chloroform=1:9:95→1:9:30) to give the title compound 17 (53.7 mg, 86%) as a pale brown amorphous material.

¹H-NMR (400 MHz, CDCl₃) δ (ppm): 1.69 (ddd, J=12.8, 12.8, 5.2 Hz, 1H), 1.79 (ddd, J=12.8, 3.6, 1.6 Hz, 1H), 2.00 (ddd, J=16.0, 11.6, 1.6 Hz, 1H), 2.41 (ddd, J=16.0, 6.8, 5.2 Hz, 1H), 2.53-2.68 (m, 1H), 2.57 (s, 3H), 2.91 (d, J=18.4 Hz, 1H), 3.00 (dd, J=18.4, 6.8 Hz, 1H), 3.12-3.24 (m, 1H), 3.69-3.77 (m, 1H), 3.83 (s, 3H), 4.63 (d, J=9.2 Hz, 1H), 4.91 (d, J=6.8 Hz, 1H), 5.52 (dd, J=6.8, 1.6 Hz, 1H), 6.55 (d, J=8.4 Hz, 1H), 6.69 (d, J=8.4 Hz, 1H), 7.46-7.52 (m, 2H), 7.53-7.59 (m, 1H) 7.80-7.87 (m, 2H). No 1H(NH) was detected.

MS(ESI)[M+H]⁺=439

Step (3)

Synthesis of (E)-3-(furan-3-yl)-N-[(4R,7R,7aR,12bS)-9-methoxy-3-(phenylsulfonyl)-2,3,4,6,7,7a-hexahydro-1H-4,12-methanobenzofuro[3,2-e]isoquinolin-7-yl]-N-methylacrylamide (Compound 18)

The same method as in Example 38 was performed except that Compound 17 (20 mg, 0.0456 mmol) was used instead of Compound 13 in the step (4), and thereby the title compound 18 (20.9 mg, 82%) was obtained.

¹H-NMR (400 MHz, CDCl₃) δ (ppm): 1.62-1.92 (m, 2H), 2.01 (ddd, J=16.4, 6.8, 4.8 Hz, 1H), 2.22-2.55 (m, 1H), 2.76-3.16 (m, 2H), 2.96 (s, 1.8H), 3.12 (s, 1.2H), 3.18 (ddd, J=12.8, 12.8, 3.2 Hz, 1H), 3.64-3.89 (m, 1.6H), 3.69 (s, 1.8H), 3.80 (s, 1.2H), 3.93-4.20 (m, 0.4H), 4.59 (d, J=10.0 Hz, 0.6H), 4.92 (d, J=6.4 Hz, 0.4H), 4.96 (J=7.2 Hz, 1H), 5.58 (d, J=6.4 Hz, 0.4H), 5.62 (d, J=6.4 Hz, 0.6H), 6.10-6.18 (m, 1H), 6.50-6.65 (m, 2H), 6.68 (d, J=8.4 Hz, 0.4H), 6.75 (d, J=8.4 Hz, 0.6H), 7.31-7.65 (m, 6H), 7.82-7.90 (m, 2H).

MS(ESI)[M+Na]⁺=581

Example 45

Synthesis of (E)-N-[(4R,4aS,7R,7aR,12bS)-3-{[2-(dimethylamino) phenyl]sulfonyl}-4a-hydroxy-9-methoxy-2,3,4,4a,5,6,7,7a-octahydro-1H-4,12-methanobenzofuro[3,2-e]isoquinolin-7-yl]-N-methyl-3-(pyridin-2-yl)acrylamide (Compound 25)

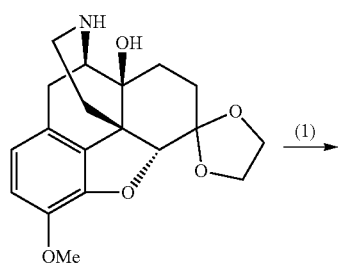

Compound 19

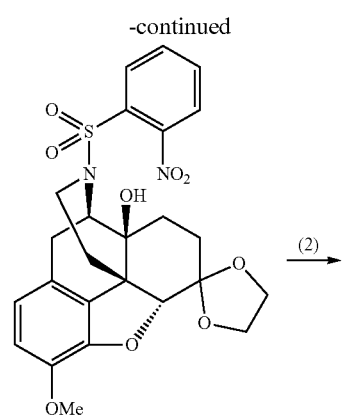

Compound 20

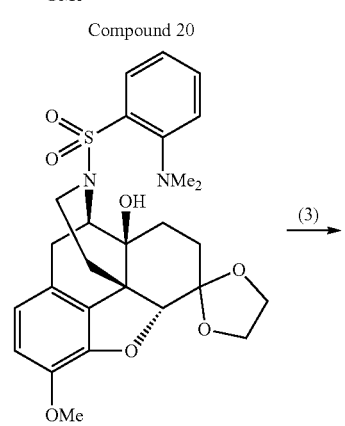

Compound 21

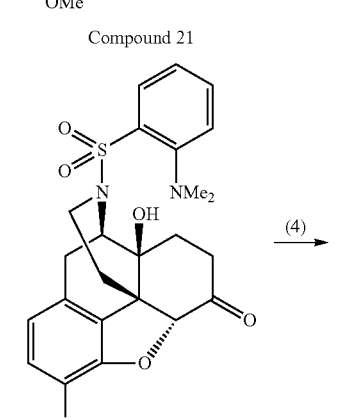

Compound 22

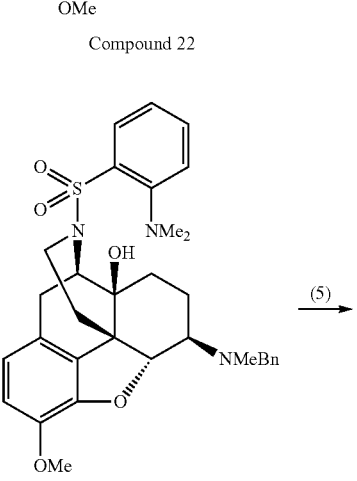

Compound 23

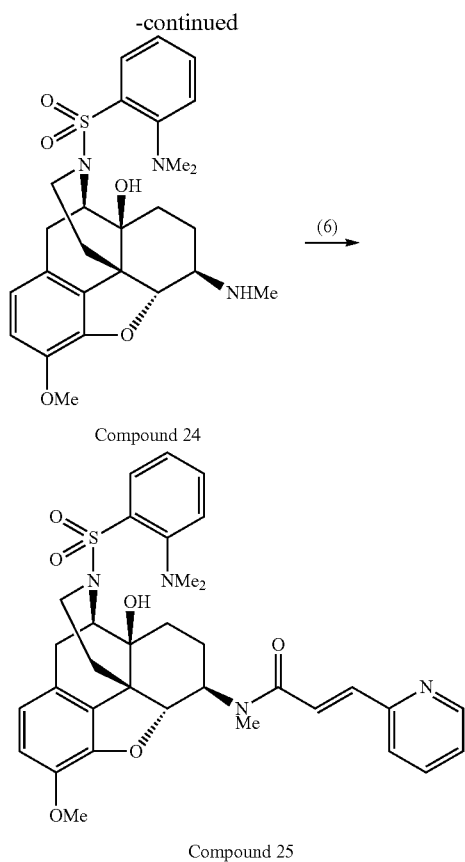

Compound 24

Compound 25

Step (1)

Synthesis of (4'R,4a'S,7a'R,12b'S)-9'-methoxy-3'-[(2-nitrophenyl)sulfonyl]-1',2',3',4',5',6'-hexahydro-4a'H,7a'H-spiro([1,3]dioxolane-2,7'-[4,12]methanobenzofuro[3,2-e]isoquinolin)-4a'-ol (Compound 20)

Under argon atmosphere, (4'R,4a'S,7a'R,12b'S)-9'-methoxy-1',2',3',4',5',6'-hexahydro-4a'H,7a'H-spiro[[1,3]dioxolane-2,7'-[4,12]methanobenzofuro[3,2-e]isoquinolin]-4a'-ol (Compound 19) (5.94 g, 17.2 mmol) was dissolved in anhydrous dichloromethane (100 mL), and triethylamine (6.0 mL, 43.0 mmol) was added thereto. To the resulting mixture, 2-nitrobenzenesulfonyl chloride (4.57 g, 20.6 mmol) was added on ice, and subsequently the resulting mixture was stirred at room temperature for 1 hour. A saturated aqueous solution of sodium hydrogencarbonate (80 mL) was added to the reaction mixture, and the resulting mixture was extracted with chloroform. The organic layer was washed with saturated brine, and then dried over sodium sulfate, and concentrated under reduced pressure. The obtained crude product was purified by silica gel column chromatography (0→5% (v/v) methanol/chloroform) to give the title compound 20 (9.06 g, 99%) as a yellow amorphous solid.

$^1$H-NMR (400 MHz, CDCl$_3$) δ (ppm): 1.47 (ddd, J=13.6, 3.6, 3.6 Hz, 1H), 1.52-1.63 (m, 3H), 2.11 (ddd, J=13.2, 9.2, 6.8 Hz, 1H), 2.40 (ddd, J=12.8, 12.8, 5.6 Hz, 1H), 3.03 (ddd, J=13.2, 13.2, 4.0 Hz, 1H), 3.06-3.15 (m, 2H), 3.19 (d, J=18.4 Hz, 1H), 3.74 (dd, J=13.2, 5.6 Hz, 1H), 3.79 (d, J=12.8, 6.8 Hz, 1H), 3.87 (s, 3H), 3.89 (dd, J=13.2, 6.8 Hz, 1H), 3.96 (d, J=4.8 Hz, 1H), 4.01 (dd, J=13.2, 6.8 Hz, 1H), 4.17 (dd, J=12.8, 6.8 Hz, 1H), 4.51 (s, 1H), 6.64 (d, J=8.4 Hz, 1H), 6.78 (d, J=8.4 Hz, 1H), 7.66-7.78 (m, 3H), 8.14 (dd, J=6.8, 2.4 Hz, 1H).

MS(ESI)[M+Na]$^+$=553

Step (2)

Synthesis of (4'R,4a'S,7a'R,12b'S)-3'-{[2-(dimethylamino) phenyl]sulfonyl}-9'-methoxy-1',2',3',4',5',6'-hexahydro-4a'H,7a'H-spiro[[1,3]dioxolane-2,7'-[4,12]methanobenzofuro[3,2-e]isoquinolin]-4a'-ol (Compound 21)

Under argon atmosphere, (4'R,4a'S,7a'R,12b'S)-9'-methoxy-3'-[(2-nitrophenyl)sulfonyl]-1',2',3',4',5',6'-hexahydro-4a'H,7a'H-spiro[[1,3]dioxolane-2,7'-[4,12]methanobenzofuro[3,2-e]isoquinolin]-4a'-ol (Compound 20) (9.06 g, 17.1 mmol) was suspended in ethanol (180 mL), and water (36 mL), a saturated ammonium chloride solution (25 mL) and iron powder (9.6 g, 172 mmol) were added thereto, and the resulting mixture was stirred at 90° C. After 1 hour, heating was stopped, and the mixture was allowed to cool to room temperature, and the reaction mixture was then filtered through Celite. The filtrate was concentrated under reduced pressure, and a saturated aqueous solution of sodium hydrogencarbonate (50 mL) was added to the residue, and the resulting mixture was extracted with chloroform. The organic layer was washed with saturated brine, dried over sodium sulfate, and then concentrated under reduced pressure. Under argon atmosphere, the obtained crude product was dissolved in acetic acid (200 mL), and paraformaldehyde (12.8 g, 426 mmol) and sodium cyanoborohydride (10.7 g, 170 mmol) were added thereto, and the resulting mixture was stirred at 40° C. After 3 hours, the reaction mixture was filtered through Celite, and the filtrate was concentrated under reduced pressure. A saturated sodium bicarbonate solution (300 mL) was added to the residue to adjust pH to 9, and the resulting mixture was extracted with chloroform. The organic layer was washed with saturated brine, dried over sodium sulfate, and then concentrated under reduced pressure. The obtained crude product was purified by silica gel column chromatography (0→10% (v/v) methanol/chloroform) to give the title compound 21 (9.32 g, 97%) as a colorless amorphous solid.

$^1$H-NMR (400 MHz, CDCl$_3$) δ (ppm): 1.42-1.63 (m, 4H), 2.10 (ddd, J=12.8, 12.8, 5.6 Hz, 1H), 2.24 (ddd, J=13.6, 13.6, 3.6 Hz, 1H), 2.83 (s, 6H), 2.93 (ddd, J=12.8, 12.8, 3.6 Hz, 1H), 3.04 (dd, J=18.4, 4.8 Hz, 1H), 3.07-3.14 (m, 1H), 3.14 (d, J=18.4 Hz, 1H), 3.78 (dd, J=12.8, 6.8 Hz, 1H), 3.87 (s, 3H), 3.89 (dd, J=13.6, 6.8 Hz, 1H), 4.01 (dd, J=13.6, 6.8 Hz, 1H), 4.12-4.2 (m, 2H), 4.53 (s, 1H), 4.92 (brs, 1H), 6.62 (d, J=8.4 Hz, 1H), 6.76 (d, J=8.4 Hz, 1H), 7.21-7.28 (m, 1H), 7.37 (dd, J=8.0, 0.8 Hz, 1H), 7.58 (ddd, J=8.0, 8.0, 1.6 Hz, 1H), 8.13 (dd, J=8.0, 1.6 Hz, 1H).

MS(ESI)[M+Na]$^+$=551

Step (3)

Synthesis of (4R,4aS,7aR,12bS)-3-{[2-(dimethylamino) phenyl]sulfonyl}-4a-hydroxy-9-methoxy-2,3,4,4a,5,6-hexahydro-1H-4,12-methanobenzofuro[3,2-e]isoquinolin-7(7aH)-one (Compound 22)

Under argon atmosphere, (4'R,4a'S,7a'R,12b'S)-3'-{[2-(dimethylamino) phenyl]sulfonyl}-9'-methoxy-1',2',3',4',5',6'-hexahydro-4a'H,7a'H-sporo([1,3]dioxolane-2,7'-[4,12] methanobenzofuro[3,2-e]isoquinolin)-4a'-ol (Compound 21) was dissolved in THF (100 mL), and 2 M hydrochloric acid (100 mL) was added thereto, and the resulting mixture was stirred at 90° C. After 9 hours, heating was stopped, and the mixture was allowed to cool to room temperature, and the reaction mixture was then concentrated under reduced pressure. A saturated aqueous solution of sodium hydrogencarbonate (120 mL) was added to the residue to adjust pH to 9, and the resulting mixture was extracted with chloroform. The organic layer was washed with saturated brine, dried over sodium sulfate, and then concentrated under reduced pressure. The obtained crude product was purified by silica gel column chromatography (diol-modified silica gel, ethyl acetate:n-hexane=1:5→1:2) to give the title compound 22 (5.4 g, 90%) as a colorless amorphous solid.

$^1$H-NMR (400 MHz, CDCl$_3$) δ (ppm): 1.53-1.69 (m, 2H), 1.92 (ddd, J=13.2, 4.8, 3.2 Hz, 1H), 2.26 (ddd, J=12.8, 12.8, 5.2 Hz, 1H), 2.30 (ddd, J=14.0, 2.8, 2.8 Hz, 1H), 2.86 (s, 6H), 2.92 (ddd, J=12.8, 12.8, 3.6 Hz, 1H), 2.99-3.17 (m, 3H), 3.17 (d, 18.8 Hz, 1H), 3.87 (s, 3H), 4.29 (d, J=5.2 Hz, 1H), 4.64 (s, 1H), 5.38 (s, 1H), 6.65 (d, J=8.4 Hz, 1H), 6.73 (d, J=8.4 Hz, 1H), 7.23-7.30 (m, 1H), 7.41 (dd, J=8.0, 0.8 Hz, 1H), 7.62 (ddd, J=8.0, 8.0, 1.6 Hz, 1H), 8.15 (dd, J=8.0, 1.6 Hz, 1H)

MS(ESI)[M+Na]$^+$=507

Step (4)

Synthesis of (4R,4aS,7R,7aR,12bS)-7-[benzyl(methyl) amino]-3-{[2-(dimethylamino) phenyl]sulfonyl}-9-methoxy-1,2,3,4,5,6,7,7a-octahydro-4aH-4,12-methanobenzofuro[3,2-e]isoquinolin-4a-ol (Compound 23)

Under argon atmosphere, (4R,4aS,7R,7aR,12bS)-3-{[2-(dimethylamino) phenyl]sulfonyl}-4a-hydroxy-9-methoxy-2,3,4,4a,5,6-hexahydro-1H-4,12-methanobenzofuro[3,2-e]isoquinolin-7(7aH)-one (Compound 22) (1.07 g, 2.20 mmol) was dissolved in benzene (30 mL), and benzoic acid (273 mg, 2.24 mmol) and N-benzylmethylamine (0.57 mL, 4.41 mmol) were added thereto. The reaction mixture was heated for 21 hours under reflux with removal of water through an equipped Dean-Stark trap, and then concentrated under reduced pressure. Under argon atmosphere, anhydrous methanol (13 mL) and anhydrous THF (20 mL) were added to the residue to dissolve the residue, and the resulting solution was stirred on ice. Sodium cyanoborohydride (167 mg, 2.65 mmol) was added thereto, and the resulting mixture was stirred for 45 minutes. A saturated aqueous solution of sodium hydrogencarbonate (20 mL) and saturated brine (20 mL) was added to the reaction mixture, and the resulting mixture was extracted with chloroform. The organic layers was dried over sodium sulfate, and then concentrated under reduced pressure. The obtained crude product was purified by silica gel column chromatography (NH silica gel, ethyl acetate:n-hexane=3:1) to give the title compound 23(1.04 g, 80%) as a colorless amorphous solid.

$^1$H-NMR (400 MHz, CDCl$_3$) δ (ppm): 1.27-1.38 (m, 1H), 1.47 (dd, J=12.8, 2.4 Hz, 1H), 1.52-1.66 (m, 2H), 1.92-2.11 (m, 2H), 2.32 (s, 3H), 2.57 (ddd, J=12.4, 7.6, 4.8 Hz, 1H), 2.83 (s, 6H), 2.89 (ddd, J=12.8, 12.8, 3.6 Hz, 1H), 2.99 (dd, J=18.4, 5.2 Hz, 1H), 3.09 (d, J=18.4 Hz, 1H), 3.09-3.17 (m, 1H), 3.67 (d, J=13.6 Hz, 1H), 3.79 (d, J=13.6 Hz, 1H), 3.87 (s, 3H), 4.11 (d, J=4.8 Hz, 1H), 4.68 (d, J=8.0 Hz, 1H), 4.73 (s, 1H), 6.58 (d, J=8.4 Hz, 1H), 6.70 (d, J=8.4 Hz, 1H), 7.16-7.32 (m, 4H), 7.37 (d, J=7.6 Hz, 3H), 7.55-7.61 (m, 1H), 8.12 (dd, J=7.6, 1.2 Hz, 1H)

MS(ESI)[M+H]$^+$=590

Step (5)

Synthesis of (4R,4aS,7R,7aR,12bS)-3-{[2-(dimethylamino) phenyl]sulfonyl}-9-methoxy-7-(methylamino)-1,2,3,4,5,6,7,7a-octahydro-4aH-4,12-methanobenzofuro[3,2-e]isoquinolin-4a-ol (Compound 24)

(4R,4aS,7R,7aR,12bS)-7-[benzyl(methyl) amino]-3-{[2-(dimethylamino) phenyl]sulfonyl}-9-methoxy-1,2,3,4,5,6,7,7a-octahydro-4aH-4,12-methanobenzofuro[3,2-e]isoquinolin-4a-ol (Compound 23) (698 mg, 1.18 mmol) was dissolved in methanol (20 mL) and THF (10 mL), and 5% palladium on activated carbon (Degussa type) (678 mg) was added thereto. The reaction mixture was stirred at room temperature for 7.5 hours under hydrogen atmosphere, and then filtered through Celite, and the filtrate was concentrated under reduced pressure. The obtained crude product was purified by silica gel column chromatography (aqueous ammonia:methanol:chloroform=1:9:490→1:9:40) to give the title compound 24(570 mg, 96%) as a colorless amorphous solid.

$^1$H-NMR (400 MHz, CDCl$_3$) δ (ppm): 1.34 (ddd, J=12.8, 12.8, 3.2 Hz, 1H), 1.45 (dd, J=12.8, 1.6 Hz, 1H), 1.58-1.67 (m, 1H), 1.68-1.89 (m, 2H), 2.08 (ddd, J=12.8, 12.8, 5.6 Hz, 1H), 2.45-2.53 (m, 1H), 2.51 (s, 3H), 2.82 (m, 6H), 2.89 (ddd, J=12.8, 12.8, 3.2 Hz, 1H), 3.04 (dd, J=18.4, 5.2, 1H), 3.06-3.14 (m, 1H), 3.15 (d, J=18.4 Hz, 1H), 3.86 (s, 3H), 4.15 (d, J=5.2 Hz, 1H), 4.46 (d, J=6.8 Hz, 1H), 6.64 (d, J=8.4 Hz, 1H), 6.74 (d, J=8.4 Hz, 1H), 7.20-7.26 (m, 1H), 7.34-7.39 (m, 1H), 7.55-7.61 (m, 1H), 8.10-8.14 (m, 1H). No 2H(OH, NH) was detected.

MS(ESI)[M+H]$^+$=500

Step (6)

Synthesis of (E)-N-[(4R,4aS,7R,7aR,12bS)-3-{[2-(dimethylamino) phenyl]sulfonyl}-4a-hydroxy-9-methoxy-2,3,4,4a,5,6,7,7a-octahydro-1H-4,12-methanobenzofuro[3,2-e]isoquinolin-7-yl]-N-methyl-3-(pyridin-2-yl)acrylamide (Compound 25)

Under argon atmosphere, (4R,4aS,7R,7aR,12bS)-3-{[2-(dimethylamino) phenyl]sulfonyl}-9-methoxy-7-(methylamino)-1,2,3,4,5,6,7,7a-octahydro-4aH-4,12-methanobenzofuro[3,2-e]isoquinolin-4a-ol (Compound 24) (229 mg, 0.461 mmol) was dissolved in DMF (8 mL), and 3-(2-pyridyl)acrylic acid (75.7 mg, 0.508 mmol), HATU (437 mg, 1.15 mmol) and N,N-diisopropylethylamine (0.25 mL, 1.38 mmol) were added thereto. After 2 hours of stirring at room temperature, the reaction liquid was poured into ethyl acetate (70 mL), and washed with water (100 mL×4). The organic layer was dried over sodium sulfate, and concentrated under reduced pressure. The obtained crude product was purified by silica gel column chromatography (aqueous ammonia:methanol:chloroform=1:9:990→1:9:490) to give the free form of the title compound 25 (277 mg, 95%) as a colorless amorphous solid. The obtained free form of the compound was dissolved in methanol, a sulfuric acid solution in methanol was added thereto, and diethylether was then added thereto to precipitate a disulfate salt of the title compound 25 (Compound 26).

Compound 26

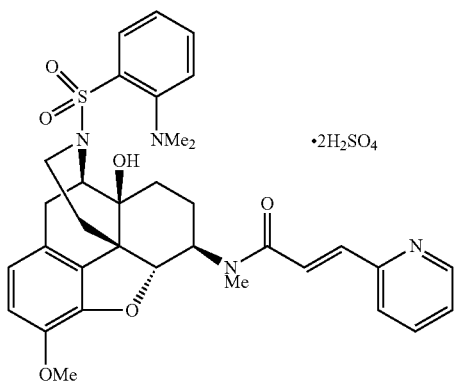 [SMILES: COc1ccc2c3c1O[C@H]1[C@H](N(C)C(=O)CCc4ccccc4)CC[C@@]4(O)[C@@H](C2)N(S(=O)(=O)c2ccccc2)CC[C@]314]

(Free form (Compound 25))
$^1$H-NMR (400 MHz, CDCl$_3$) δ (ppm): 1.41-1.59 (m, 3H), 1.62-1.75 (m, 1H), 2.04-2.37 (m, 2H), 2.75-2.97 (m, 7H), 2.98-3.24 (m, 6H), 3.50 (s, 1.8H), 3.81-3.92 (m, 1.8H), 4.14 (d, J=4.0 Hz, 0.4H), 4.18 (d, J=4.0 Hz, 0.6H), 4.30-4.33 (m, 0.4H), 4.57 (d, J=7.6 Hz, 0.6H), 4.71-4.80 (m, 0.8H), 4.93 (s, 0.6H), 6.60-6.71 (m, 1.6H), 6.75 (d, J=8.4 Hz, 0.4H), 7.11-7.43 (m, 4.6H), 7.48 (d, J=15.2 Hz, 0.4H), 7.54-7.73 (m, 3H), 8.13 (d, J=7.6 Hz, 1H), 8.52 (d, J=4.4 Hz, 0.6H), 8.62 (d, J=4.4 Hz, 0.4H).
MS(ESI)[M+H]$^+$=631
(Disulfate salt (Compound 26))
mp(dec.): 217-220° C.
Elementary analysis as C$_{34}$H$_{38}$N$_4$O$_6$S.2H$_2$SO$_4$.4H$_2$O
Calculated: C, 45.43; H, 5.61; N, 6.23.
Observed: C, 45.49; H, 5.52; N, 6.10.

Test Example 1

Measurement of Antagonistic Activity Against Orexin Receptors

The Chinese hamster ovary (CHO) cell lines CHOOX1R and CHOOX2R were established by modifying CHO cells to constantly express the NFAT-luciferase gene and either the human OX1R or human OX2R gene. Those cells were plated at 10,000 cells/well in 96-well multiplates with DMEM (manufactured by Sigma-Aldrich Co. LLC) supplemented with 5% FBS (manufactured by Thermo Scientific Inc.) and incubated at 37° C. and 5% CO$_2$ for 48 hours. After removal of the medium, 100 μL of an assay buffer (20 mM HEPES (manufactured by Sigma-Aldrich Co. LLC), Hank's balanced salt solution (manufactured by Gibco), 0.1% BSA (manufactured by Sigma-Aldrich Co. LLC), 2.5 mM probenecid acid (manufactured by Wako Pure Chemical Industries, Ltd.), pH 7.4) containing 5 μM Fura-2AM (manufactured by Cayman Chemical Co.) was added to each well, and incubated at 37° C. and 5% CO$_2$ for 60 minutes. After removal of the buffer containing Fura-2AM, 75 μL of the assay buffer was added to each well. Then, 25 L of the assay buffer containing a test compound at various concentrations and OX-A (manufactured by Peptide Institute, Inc.) was added to start the reaction. The change in intracellular calcium ion concentration induced by the reaction was evaluated by the ratio of fluorescent intensities, which were measured at a wavelength of 510 nm based on the two wavelength excitation approach using FDSS 7000 (manufactured by Hamamatsu Photonics K.K.) with fluorescence excitation at 340 nm and 380 nm. A concentration-response curve on the antagonistic activity was plotted from the values of maximal fluorescent intensity ratio determined when various concentrations of a test compound were added in the presence of 300 μM of OX-A, where a value of maximal fluorescent intensity ratio determined by adding 300 pM of OX-A alone corresponds to 100% and a value of maximal fluorescent intensity ratio determined by adding the assay buffer alone corresponds to 0%. Based on the resulting non-linear regression curve, the 50% maximal inhibitory concentration (IC$_{50}$) was calculated. Each test compound was dissolved in DMSO to a concentration of 10 mM (the final concentration of DMSO was 1%), and then diluted with the assay buffer to give a final concentration of $3.0×10^{-10}$ M to $1.0×10^{-5}$ M (a common ratio of 3), while OX-A was diluted to a final concentration of 300 pM. The experiment was performed in quadruplicate plates, and the results of the four independent measurements were averaged to give the value of each reaction, and then the IC$_{50}$ of a sample was calculated. If the sample number was 2 or more, the averaged IC$_{50}$ was used.

The IC$_{50}$ of the compounds synthesized in Comparative Examples and Examples are presented in Table 6. As seen from the results in Table 6, the compounds of Examples 1, 2, 3, 4, 5, 8, 11, 15, 18, 20, 21, 23, 25, 27, 28, 32, 34, 35, 38, 41, 42 and 45 exhibited a potent and selective antagonistic activity against human OX1 receptor. On the other hand, the compounds of Comparative Example 1 and Comparative Example 2 exhibited a very weak antagonistic activity against human OX1 receptor.

TABLE 6

| Example No. | OX1 (IC$_{50}$) nM | OX2 (IC$_{50}$) nM | Sample number |
| --- | --- | --- | --- |
| Compound of Comparative Example 1 (Compound 1) | 1650 | >10000 | 5 |
| Compound of Comparative Example 2 (Compound 3) | 2850 | >10000 | 1 |
| Compound of Example 1 (Compound 6) | 82.8 | >10000 | 2 |
| Compound of Example 2 | 30.0 | >10000 | 2 |
| Compound of Example 3 | 24.0 | >10000 | 2 |
| Compound of Example 4 | 162 | >10000 | 3 |
| Compound of Example 5 | 419 | >10000 | 1 |
| Compound of Example 8 | 144 | >10000 | 3 |
| Compound of Example 11 | 49.1 | >10000 | 2 |
| Compound of Example 15 | 112 | >10000 | 1 |
| Compound of Example 18 | 195 | >10000 | 1 |
| Compound of Example 20 | 56.2 | >10000 | 2 |
| Compound of Example 21 | 200 | >10000 | 1 |
| Compound of Example 23 | 121 | >10000 | 1 |
| Compound of Example 25 | 198 | >10000 | 2 |
| Compound of Example 27 | 87.8 | >10000 | 2 |
| Compound of Example 28 | 101 | >10000 | 2 |
| Compound of Example 32 | 11.7 | >10000 | 1 |
| Compound of Example 34 | 259 | >10000 | 1 |
| Compound of Example 35 | 571 | >10000 | 2 |
| Compound of Example 38 (Compound 14) | 128 | >10000 | 1 |
| Compound of Example 41 | 159 | >10000 | 2 |
| Compound of Example 42 | 688 | >10000 | 1 |
| Compound of Example 45 (Compound 26) | 3.61 | >10000 | 1 |

The above results indicate that morphinan derivatives of the present invention or pharmaceutically acceptable acid addition salts thereof have an excellent selective antagonistic activity against human OX1 receptor.

Test Example 2

Evaluation of the Prophylactic Effect on Drug Dependence

Increasing doses of morphine hydrochloride dissolved in saline were administered subcutaneously to 7-week-old male ICR mice twice daily (dosing interval: about 12 hours) for four days (dose: Day 1, 8 mg/kg followed by 15 mg/kg; Day 2, 20 mg/kg followed by 25 mg/kg; Day 3, 30 mg/kg followed by 35 mg/kg; Day 4, 40 mg/kg followed by 45 mg/kg). On Day 1 to Day 4, the mice were administered intraperitoneally with the compound of Example 45 (Compound 26) at 10 mg/kg or saline, the solvent of the compound, 30 minutes prior to every first administration of morphine hydrochloride. On Day 5, the mice were administered subcutaneously with the compound of Example 45 (Compound 26) at 10 mg/kg or saline, and 30 minutes later administered subcutaneously with morphine hydrochloride at 45 mg/kg as the final dose. Two hours after the final administration of morphine hydrochloride, the mice were administered subcutaneously with naloxone hydrochloride at 3 mg/kg; symptoms of withdrawal syndrome (jumping, body shake, ptosis, forepaw tremor, rearing, body weight loss, and diarrhea) which appeared 60 minutes after administration of naloxone hydrochloride were observed. Body weight was measured before and every 15 minutes after naloxone hydrochloride administration. Moreover, diarrhea was graded according to a three-point scoring system based on the appearance of feces: normal feces (Normal), loose feces (Slightly), and liquid feces or liquid diarrhea (Severe). The other symptoms of withdrawal syndrome were evaluated based on the presence or absence of their manifestation. Statistical analysis was performed using chi square test and two-way analysis of variance and setting the significance level at $p<0.05$.

As shown in Table 7, Table 8 and FIG. 1, jumping, diarrhea and body weight loss, which are included in symptoms of withdrawal syndrome, were statistically significantly suppressed by repeated administration of the compound of Example 45 (Compound 26) in combination with the narcotic drug, morphine hydrochloride. Also, the tendency to suppress ptosis and rearing was observed. This result indicated that the incidence of morphine physical dependence was suppressed, indicating the prophylactic effect of the compound.

TABLE 7

| Withdrawal syndrome | Saline + morphine-dosing group | Compound of Example 45 (Compound 26) + morphine-dosing group |
|---|---|---|
| Jumping | 6/8 | 1/8* |
| Body shake | 7/8 | 6/8 |
| Ptosis | 6/8 | 4/8 |
| Forepaw tremor | 7/8 | 6/8 |
| Rearing | 8/8 | 5/8 |

The asterisk in the table indicates the statistical significance ($p < 0.05$) of the comparison between the saline + morphine-dosing group and the compound of Example 45 (Compound 26) + morphine-dosing group.

TABLE 8

| Group | Diarrhea score (Number of corresponding animals/total number of animals) | | |
|---|---|---|---|
| | Normal feces | Loose feces | Liquid feces or liquid diarrhea |
| Saline + morphine-dosing group | 0/8 | 1/8 | 7/8 |
| Compound of Example 45 (Compound 26) + morphine-dosing group* | 2/8 | 4/8 | 2/8 |

The asterisk in the table indicates the statistical significance ($p < 0.05$) of the comparison between the saline + morphine-dosing group and the compound of Example 45 (Compound 26) + morphine-dosing group.

Test Example 3

Evaluation of the Therapeutic Effect on Drug Dependence

Increasing doses of morphine hydrochloride dissolved in saline were administered subcutaneously to 7-week-old male ICR mice twice daily (dosing interval: about 12 hours) for four days (dose: Day 1, 8 mg/kg followed by 15 mg/kg; Day 2, 20 mg/kg followed by 25 mg/kg; Day 3, 30 mg/kg followed by 35 mg/kg; Day 4, 40 mg/kg followed by 45 mg/kg). On Day 5, the mice were administered subcutaneously with morphine hydrochloride at 45 mg/kg as the final dose. Two hours after the final administration of morphine hydrochloride, the mice were administered subcutaneously with naloxone hydrochloride at 3 mg/kg. The mice were administered intraperitoneally with the compound of Example 45 (Compound 26) at 10 mg/kg or saline, the solvent of the compound, 30 minutes prior to the administration of naloxone hydrochloride. Symptoms of withdrawal syndrome (jumping, body shake, ptosis, forepaw tremor, rearing, body weight loss, and diarrhea) which appeared 60 minutes after the last dose of naloxone hydrochloride were observed. Body weight was measured before and every 15 minutes after naloxone hydrochloride administration. Moreover, diarrhea was graded according to a three-point scoring system based on the appearance of feces: normal feces, loose feces, and liquid feces or liquid diarrhea. The other symptoms of withdrawal syndrome were evaluated based on the presence or absence of their manifestation. Statistical analysis was performed using chi square test and two-way analysis of variance and setting the significance level at $p<0.05$.

Figure 2:
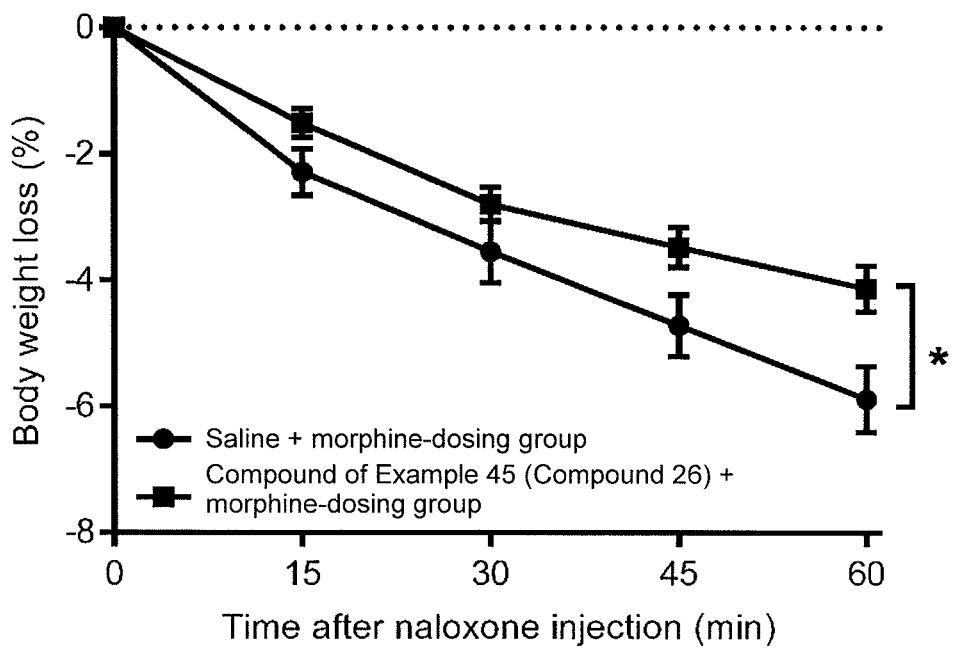
FIG. 2 depicts the effect of the compound of Example 45 (Compound 26) on the withdrawal state in mice with morphine physical dependence (body weight loss). The asterisk indicates the statistical significance at p<0.05.

As shown in Table 9, Table 10 and FIG. 2, jumping, diarrhea and body weight loss, which are included in symptoms of withdrawal syndrome, were statistically significantly suppressed by administration of the compound of Example 45 (Compound 26) after the repetitive administration of morphine hydrochloride and before the administration of naloxone hydrochloride. Also, the tendency to suppress ptosis was observed. This result indicated that the withdrawal state in morphine physical dependence was suppressed, indicating the therapeutic effect of the compound.

TABLE 9

| Withdrawal syndrome | Saline + morphine-dosing group | Compound of Example 45 (Compound 26) + morphine-dosing group |
|---|---|---|
| Jumping | 9/13 | 2/13** |
| Body shake | 9/13 | 7/13 |
| Ptosis | 6/13 | 3/13 |
| Forepaw tremor | 12/13 | 11/13 |
| Rearing | 12/13 | 11/13 |

Number of animals with withdrawal syndrome/total number of animals

The double asterisk in the table indicates the statistical significance ($p < 0.01$) of the comparison between the saline + morphine-dosing group and the compound of Example 45 (Compound 26) + morphine-dosing group.

TABLE 10

| Group | Normal feces | Loose feces | Liquid feces or liquid diarrhea |
|---|---|---|---|
| Saline + morphine-dosing group | 0/13 | 3/13 | 10/13 |
| Compound of Example 45 (Compound 26) + morphine-dosing group* | 2/13 | 8/13 | 3/13 |

Diarrhea score (Number of corresponding animals/total number of animals)

The asterisk in the table indicates the statistical significance ($p < 0.05$) of the comparison between the saline + morphine-dosing group and the compound of Example 45 (Compound 26) + morphine-dosing group.

Accordingly, it is clear that a morphinan derivative of the present invention or a pharmaceutically acceptable acid addition salt thereof has excellent prophylactic and therapeutic effects on drug dependence.

INDUSTRIAL APPLICABILITY

Because a morphinan derivative of the present invention or a pharmaceutically acceptable acid addition salt thereof can exert excellent selectivity for and antagonism against orexin receptors, it is successfully used as a pharmaceutical drug for various diseases and symptoms related to orexin receptors.

The invention claimed is:

1. A morphinan derivative represented by the general formula (I) below or a pharmaceutically acceptable acid addition salt thereof

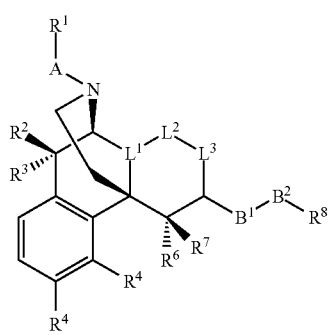

(I)

[wherein $L^1$-$L^2$-$L^3$ represents C($R^9$)—CH$_2$—CH$_2$, C($R^9$)—CH=CH, or C=CH—CH$_2$, wherein $R^9$ represents a hydrogen atom, hydroxy, nitro, $C_1$-$C_5$ alkanoyloxy, $C_1$-$C_5$ alkoxy, $C_1$-$C_5$ alkyl, amino, monoalkylamino (the alkyl moiety has one to five carbon atoms), dialkylamino (the alkyl moiety has one to five carbon atoms), $C_1$-$C_5$ alkanamide, benzamide, or $C_7$-$C_{14}$ aryl-alkanamide;

A represents —C(=O)— or —SO$_2$—;

$R^1$ represents $C_1$-$C_7$ linear or branched alkyl, $C_3$-$C_6$ cycloalkyl, $C_4$-$C_7$ cycloalkylalkyl, $C_4$-$C_6$ cycloalkenyl, $C_5$-$C_7$ cycloalkenylalkyl, $C_7$-$C_{13}$ aralkyl, $C_4$-$C_7$ alkenyl, allyl, styryl, anilino, or an organic group containing any of basic skeletons (II) below, wherein, in the basic skeletons (II), * represents the point of attachment; said organic group represented by $R^1$ is optionally substituted by at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, carboxy, carbamoyl, N,N-dialkylcarbamoyl (the alkyl moiety has one to five carbon atoms), amidino, guanidino, isothiocyanate, trifluoromethyl, phenyl, trifluoromethoxy, and methylenedioxy;

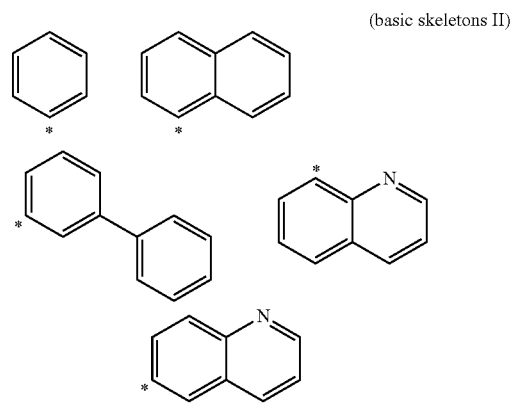

(basic skeletons II)

both $R^2$ and $R^3$ represent a hydrogen atom, or one of $R^2$ and $R^3$ represents a hydrogen atom and the other represents hydroxy, or $R^2$ and $R^3$ together represent oxo;

$R^4$ represents a hydrogen atom, hydroxy, $C_1$-$C_5$ alkoxy, $C_3$-$C_7$ alkenyloxy, $C_7$-$C_{13}$ aralkyloxy, or $C_1$-$C_5$ alkanoyloxy;

$R^5$ and $R^6$ together represent —O—, —S—, or —CH$_2$—, or $R^6$ represents a hydrogen atom and $R^5$ represents a hydrogen atom, hydroxy, $C_1$-$C_5$ alkoxy, or $C_1$-$C_5$ alkanoyloxy;

$R^7$ represents a hydrogen atom, $C_1$-$C_5$ alkyl, $C_2$-$C_5$ alkenyl, or $C_7$-$C_{13}$ aralkyl;

$B^1$ represents —N($R^{10}$)C(=O)— or —NR$^{10}$—, wherein $R^{10}$ represents a hydrogen atom, $C_1$-$C_5$ linear or branched alkyl;

$B^2$ represents a valence bond, $C_1$-$C_{14}$ linear or branched alkylene (provided that said alkylene is optionally substituted with at least one substituent selected from the group consisting of $C_1$-$C_5$ alkoxy, $C_1$-$C_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, carboxy, carbamoyl, amidino, guanidino, trifluoromethyl, phenyl and phenoxy; and one to three methylene groups are optionally replaced with carbonyl groups), $C_2$-$C_{14}$ linear or branched acyclic unsaturated divalent hydrocarbon group containing one to three double and/or triple bonds (provided that said hydrocarbon group is optionally substituted with at least one substituent selected from the group consisting of $C_1$-$C_5$ alkoxy, $C_1$-$C_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, carboxy, carbamoyl, amidino, guanidino, trifluoromethyl, trifluoromethoxy, phenyl, and phenoxy; and one to three methylene groups are optionally replaced with carbonyl groups), or $C_1$-$C_{14}$ linear or branched saturated or unsaturated divalent hydrocarbon group containing one to five thioether bonds, ether bonds, and/or amino bonds (—N(H)—) (provided that the hetero atom comprised in said thioether bond, ether bond, or amino bond is not directly linked to $B^1$; and one to three methylene groups are optionally replaced with carbonyl or sulfonyl groups);

$R^8$ represents a hydrogen atom or an organic group containing any of basic skeletons (III) below, wherein, in the basic skeletons (III), * represents the point of attachment; Q represents N, O, or S; said organic group represented by $R^8$ is optionally substituted by at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, isothiocyanate, trifluoromethyl, phenyl, phenoxy, trifluoromethoxy, and methylenedioxy; and (basic skeletons III)

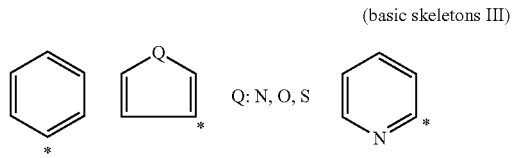

said general formula (I) inclusively represents the (+)-form, the (−)-form, and the (±)-form of the molecule].

2. The morphinan derivative or the pharmaceutically acceptable acid addition salt thereof according to claim 1, wherein $L^1$-$L^2$-$L^3$ represents C($R^9$)—$CH_2$—$CH_2$ (where $R^9$ has the same definition as above) or C=CH—$CH_2$, and wherein $R^5$ and $R^6$ together represent —O—.

3. The morphinan derivative or the pharmaceutically acceptable acid addition salt thereof according to claim 1 or 2, wherein $R^8$ represents an organic group containing any of basic skeletons below

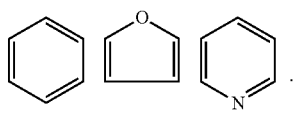

4. The morphinan derivative or the pharmaceutically acceptable acid addition salt thereof according to claim 1, wherein $R^1$ represents an organic group containing any of basic skeletons below

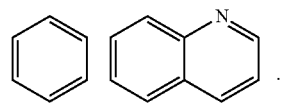

5. The morphinan derivative or the pharmaceutically acceptable acid addition salt thereof according to claim 1, wherein $R^4$ represents a $C_1$-$C_5$ alkoxy or $C_7$-$C_{13}$ aralkyloxy group.

6. A pharmaceutical drug comprising, as an active ingredient, the morphinan derivative or the pharmaceutically acceptable acid addition salt thereof according to claim 1.

7. A pharmaceutical composition comprising, as an active ingredient, the morphinan derivative or the pharmaceutically acceptable acid addition salt thereof according to claim 1.

8. An orexin receptor antagonist comprising, as an active ingredient, the morphinan derivative or the pharmaceutically acceptable acid addition salt thereof according to claim 1.

9. A therapeutic agent for drug dependence comprising, as an active ingredient, the morphinan derivative or the pharmaceutically acceptable acid addition salt thereof according to claim 1.

10. A therapeutic method for drug dependence, the method comprising administering an effective amount of the morphinan derivative or the pharmaceutically acceptable acid addition salt thereof according to claim 1 to a mammal in need of treating drug dependence.

11. A morphinan derivative represented by the general formula (I) below or a pharmaceutically acceptable acid addition salt thereof for use in treatment of drug dependence (I)

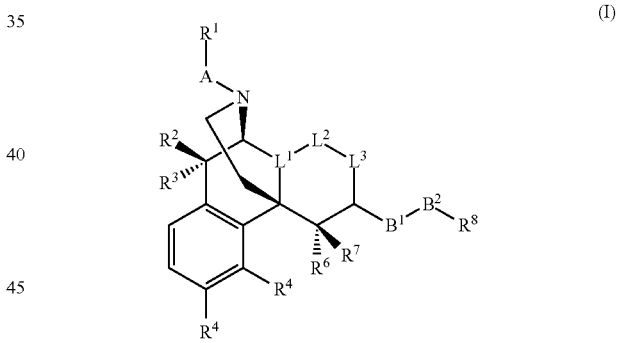

[wherein $L^1$-$L^2$-$L^3$ represents C($R^9$)—$CH_2$—$CH_2$, C($R^9$)—CH=CH, or C=CH—$CH_2$, wherein $R^9$ represents a hydrogen atom, hydroxy, nitro, $C_1$-$C_5$ alkanoyloxy, $C_1$-$C_5$ alkoxy, $C_1$-$C_5$ alkyl, amino, monoalkylamino (the alkyl moiety has one to five carbon atoms), dialkylamino (the alkyl moiety has one to five carbon atoms), $C_1$-$C_5$ alkanamide, benzamide, or $C_7$-$C_{14}$ aryl-alkanamide;

A represents —C(=O)— or —$SO_2$—;

$R^1$ represents $C_1$-$C_7$ linear or branched alkyl, $C_3$-$C_6$ cycloalkyl, $C_4$-$C_7$ cycloalkylalkyl, $C_4$-$C_6$ cycloalkenyl, $C_5$-$C_7$ cycloalkenylalkyl, $C_7$-$C_{13}$ aralkyl, $C_4$-$C_7$ alkenyl, allyl, styryl, anilino, or an organic group containing any of basic skeletons (II) below, wherein, in the basic skeletons (II), * represents the point of attachment; said organic group represented by $R^1$ is optionally substituted by at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, carboxy, carbamoyl, N,N-dialkylcarbamoyl (the alkyl moiety has one to five carbon atoms), amidino, guanidino, isothiocyanate, trifluoromethyl, phenyl, trifluoromethoxy, and methylenedioxy;

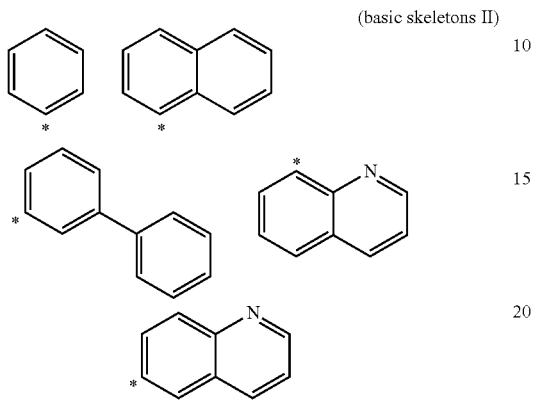

(basic skeletons II)

both $R^2$ and $R^3$ represent a hydrogen atom, or one of $R^2$ and $R^3$ represents a hydrogen atom and the other represents hydroxy, or $R^2$ and $R^3$ together represent oxo;

- $R^4$ represents a hydrogen atom, hydroxy, $C_1$-$C_5$ alkoxy, $C_3$-$C_7$ alkenyloxy, $C_7$-$C_{13}$ aralkyloxy, or $C_1$-$C_5$ alkanoyloxy;
- $R^5$ and $R^6$ together represent —O—, —S—, or -CH$_2$-, or $R^6$ represents a hydrogen atom and $R^5$ represents a hydrogen atom, hydroxy, $C_1$-$C_5$ alkoxy, or $C_1$-$C_5$ alkanoyloxy;
- $R^7$ represents a hydrogen atom, $C_1$-$C_5$ alkyl, $C_2$-$C_5$ alkenyl, or $C_7$-$C_{13}$ aralkyl;
- $B^1$ represents —N($R^{10}$) C(=O)— or —NR$^{10}$—, wherein $R^{10}$ represents a hydrogen atom, $C_1$-$C_5$ linear or branched alkyl;
- $B^2$ represents a valence bond, $C_1$-$C_{14}$ linear or branched alkylene (provided that said alkylene is optionally substituted with at least one substituent selected from the group consisting of $C_1$-$C_5$ alkoxy, $C_1$-$C_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, carboxy, carbamoyl, amidino, guanidino, trifluoromethyl, phenyl and phenoxy; and one to three methylene groups are optionally replaced with carbonyl groups), $C_2$-$C_{14}$ linear or branched acyclic unsaturated divalent hydrocarbon group containing one to three double and/or triple bonds (provided that said hydrocarbon group is optionally substituted with at least one substituent selected from the group consisting of $C_1$-$C_5$ alkoxy, $C_1$-$C_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, carboxy, carbamoyl, amidino, guanidino, trifluoromethyl, trifluoromethoxy, phenyl, and phenoxy; and one to three methylene groups are optionally replaced with carbonyl groups), or $C_1$-$C_{14}$ linear or branched saturated or unsaturated divalent hydrocarbon group containing one to five thioether bonds, ether bonds, and/or amino bonds (—N(H)—) (provided that the hetero atom comprised in said thioether bond, ether bond, or amino bond is not directly linked to $B^1$; and one to three methylene groups are optionally replaced with carbonyl or sulfonyl groups);
- $R^8$ represents a hydrogen atom or an organic group containing any of basic skeletons (III) below, wherein, in the basic skeletons (III), * represents the point of attachment; Q represents N, O, or S; said organic group represented by $R^8$ is optionally substituted by at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, monoalkylamino (the alkyl moiety has one to five carbon atoms), dialkylamino (the alkyl moiety has one to five carbon atoms), nitro, cyano, isothiocyanate, trifluoromethyl, phenyl, phenoxy, trifluoromethoxy, and methylenedioxy; and

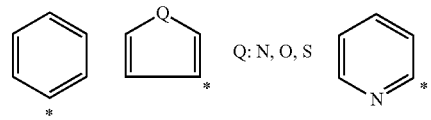

(basic skeletons III)

said general formula (I) inclusively represents the (+)-form, the (−)-form, and the (±)-form of the molecule].

* * * * *